United States Patent
Nakanishi et al.

(10) Patent No.: US 7,247,645 B2
(45) Date of Patent: Jul. 24, 2007

(54) DIHYDROPYRIDINE DERIVATIVES

(75) Inventors: Chika Nakanishi, Kawasaki (JP); Yoko Masuzawa, Kawasaki (JP); Masako Hagihara, Kawasaki (JP); Takashi Yamamoto, Kawasaki (JP); Hiroyuki Matsueda, Kawasaki (JP); Seiji Ohno, Kawasaki (JP); Seiji Niwa, Kawasaki (JP); Morikazu Kito, Kawasaki (JP); Akira Takahara, Kawasaki (JP); Yukitsugu Ono, Kawasaki (JP); Tomoko Takeda, Kawasaki (JP); Yuki Kajigaya, Kawasaki (JP); Hajime Koganei, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/022,874

(22) Filed: Dec. 20, 2001

(65) Prior Publication Data

US 2002/0147222 A1    Oct. 10, 2002

Related U.S. Application Data

(63) Continuation of application No. PCT/JP00/04105, filed on Jun. 22, 2000.

(30) Foreign Application Priority Data

Jun. 23, 1999 (JP) ............................... 11-177491

(51) Int. Cl.
  *A61K 31/4436* (2006.01)
  *A61K 31/4439* (2006.01)
  *A61K 31/4545* (2006.01)
  *C07D 401/04* (2006.01)
  *C07D 407/06* (2006.01)

(52) U.S. Cl. ...................... 514/318; 514/356; 546/194; 546/318; 546/321

(58) Field of Classification Search ................ 546/194, 546/318, 321, 356; 514/318, 356
See application file for complete search history.

(56) References Cited

U.S. PATENT DOCUMENTS

| | | | |
|---|---|---|---|
| 4,616,002 A | 10/1986 | Kamber et al. | |
| 5,767,131 A | 6/1998 | Gluchowski et al. | |
| 6,350,762 B1 | 2/2002 | Kito et al. | |
| 6,350,766 B1 * | 2/2002 | Uneyama et al. | 514/356 |

FOREIGN PATENT DOCUMENTS

| | | |
|---|---|---|
| EP | 0 520 200 | 12/1992 |
| EP | 0 622 364 | 11/1994 |
| EP | 0 705 819 | 4/1996 |
| EP | 0 985 667 | 3/2000 |
| EP | 1 043 314 | 10/2000 |
| JP | 60-233058 | 11/1985 |
| JP | 60233058 | 11/1985 |
| JP | 62-175462 | 8/1987 |
| JP | 08-041052 | 2/1996 |
| WO | WO 93/13128 | 7/1993 |
| WO | WO 94/22829 | 10/1994 |
| WO | WO 98/49144 | 11/1998 |
| WO | WO 99/32446 | 7/1999 |
| WO | WO 99/43658 | 9/1999 |
| WO | WO 00/24716 | 5/2000 |

OTHER PUBLICATIONS

Virginia D. Monje et al., *A New Conus Peptide Ligand for Ca Channel Subtypes*, Neuropharmacology, vol. 32, No. 11, pp. 1141-1149, 1993.

Hisayuki Uneyama et al., *Blockage of N-type $Ca^{2+}$ Current by Cilnidipine (FRC-8653) in Acutely Dissociated Rat Sympathetic Neurones*, British Journal of Pharmacology vol. 122, pp. 37-42, 1997.

Shigeo Fujii et al., *Effect of Cilnidipine, a Novel Dihydropyridine Ca++ -channel Antagonist, on N-type Ca++ Channel in Rat Dorsal Root Ganglion Neurons*, The Journal of Pharmacology and Experimental Therapeutics, vol. 280, No. 3, pp. 1184-1191, 1997.

(Continued)

*Primary Examiner*—Patricia L. Morris
(74) *Attorney, Agent, or Firm*—Oblon, Spivak, McClelland, Maier & Neustadt, P.C.

(57) ABSTRACT

Compounds having a selective N-type calcium channel antagonistic activity are provided. Dihydropyridine derivatives represented by the following formula:

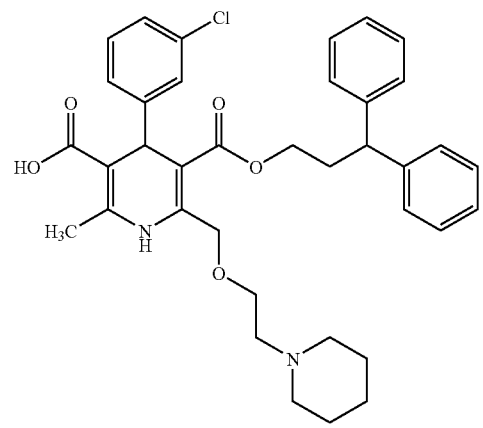

analogs thereof and pharmaceutically acceptable salts thereof have an activity of selectively inhibiting the action of N-type calcium channel, and they are used as therapeutic agents for various diseases relating to N-type calcium channel.

17 Claims, No Drawings

OTHER PUBLICATIONS

Sadanandam, Y. S., et al., *European J. of Med. Chem.,* vol. 29, pp. 975-979 (1994).

Ramesh, M., et al., *J. Med. Chem.,* vol. 41, pp. 509-514 (1998).

Brian Cox et al, *Exp. Opin. Ther. Patents,* "N-type calcium channel blockers in pain and stroke", 1998, 8(10), pp. 1237-1250.

Peter R. Dodd et al, Neurochem. Int., "Excitotoxic Mechanisms in The Pathogenesis of Dementia", 1994, vol. 25, No. 3, pp. 203-219.

Klaus W. Lange et al, Neuroscience and Biobehavioral Reviews, "Dopamine/Glutamate Interactions in Parkinson's Disease", 1997, vol. 21, No. 4, pp. 393-400.

Karl D. Kieburtz et al, Arch. Neurol., "Excitotoxicity and Dopaminergic Dysfunction in the Acquired Immunodeficiency Syndrome Dementia Complex", Dec. 1991, vol. 48, pp. 1281-1284.

Toshio Imaizumi et al, Brain Research, "The role of voltage-gated $Ca^{2+}$ channels in anoxic injury of spinal cord white matter", 1999, vol. 817, pp. 84-92.

Ken P. Madden et al, Brain Research, "Treatment with conotoxin, an 'N-type' calcium channel blocker, in neuronal hypoxic-ischemic injury", vol. 537, 1990, pp. 256-262.

D. M. White et al, Brain Research, "Effect of subcutaneous administration of calcium channel blockers on nerve injury-induced hyperalgesia", 1998, vol. 801, pp. 50-58.

Laura Basilico et al, European Journal of Pharmacology, "Influence of ω-conotoxin on morphine analgesia and withdrawal syndrome in rates", 1992, vol. 218, pp. 75-81.

R.C. Pierce et al, The Journal of Pharmacology Experimental Therapeutics, "Calcium-Mediated Second Messengers Modulate the Expression of Behavioral Sensitization to Cocaine", 1998, vol. 286, No. 3, pp. 1171-1176.

Kazuyuki Murase et al, Brain Research, "Serotonin suppresses N-methyl-D-aspartate responses in acutely isolated spinal dorsal horn neurons of the rat", vol. 525, 1990, pp. 84-91.

Dhanapalan Nagarathnam et al, J. Med. Chem., "Design and Synthesis of Novel $\alpha_{1a}$ Adrenoceptor-Selective Dihydropyridine Antagonists for the Treatment of Benign Prostatic Hyperplasia", vol. 41, 1998, pp. 5320-5333.

Wai C. Wong et al, J. Med. Chem., "Identification of a Dihydropyridine as a Potent $\alpha_{1a}$ Adrenoceptor Selective Antagonist That Inhibits Phenylephrine-Induced Contraction of the Human Prostate", vol. 41, 1998, pp. 2643-2650.

J. B. Sainani et al, Indian Journal of Chemistry, "Formation of 1,4,5,6,7,8-hexahydro-pyrido[4,3-*b*]pyridine by Hantzsch synthesis", vol. 34B, Jan. 1995, pp. 17-20.

\* cited by examiner

DIHYDROPYRIDINE DERIVATIVES

This application is a Continuation of International Application Ser. No. PCT/JP00/04105, filed on Jun. 22, 2000

BACKGROUND OF THE INVENTION

The present invention relates to new dihydropyridine derivatives and the use of the dihydropyridine derivatives as medicines. The activation of N-type calcium channel is concerned with various diseases, for example, acute stage of ischemic cerebrovascular disorders caused by cerebral infarction or intracerebral bleeding (including subarachnoidal hemorrhage); progressive neurodegenerative diseases such as Alzheimer's disease, AIDS related dementia and Parkinson's disease, dementia due to cerebrovascular disorder and ALS; neuropathy caused by head injury; various pains such as pain caused by spinal injury, diabetes or thromboangiitis obliterans, postoperative pain, migraine and visceral pain; various diseases associated with psychogenic stress such as bronchial asthma, unstable angina and irritable colitis; emotional disorder and withdrawal symptoms after addiction to drugs such as ethanol addiction withdrawal symptoms. The compounds of the present invention can inhibit the activation of the N-type calcium channel and, therefore usable as therapeutic agents for these diseases.

Calcium channels are now classified into subtypes of L, N, P, Q, R and T. Each subtype of calcium channels is organ-specifically distributed. It is known that particularly N-type calcium channel is widely distributed in pars centralis, peripheral nerves and adrenomedullary cells and participates in neuronal cell death, regulation of blood catecholamine level and control of senses such as perception.

It has been confirmed that omega conotoxin GVIA and omega conotoxin MVIIA, which are peptides selectively inhibiting N-type calcium channel, inhibit the release of excitatory neurotransmitters in the sliced brain preparation. It is also confirmed in animal experiments that they inhibit the progress of neuronal necrosis associated with cerebrovascular disorders. It is generally considered that compounds having a N-type calcium channel blocking action are clinically effective in the treatment of acute stage of ischemic cerebrovascular disorders caused by cerebral infarction or intracerebral bleeding (including subarachnoidal hemorrhage); progressive neurodegenerative diseases such as Alzheimer's disease, AIDS related dementia and Parkinson's disease, dementia due to cerebrovascular disorder and ALS; and neuropathy caused by head injury. Further, it is confirmed in animal tests that omega conotoxin MVIIA relieves a pain induced by formaldehyde, hot plate and peripheral neuropathy. Accordingly, omega conotoxin MVIIA is considered to be clinically effective against various pains such as pain caused by spinal injury, diabetes or thromboangiitis obliterans, postoperative pain, migraine and visceral pain. In addition, because omega conotoxin GVIA inhibits the release of catecholamine from cultured sympathetic ganglion cells, catecholamine secretion from canine adrenal medulla and the contraction of the isolated blood vessel by electric stimulation of the perivascular nerve, it is considered that compounds having N-type calcium channel-blocking effects are clinically effective against various diseases related to psychogenic stress such as bronchial asthma, unstable angina and irritable colitis [Neuropharmacol., 32, 1141 (1993)].

Some peptidergic and non-peptidergic compounds which selectively affect N-type calcium channels have been ever disclosed (see, for example, WO 9313128 and WO 9849144). However, none of them was actually used as a medicine. Some of the compounds which affect N-type calcium channels are also effective against various types of calcium channels of other than N-type [British Journal of Pharmacology, 122 (1) 37–42, 1997]. For example, compounds having an antagonistic effect on L-type calcium channels which are very closely related to hypotensive effect, could not be used for diseases for which N-type antagonists will be used (such as cerebral stroke, neuralgia, terminal cancer pain and pain of spinal injury). Under these circumstances, the development of a highly active antagonist selective toward N-type calcium channel has been eagerly demanded.

DISCLOSURE OF THE INVENTION

The object of the present invention is to provide new compounds having a selective antagonistic effect on N-type calcium channels.

Another object of the present invention is to provide antagonists to N-type calcium channels.

Still another object of the present invention is to provide a therapeutic agent for any of acute stage of ischemic cerebrovascular disorders caused by cerebral infarction or intracerebral bleeding, Alzheimer's disease, AIDS related dementia, Parkinson's disease, progressive neurodegenerative diseases, neuropathy caused by head injury, pain caused by thromboangiitis obliterans, postoperative pain, migraine, visceral pain, bronchial asthma, unstable angina, irritable colitis and withdrawal symptoms after addiction to drugs.

A further object of the present invention is to provide a pharmaceutical composition.

After synthesizing various dihydropyridine derivatives and examining the N-type calcium channel inhibiting effect of the newly synthesized compounds and well-known dihydropyridine derivatives for the purpose of solving the above-described problems, the inventors have found that specified, new dihydropyridine derivatives have an excellent effect of selectively antagonizing N-type calcium channels. The present invention has been completed on the basis of his finding. Namely, the inventors succeeded in reducing the antagonistic effect on L-type calcium channels which are very closely related to hypotensive effect [see, for example, a compound (IC50=250 nM) in Example 20 in WO 9849144 and compound (IC50=2.69 µM) in Example 12 in the present invention].

Namely, the present invention provides dihydropyridine derivatives of the following general formula (1) and pharmaceutically acceptable salts thereof.

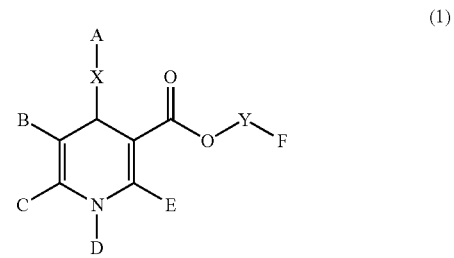

(1)

wherein A represents a group of the following general formula (2), or 1-naphthyl, 2-naphthyl, thiophene-3-yl, thiophene-2-yl, furan-3-yl, furan-2-yl, pyridine-4-yl, pyridine-3-yl, pyridine-2-yl, indole-2-yl or indole-3-yl group:

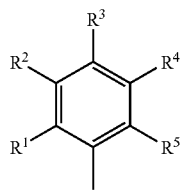
(2)

wherein $R^1$, $R^2$, $R^3$, $R^4$ and $R^5$ may be the same or different from each other and each represent hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl group, an aryl-lower alkoxyl group or an aroyl group, B represents cyano group, nitro group, carboxyl group, acetyl group or a group of the following general formula (3):

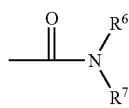
(3)

wherein $R^6$ and $R^7$ may be the same or different from each other and each represent hydrogen atom, a lower alkyl group, an amino-lower alkyl group, an amino-lower alkyl group substituted with one or two lower alkyl groups, a carboxy-lower alkyl group, a hydroxy-lower alkyl group, a lower cycloalkyl group, an amino-lower alkenyl group, a carboxy-lower alkenyl group, a hydroxy-lower alkenyl group, an aryl group, a heteroaryl group, an aryl-lower alkyl group, a heteroaryl-lower alkyl group, a lower alkyl group substituted with a cyclic alkyl group which may have a hetero atom in the ring, an aryl-lower alkenyl group or an aryl-lower alkyloxycarbonyl-lower alkyl group, or $R^6$ and $R^7$ may together form a ring which may contain a hetero atom and when the hetero atom is nitrogen atom, it may have a substituent, C and E may be the same or different from each other and each represent hydrogen atom, a lower alkyl group, dimethoxymethyl group, cyano group, a hydroxy-lower alkyl group, a carboxy-lower alkyl group, a halogeno-lower alkyl group, an amino-lower alkyl group, in which the amino group may be substituted with one or two of a lower alkyl group, a lower cycloalkyl group, an aryl group or an aryl-lower alkyl group, an azido-lower alkyl group, an aryl group, a heteroaryl group, an aryl-lower alkyl group, a heteroaryl-lower alkyl group, a lower alkyl group substituted with a cyclic alkyl group which may contain a hetero atom in the ring, or a carbamoyl-lower alkyl group, in which the carbamoyl group may be substituted with one or two of a lower alkyl group, a lower cycloalkyl group, an aryl group or an aryl-lower alkyl group, D represents a hydrogen atom, a lower alkyl group, a hydroxy-lower alkyl group or an aryl-lower alkyl group, F represents a group represented by any of the following general formulae (4) to (8):

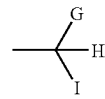
(4)

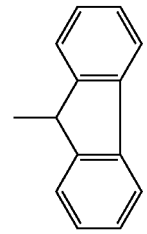
(5)

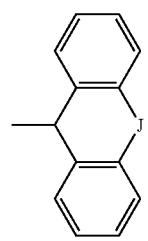
(6)

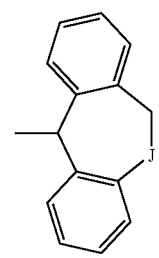
(7)

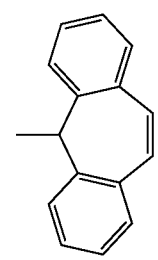
(8)

wherein G and H may be the same or different from each other and each represent phenyl group, benzyl group, 1-naphthyl group, 2-naphthyl group, thiophene-3-yl group, thiophene-2-yl group, furan-3-yl group, furan-2-yl group, pyridine-4-yl group, pyridine-3-yl group, pyridine-2-yl group, pyridine-4-ylmethyl group, pyridine-3-ylmethyl group or pyridine-2-ylmethyl group, I represents hydrogen atom or hydroxyl group, J represents —$CH_2$—, —NH—, oxygen atom or sulfur atom, and one or two atoms surrounding condensed rings (5) to (8) may be nitrogen atoms, X represents an interatomic bond, —$CH_2$—, —$CH_2CH_2$—, —CH=CH— or —C≡C—, and Y represents an alkyl group having 1 to 7 carbon atoms, which may contain a hetero atom or cyclopropane ring in the chain, or an alkenyl group, which may contain a hetero atom or cyclopropane ring in the chain.

The present invention also provides an N-type calcium channel antagonist containing a dihydropyridine derivative of above general formula (1) or a pharmaceutically acceptable salt thereof as an active ingredient.

The present invention further provides a therapeutic agent containing the dihydropyridine derivative represented by the above general formula (1) or a pharmaceutically acceptable salt thereof as the active ingredient, for any of acute stage of ischemic cerebrovascular disorders caused by cerebral infarction or intracerebral bleeding, Alzheimer's disease, AIDS related dementia, Parkinson's disease, progressive neurodegenerative diseases, neuropathy caused by head injury, pain caused by thromboangiitis obliterans, postoperative pain, migraine, visceral pain, bronchial asthma, unstable angina, irritable colitis and withdrawal symptoms after addiction to drugs.

The present invention also provides a pharmaceutical composition containing the dihydropyridine derivative represented by the above general formula (1) or a pharmaceutically acceptable salt thereof and a carrier and/or a diluent.

BEST MODE FOR CARRYING OUT THE INVENTION

The term "lower" herein indicates that the group has 1 to 7 carbon atoms, preferably 1 to 6 carbon atoms. Alkyl groups themselves and also alkyl groups in alkoxyl groups, alkenyl groups, alkylamino groups, alkylthio groups and alkanoyl groups may be either linear or branched. Examples of these alkyl groups are methyl group, ethyl group, propyl group, isopropyl group, butyl group, secondary and tertiary butyl groups, pentyl group and hexyl group. Among them, those having 1 to 3 carbon atoms are preferred. The lower cycloalkyl groups indicate 3 to 8-membered rings, preferably 5 to 7-membered rings. The lower cycloalkyl groups may contain a hetero atom. When the hetero atom is nitrogen atom, it may have a substituent such as benzyl group. The aryl-lower alkyl groups include, for example, benzyl group. When the aryl-lower alkyl groups contain a hetero atom, they include, for example, 2-benzyloxyethoxymethyl group, 2-phenylethoxymethyl group and benzyloxyethyl group. The aryl-lower alkoxyl groups include, for example, benzyloxy group. The heteroaryl-lower alkyl groups include, for example, pyridylmethyl group. When they contain a hetero atom in the chain hereof, they include, for example, 2-(2-pyridyl)ethoxymethyl group, 2-(3-pyridyl)ethoxymethyl group and 2-(4-pyridyl)ethoxymethyl group. The lower alkyl groups substituted with a cyclic alkyl group include, for example, cyclohexylmethyl group. When they contain a hetero atom in the ring, they include, for example, piperidinoethoxymethyl group, hexamethyleneimino-ethoxymethyl group and cyclohexylethoxymethyl group.

The halogen atoms include fluorine, chlorine, bromine and iodine atoms. In the present specification, the aryl groups are both substituted and unsubstituted aryl groups. They are preferably phenyl group and substituted phenyl group, and the substituents are particularly preferably halogens, alkyl groups and alkoxyl groups. The heteroaryl groups are substituted or unsubstituted heteroaryl groups such as, preferably, pyridyl group, furyl group, substituted pyridyl groups and substituted furyl groups. Halogens, alkyl groups and alkoxyl groups are particularly preferred as the substituents.

1-Naphthyl group, 2-naphthyl group, indole-2-yl group and indole-3-yl group represented by A in the above general formula (1) are either unsubstituted or substituted. The substituents are those listed above for $R^1$ to $R^5$.

Thiophene-3-yl group, thiophene-2-yl group, furan-3-yl group, furan-2-yl group, pyridine-4-yl group, pyridine-3-yl group and pyridine-2-yl group represented by A are also either unsubstituted or substituted. When two or more substituents are contained therein, they may form a ring together. The substituents are those described above with reference to 1-naphthyl group or the like. The rings formed by those groups include benzothiophene, benzofuran, etc.

A in the general formula (1) is preferably that represented by the general formula (2) wherein $R^1$, $R^2$, $R^3$, $R^4$ and $R^5$ each represent nitro group or cyano group, particularly $R^1$, $R^3$, $R^4$ and $R^5$ each represent hydrogen atom and $R^2$ represents a halogen atom or carboxyl group.

The rings which can be formed by $R^6$ and $R^7$ together in the group of general formula (3) for B in general formula (1) include piperazine, piperidine, pyrrolidine, hexamethyleneimine, etc. Carbon atoms or nitrogen atom as the hetero atom in the formed ring may have carboxyl group, in which the hydroxyl group may be substituted with benzyl group, or benzyl group. When the ring is piperazine ring, hydrogen atom bonded to the nitrogen atom which is free from the amido bond of the ring may be replaced with benzyl group, tert-butoxycarbonyl group, phenyl group, pyridinyl group, diphenyl group or the like.

B in the above general formula (1) is preferably carboxyl group, cyano group or a group of the above general formula (3). B is particularly preferably carboxyl group or a group represented by the general formula (3) wherein one of $R^6$ and $R^7$ is hydrogen atom and the other is a carboxy-lower alkyl group, hydroxy-lower alkyl group or aryl-lower alkyl group, or both $R^6$ and $R^7$ represent a lower alkyl group or $R^6$ and $R^7$ together form a ring.

The lower alkyl groups, hydroxy-lower alkyl groups, carboxy-lower alkyl groups, halogeno-lower alkyl groups (such as trifluoromethyl group), amino-lower alkyl groups, azido-lower alkyl groups, aryl-lower alkyl groups, heteroaryl-lower alkyl groups, lower alkyl groups substituted with a cyclic alkyl group and carbamoyl-lower alkyl groups in C or E in the above general formula (1) may contain a hetero atom in their chains. The hetero atoms include, for example, oxygen, nitrogen and sulfur atoms. The groups containing such a hetero atom in the chain include, for example, 2-hydroxyethoxymethyl group, methoxymethyl group, dimethoxymethyl group, methoxyethyl group, aminoethoxymethyl group, azidoethoxymethyl group, methylthiomethyl group, 2-piperidinoethoxymethyl group, pyrrolidinyl-ethoxymethyl group, morpholinylethoxymethyl group, pyridinylethoxymethyl group, piperidinylethoxymethyl group, which may be substituted with benzyloxycarbonyl group, azidoethoxymethyl group, aminoethoxymethyl group, carboxyethoxymethyl group, dimethyldioxolanylmethoxymethyl group, dimethyldioxolanylmethoxyethoxymethyl group and dihydroxypropoxymethyl group. C is preferably methyl group, ethyl group or 2-piperidinoethoxymethyl group. C is also preferably pyrrolidinylethoxymethyl group, morpholinylethoxymethyl group, pyridinylethoxymethyl group or trifluoromethyl group. E is preferably methyl group, ethyl group, dimethoxymethyl group, methoxymethyl group, 2-piperidinoethoxymethyl group, 2-hexamethyleneiminoethoxymethyl group, 2-hydroxyethoxymethyl group, 2-benzyloxyethoxymethyl group or 2-(2-pyridyl)ethoxymethyl group. E is also preferably pyrrolidinylethoxymethyl group, hexaoxymethyl group, pyridinylethoxymethyl group, morpholinylethoxymethyl group, piperidinyl-ethoxymethyl group, which may be substituted with benzyloxycarbonyl group, azidoethoxymethyl group, aminoethoxymethyl group, carboxyethoxymethyl group, dimethyldioxolanylmethoxymethyl group, dimethyldioxolanyl-methoxyethoxymethyl group, trifluoromethyl group or 2,3-dihydroxy-propoxymethyl group.

D in the above general formula (1) is preferably hydrogen atom or a hydroxy-lower alkyl group. Hydrogen atom is particularly preferred.

One or two groups surrounding the condensed rings of the general formulae (5) to (8) represented by F in the above general formula (1) may be nitrogen atoms. The general formulae (4) to (8) represent unsubstituted or substituted groups. The substituents are those described above with reference to $R^1$ to $R^5$.

F is preferably a group of the above general formula (4) wherein G and H may be the same or different from each other and they each represent phenyl group, benzyl group, pyridine-4-yl group, pyridine-3-yl group, pyridine-2-yl group, pyridine-4-ylmethyl group, pyridine-3-ylmethyl group or pyridine-2-ylmethyl group, and I preferably represents hydrogen atom or hydroxyl group. It is particularly preferred that G and H each represent phenyl group and I represents hydrogen atom.

X in the above general formula (1) represent an interatomic bond, —CH$_2$—, —CH$_2$CH$_2$—, —CH=CH— or —C≡C—. The interatomic bond or —CH$_2$— is preferred. The interatomic bond is particularly preferred.

Y in the above general formula (1) represents an alkyl group having 1 to 7 carbon atoms, which may contain a hetero atom or cyclopropane ring in the chain, or an alkenyl group, which may contain a hetero atom or cyclopropane ring in the chain. The expression that the chain may contain cyclopropane indicates that cyclopropane ring may be formed at the bonding part between Y and F. Y is preferably an alkyl group having 2 to 4 carbon atoms, particularly an alkyl group having 2 or 3 carbon atoms.

It is preferred that in general formula (1), A represents a group of general formula (2), B represents carboxyl group, cyano group or a group of general formula (3), D represents hydrogen atom, F represents a group of general formula (4) in which G and H each represent phenyl group, X represents the interatomic bond and Y represents an alkyl group having 2 or 3 carbon atoms. It is particularly preferred that B represents carboxyl group.

It is also preferred that in general formula (1), A represents a group of general formula (2), B represents carboxyl group, cyano group or a group of general formula (3), D represents hydrogen atom, C and E may be the same or different from each other, and they each represent a lower alkyl group, a lower alkyl group substituted with a cycloalkyl group which may contain a hetero atom in the ring, a hydroxy-lower alkyl group, an aryl-lower alkyl group or a heteroaryl-lower alkyl group, F represents a group of general formula (4) in which G and H each represent phenyl group, X represents the interatomic bond and Y represents an alkyl group having 2 or 3 carbon atoms.

It is further preferred that in general formula (1), A represents a group of general formula (2) wherein $R^1$, $R^3$, $R^4$ and $R^5$ each represent hydrogen atom and $R^2$ represents chlorine atom, bromine atom, iodine atom, nitro group or cyano group, B represents carboxyl group, cyano group or a group of general formula (3), C and E may be the same or different from each other, and they each represent methyl group, ethyl group, a lower alkyl group substituted with a cycloalkyl group which may contain a hetero atom in the ring, a hydroxy-lower alkyl group, an aryl-lower alkyl group or a heteroaryl-lower alkyl group, D represents hydrogen atom, F represents a group of general formula (4) in which G and H each represent phenyl group and I represents hydrogen atom, X represents the interatomic bond and Y represents an alkyl group having 2 or 3 carbon atoms. It is particularly preferred that B represents carboxyl group.

It is also preferred that in general formula (1), A represents a group of general formula (2) wherein $R^1$, $R^3$, $R^4$ and $R^5$ each represent hydrogen atom and $R^2$ represents chlorine atom, bromine atom, iodine atom or nitro group, B represents carboxyl group, cyano group or a group of general formula (3), C represents methyl group, ethyl group or 2-piperidinoethoxymethyl group, D represents hydrogen atom, E represents methyl group, ethyl group, dimethoxymethyl group, 2-piperidinoethoxymethyl group, 2-hexamethylene-iminoethoxymethyl group, methoxymethyl group, 2-benzyloxyethoxymethyl group, 2-(2-pyridyl)ethoxymethyl group or 2-hydroxyethoxymethyl group, F represents a group of general formula (4) in which G and H each represent phenyl group and I represents hydrogen atom, X represents the interatomic bond and Y represents an alkyl group having 2 or 3 carbon atoms. It is particularly preferred that B represents carboxyl group.

It is also preferred that in general formula (1), A represents a group of general formula (2), B represents carboxyl group, cyano group or a group of general formula (3), C represents hydrogen atom, a lower alkyl group, dimethoxymethyl group, cyano group, a hydroxy-lower alkyl group, a halogeno-lower alkyl group, an amino-lower alkyl group (in which the amino group may be substituted with one or two of a lower alkyl group, a lower cycloalkyl group, an aryl group or an aryl-lower alkyl group), an azido-lower alkyl group, an aryl group, a heteroaryl group, an aryl-lower alkyl group, a heteroaryl-lower alkyl group, a lower alkyl group substituted with a cyclic alkyl group (which may contain a hetero atom in the ring) or a carbamoyl-lower alkyl group (in which the carbamoyl group may be substituted with one or two of a lower alkyl group, a lower cycloalkyl group, an aryl group or an aryl-lower alkyl group), D represents hydrogen atom, E represents methyl group, ethyl group, a lower alkoxymethyl group, a hydroxy-lower alkoxymethyl group, an aryl-lower alkoxymethyl group, a heteroaryl-lower alkoxymethyl group or a lower alkoxymethyl group substituted with a cycloalkyl group (which may contain a hetero atom in the ring), X represents the interatomic bond and Y represents an alkyl group having 2 or 3 carbon atoms. It is particularly preferred that B represents carboxyl group.

Particularly preferred are dihydropyridine derivatives of general formula (1) and pharmaceutically acceptable salts thereof, wherein A represents a group of general formula (2) wherein $R^1$, $R^3$, $R^4$ and $R^5$ each represent hydrogen atom and $R^2$ represents chlorine atom, bromine atom, iodine atom or nitro group, B represents carboxyl group or a group of general formula (3), C represents methyl group, ethyl group or 2-piperidinoethoxymethyl group, E represents methyl group, ethyl group, dimethoxymethyl group, 2-piperidinoethoxymethyl group, 2-hexamethyleneiminoethoxymethyl group, methoxymethyl group, 2-benzyloxyethoxymethyl group, 2-hydroxyethoxymethyl group or 2-(2-pyridyl)ethoxymethyl group, D represents hydrogen atom and X represents the interatomic bond.

Dihydropyridine derivatives (1) of the present invention can be produced by processes described below:

For example, dihydropyridine derivatives (1-1) wherein B represents carboxyl group, C and E each represent methyl group and D represents hydrogen atom can be produced by the following reaction scheme:

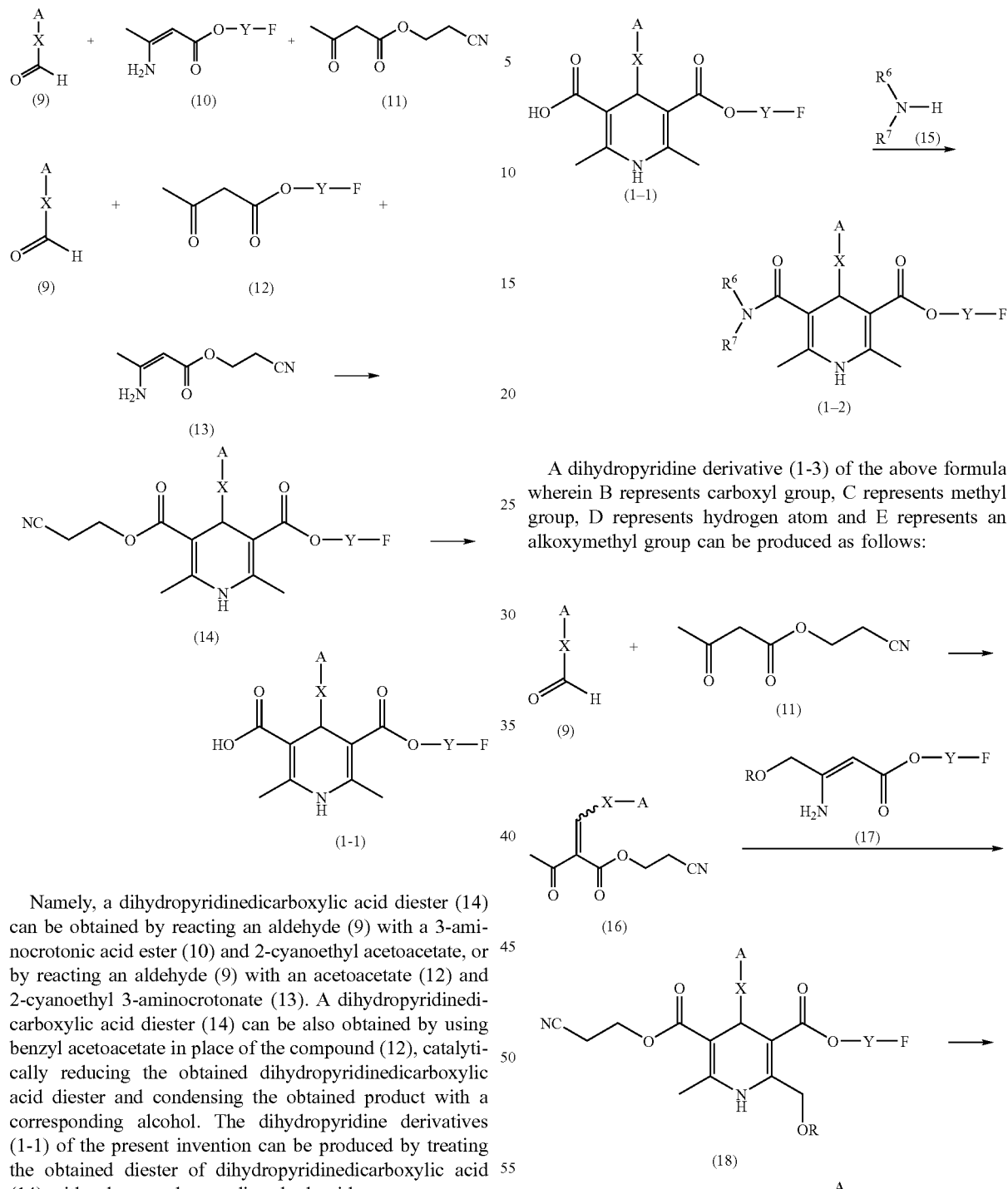

Namely, a dihydropyridinedicarboxylic acid diester (14) can be obtained by reacting an aldehyde (9) with a 3-aminocrotonic acid ester (10) and 2-cyanoethyl acetoacetate, or by reacting an aldehyde (9) with an acetoacetate (12) and 2-cyanoethyl 3-aminocrotonate (13). A dihydropyridinedicarboxylic acid diester (14) can be also obtained by using benzyl acetoacetate in place of the compound (12), catalytically reducing the obtained dihydropyridinedicarboxylic acid diester and condensing the obtained product with a corresponding alcohol. The dihydropyridine derivatives (1-1) of the present invention can be produced by treating the obtained diester of dihydropyridinedicarboxylic acid (14) with a base such as sodium hydroxide.

In another process, dihydropyridine derivatives (1-2) of the present invention can be produced by condensing the dihydropyridine derivative (1-1) synthesized by the above-described process with an amine (15). When the amine (15) has a protecting group, the dihydropyridine derivative (1-2) is subjected to, if necessary, a protecting group-removing reaction. When $R^6$ and $R^7$ together form a ring containing nitrogen atom having a substituent, the obtained dihydropyridine derivative (1-2) is subjected to, if necessary, the protecting group-removing reaction.

A dihydropyridine derivative (1-3) of the above formula wherein B represents carboxyl group, C represents methyl group, D represents hydrogen atom and E represents an alkoxymethyl group can be produced as follows:

Namely, a compound (16) is obtained by Knoevenagel reaction of an aldehyde (9) and a 2-cyanoethyl acetoacetate (11). Then the compound (16) is reacted with an ester of 3-amino-4-alkoxycrotonic acid (17) to obtain a dihydropyridine derivative (18). This product is treated with a base such as sodium hydroxide to obtain a dihydropyridine derivative (1-3) of the present invention.

The dihydropyridine derivative (1-3) can be produced also by the following reaction scheme:

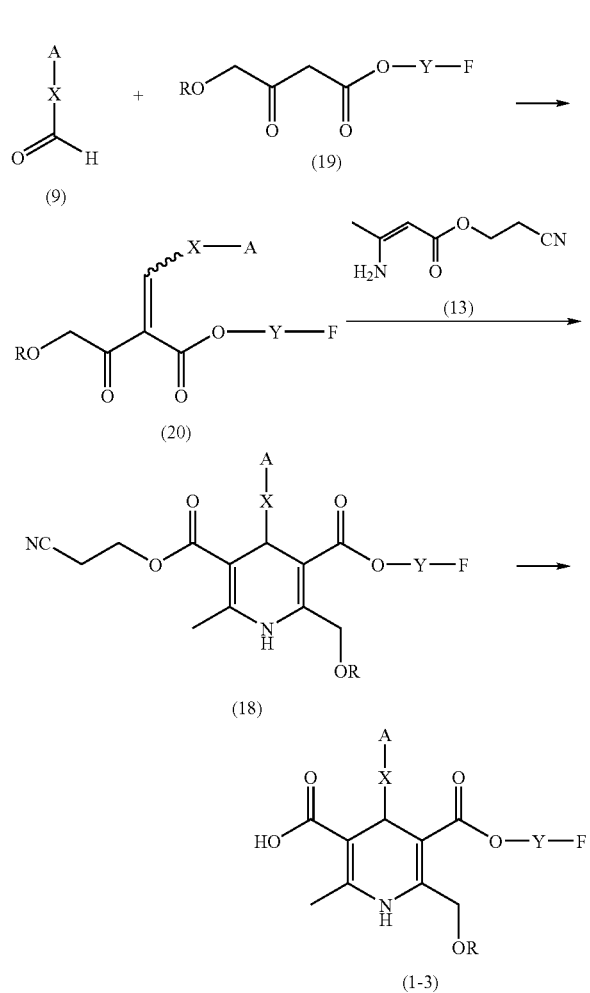

Namely, a compound (20) is obtained by Knoevenagel reaction of an aldehyde (9) and a 4-alkoxy-3-oxobutanoic acid ester (19). Then the compound (20) is reacted with 2-cyanoethyl 3-aminocrotonate (13) to obtain a dihydropyridine derivative (18). This product is treated with a base such as sodium hydroxide to obtain a dihydropyridine derivative (1-3) of the present invention.

When the alkoxymethyl has a protecting group for an amine or an alcohol in the above-described two processes, the protecting group is removed from compound (18) and then compound (1-3) is produced, or compound (1-3) is produced and then the protecting group is removed by the reaction. Compound (1-3) having an amine in the alkoxymethyl can be produced by reacting a derivative (18) wherein R represents a halogenated alkyl group with a corresponding amine. When it is a primary amino group, a derivative (18) wherein R represents a halogenated alkyl group is reacted with sodium azide or the like to form an azide, which is then converted into compound (1-3) and this compound is catalytically reduced.

A dihydropyridine derivative (1-4) of the above formula wherein B represents carboxyl group, C represents an alkoxymethyl group, D represents hydrogen atom and E represents methyl group can be produced as follows:

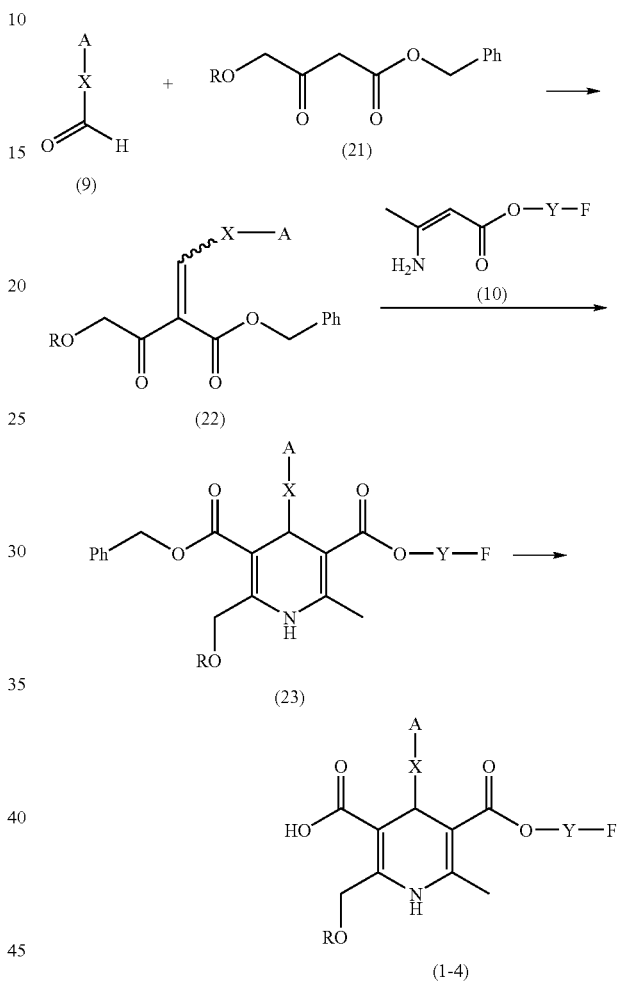

Namely, a compound (22) is obtained by Knoevenagel reaction of an aldehyde (9) and a benzyl 4-alkoxy-3-oxobutanoate (21). Then the compound (22) is reacted with an ester of 3-aminocrotonic acid (10) to obtain a dihydropyridine derivative (23). This product is catalytically reduced to obtain a dihydropyridine derivative (1-4) of the present invention.

The dihydropyridine derivative (1-4) of the present invention can also be produced as follows:

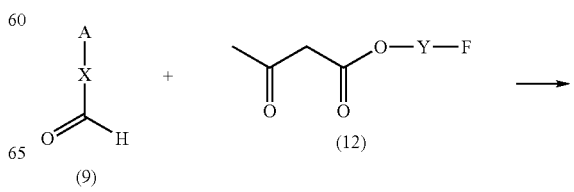

A dihydropyridine derivative (1-5) of the above formula wherein B represents cyano group, C and E each represent methyl group and D represents hydrogen atom can be produced as follows:

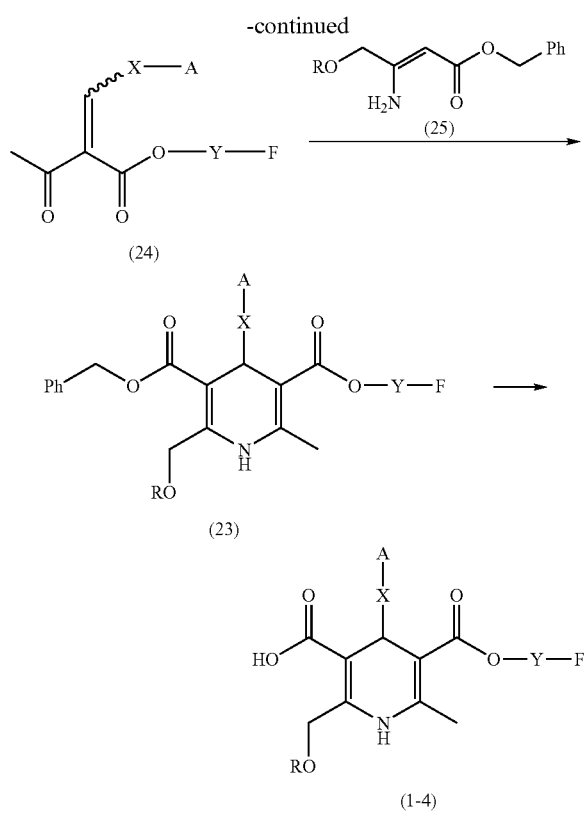

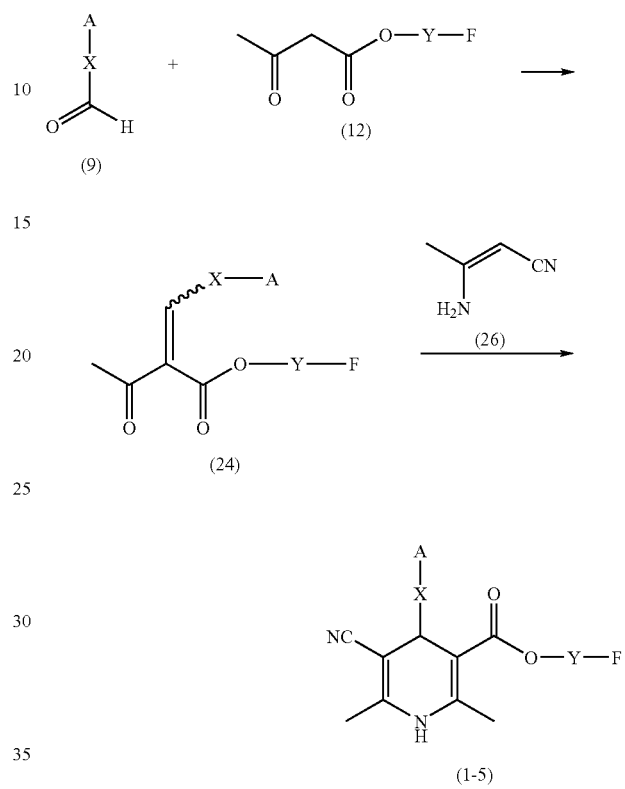

Namely, a compound (24) is obtained by Knoevenagel reaction of an aldehyde (9) and an acetoacetic acid ester (12). Then the compound (24) is reacted with a benzyl 3-amino-4-alkoxycrotonate (25) to obtain a dihydropyridine derivative (23). This product is, for example, catalytically reduced to obtain a dihydropyridine derivative (1-4) of the present invention.

When the alkoxymethyl has a protecting group for an amine or an alcohol in the above-described two processes, the protecting group is removed from compound (23) and then compound (1-4) is produced, or compound (1-4) is produced and then the protecting group is removed by the reaction. Compound (1-4) having an amine in the alkoxymethyl can be produced by reacting a derivative (23) wherein R represents a halogenated alkyl group with a corresponding amine. When it is a primary amino group, a derivative (23) wherein R represents a halogenated alkyl group is reacted with sodium azide or the like to form an azide, which is then catalytically reduced to obtain compound (1-4).

Namely, a dihydropyridine derivative (24) is obtained by Knoevenagel reaction of an aldehyde (9) and an acetoacetic acid ester (12). Then the compound (24) is reacted with an aminocrotonitrile (26) to obtain a dihydropyridine derivative (1-5).

The dihydropyridine derivative (1-5) can be produced also by reacting an aldehyde (9), an acetoacetic acid ester (12) and 3-aminocrotonitrile (26).

A dihydropyridine derivative (1-6) of the above formula wherein B represents carboxyl group, C represents methyl group, D represents hydrogen atom and E represents trifluoromethyl group can be produced as follows:

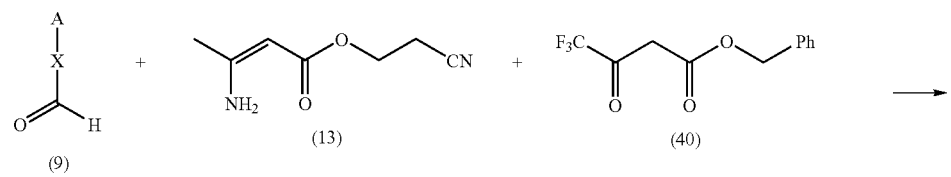

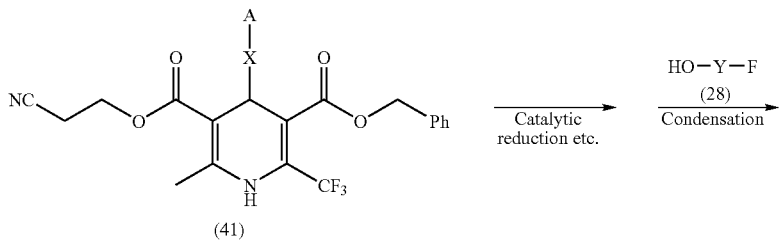

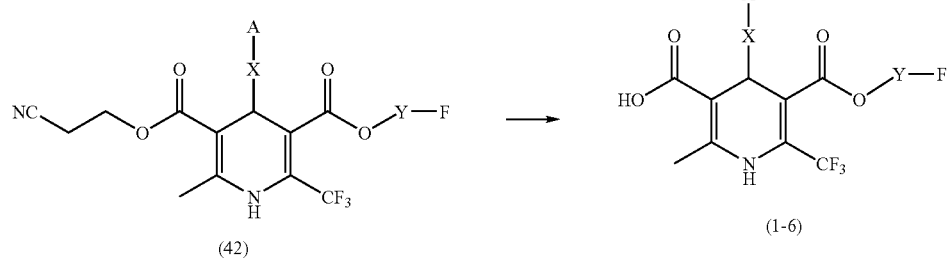

Namely, a dihydropyridinedicarboxylic acid diester (41) can be obtained by reacting an aldehyde (9), 2-cyanoethyl 3-aminocrotonate (13) and benzyl 4,4,4-trifluoroacetoacetate (40). This product is catalytically reduced and then the reduction product is condensed with an alcohol (28) to obtain a dihydropyridine derivative (42). This product is treated with a base such as sodium hydroxide to obtain a dihydropyridine derivative (1-6) of the present invention.

A dihydropyridine derivative (1-7) of the above formula wherein B represents carboxyl group, C represents trifluoromethyl group, D represents hydrogen atom and E represents methyl group can be produced as follows:

Namely, a dihydropyridinedicarboxylic acid diester (45) can be obtained by reacting an aldehyde (9), benzyl 3-aminocrotonate (43) and 2-cyanoethyl 4,4,4-trifluoroacetoacetate (44). This product is, for example, catalytically reduced and then the reduction product is condensed with a corresponding alcohol (28) to obtain a dihydropyridine derivative (46). This product is treated with a base such as sodium hydroxide to obtain a dihydropyridine derivative (1-7) of the present invention.

The acetoacetic acid esters (12) used as the starting material can be produced according to, for example, the following process, if they are not well-known:

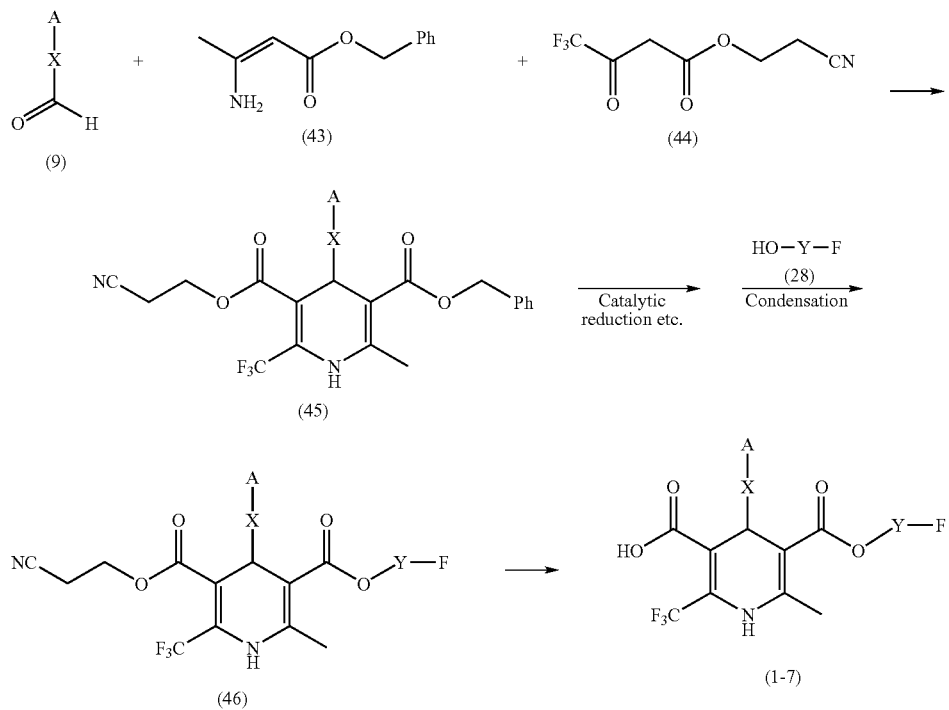

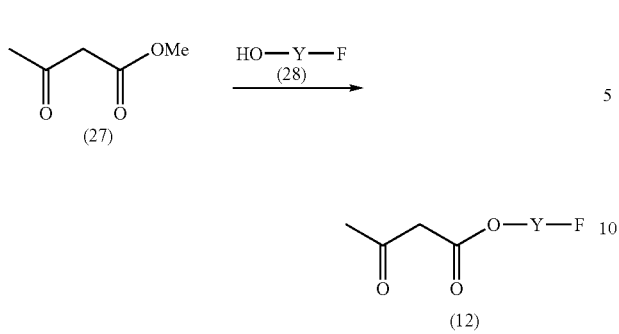

For example, methyl acetoacetate (27) and an alcohol (28) are heated and thereby transesterified to obtain the acetoacetic acid ester (12).

In another method, an alcohol (28), a diketene (29) and a proper base are heated together to obtain an acetoacetic acid ester (12) as follows:

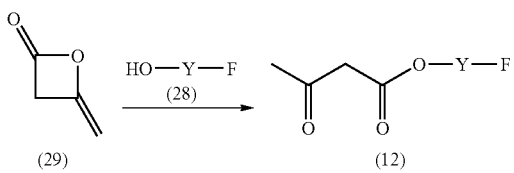

The 3-aminocrotonic acid esters (30) used as the starting material can be produced according to, for example, the following process, if they are not well-known:

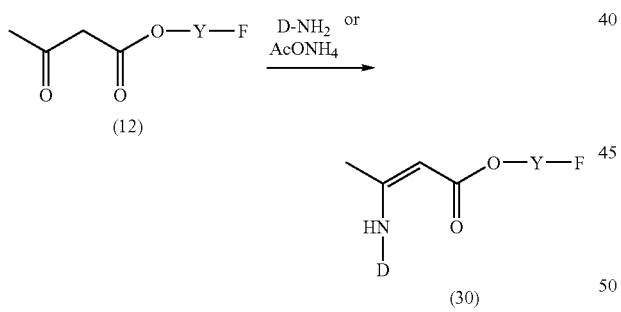

Namely, an acetoacetic acid ester (12) is reacted with an amine or ammonium acetate to obtain the intended compound.

The 4-alkoxy-3-oxobutanoic acid esters (19) used as the starting material can be produced according to, for example, the following process, if they are not well-known:

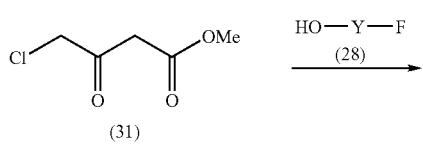

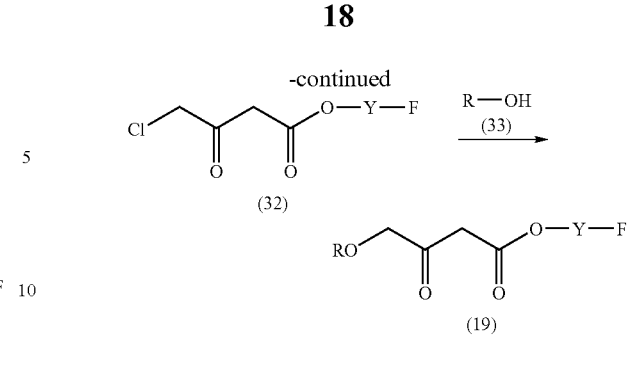

For example, a chloroacetoacetic acid ester (32) can be obtained by heating ethyl chloroacetoacetate (31) and an alcohol (28) together to conduct the transesterification. A 4-alkoxy-3-oxobutanoic acid ester (19) can be obtained by reacting the ester (32) with an alcohol (33) in the presence of sodium hydride.

The 3-amino-4-alkoxycrotonic acid esters (34) used as the starting material can be produced according to, for example, the following process, if they are not well-known:

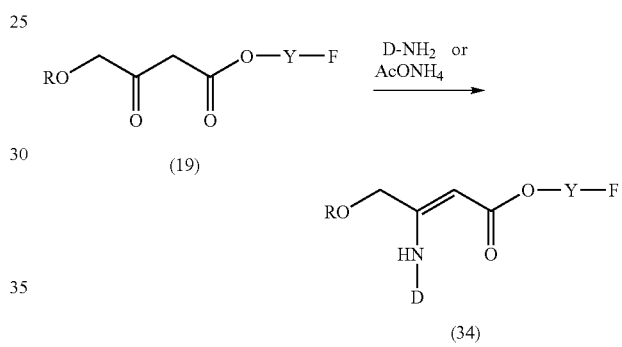

Namely, a 4-alkoxy-3-oxobutanoic acid ester (19) is reacted with an amine or ammonium acetate to obtain 3-amino-4-alkoxycrotonic acid ester (34).

The 2-cyanoethyl 3-aminocrotonates (35) used as the starting material can be produced according to, for example, the following process, if they are not well-known:

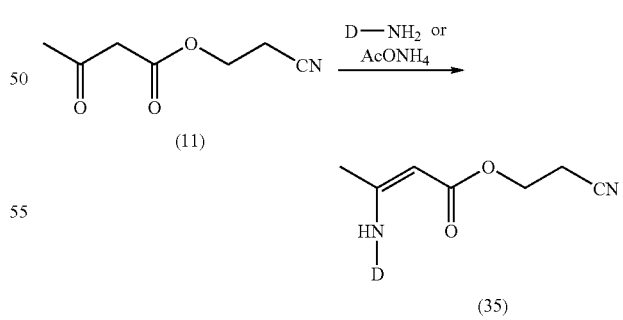

Namely, 2-cyanoethyl acetoacetate (11) is reacted with an amine or ammonium acetate to obtain 2-cyanoethyl 3-aminocrotonate (35).

The acyl acetates (39) used as the starting material can be produced according to, for example, the following process,

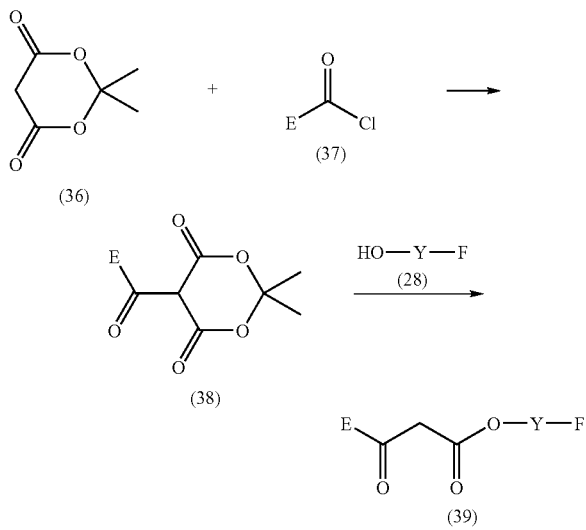

Namely, Meldrum's acid (36) is reacted with an acyl chloride (37) in the presence of a suitable base to obtain a compound (38), which is then reacted with an alcohol (28) to obtain an acylacetic acid ester (39).

Optical isomers of 1,4-dihydropyridines represented by general formula (1) are possible because they contain an asymmetric carbon bond. The compounds of the present invention also include those optical isomers.

When the compounds of general formula (1) can form salts thereof, the salts are pharmaceutically acceptable ones such as ammonium salts, salts thereof with alkali metals, e. g. sodium and potassium, salts thereof with alkaline earth metals, e. g. calcium and magnesium, salts thereof with aluminum and zinc, salts thereof with organic amines, e. g. morpholine and piperidine, and salts thereof with basic amino acids, e. g. arginine and lysine.

The compounds of general formula (1) and salts thereof are administered as they are or in the form of various medicinal compositions to patients. The dosage forms of the medicinal compositions are, for example, tablets, powders, pills, granules, capsules, suppositories, solutions, sugar-coated tablets and depots. They can be prepared with ordinary preparation assistants by an ordinary method.

For example, the tablets are prepared by mixing the dihydropyridine derivative, the active ingredient of the present invention, with any of known adjuvants such as inert diluents, e. g. lactose, calcium carbonate and calcium phosphate; binders, e. g. acacia, corn starch and gelatin; extending agents, e. g. alginic acid, corn starch and pre-gelatinized starch; sweetening agents, e. g. sucrose, lactose and saccharin; corrigents, e. g. peppermint, and cherry; and lubricants, e. g. magnesium stearate, talc and carboxymethyl cellulose.

The N-type calcium channel inhibitor containing one of the compounds of above general formula (1) or one of salts thereof as active ingredient is usable as a therapeutic agent for various diseases, for example, acute stage of ischemic cerebrovascular disorders caused by cerebral infarction or intracerebral bleeding (including subarachnoidal hemorrhage); progressive neurodegenerative diseases such as Alzheimer's disease, AIDS related dementia and Parkinson's disease, dementia due to cerebrovascular disorder and ALS; neuropathy caused by head injury; various pains such as pain caused by spinal injury, diabetes or thromboangiitis obliterans, postoperative pain, migraine and visceral pain; various diseases associated with psychogenic stress such as bronchial asthma, unstable angina and irritable colitis; emotional disorder withdrawal symptoms after addiction to drugs such as ethanol addiction withdrawal symptoms.

The dose of the compound of general formula (1) or salt thereof used for the above-described purpose varies depending on the intended therapeutic effect, administration method, period of the treatment, and age and body weight of the patient. The dose is usually 1 μg to 5 g a day for adults in the oral administration, and 0.01 μg to 1 g a day for adults in the parenteral administration.

The following Examples will further illustrate the present invention, which are only preferred embodiments of the invention and which by no means limit the invention.

EXAMPLE 1

Synthesis of mono(3,3-diphenylpropane-1-yl)4-(3-chlorophenyl)-2,6-dimethyl-1,4-dihydropyridine-3, 5-dicarboxylate 1) Synthesis of 3-(2-cyanoethyl)5-(3,3-diphenylpropane-1-yl)4-(3-chlorophenyl)-2,6-dimethyl-1,4-dihydropyridine-3, 5-dicarboxylate:

747 mg (2.52 mmol) of 3,3-diphenylpropyl acetoacetate, 389 mg (2.52 mmol) of 2-cyanoethyl 3-aminocrotonate and 0.285 ml (2.52 mmol) of 3-chlorobenzaldehyde were heated at 80° C. under stirring in 20 ml of 2-propanol for two nights. 2-Propanol was evaporated under reduced pressure, and the residue was purified by the silica gel chromatography (hexane/ethyl acetate: 2/1) to obtain the title compound.

Yield: 814 mg (1.47 mmol) (58.3%) MS (ESI, m/z) 553 (M–H)– 1H-NMR (CDCl3): 2.28–2.42 (2H, m), 2.35 (6H, s), 2.64 (2H, t), 3.91 (1H, t), 3.95–4.02 (2H, m), 4.22–4.39 (2H, m), 5.00 (1H, s), 5.73 (1H, s), 7.08–7.30 (14H, m)

2) Synthesis of mono(3,3-diphenylpropane-1-yl)4-(3-chlorophenyl)-2,6-dimethyl-1,4-dihydropyridine-3,5-dicarboxylate:

808 mg (1.46 mmol) of 3-(2-cyanoethyl)5-(3,3-diphenylpropane-1-yl)4-(3-chlorophenyl)-2,6-dimethyl-1,4-dihydropyridine-3,5-dicarboxylate was dissolved in 15 ml of methanol. 3 ml of 1 N aqueous sodium hydroxide solution was added to the obtained solution, and they were stirred at room temperature for 2 hours. 2 N hydrochloric acid was added to the obtained mixture, and then methanol was evaporated under reduced pressure. Water was added to the residue, and the resultant solid was taken by the filtration, washed with water and then with a mixture of hexane and ethyl acetate (3:1), and dried under reduced pressure to obtain the title compound.

Yield: 398 mg (0.79 mmol) (54.3%) MS (ESI, m/z) 500 (M–H)– 1H-NMR (DMSO-d6): 2.24–2.34 (2H, m), 2.24 (3H, s), 2.29 (3H, s), 3.81 (2H, t), 3.87 (1H, t), 4.95 (1H, s), 7.09–7.33 (14H, m), 8.85 (1H, s)

EXAMPLE 2

Synthesis of mono(2,2-diphenylethyl)4-(3-chlorophenyl)-2,6-dimethyl-1,4-dihydropyridine-3,5-dicarboxylate 1) Synthesis of 2,2-diphenylethyl acetoacetate:

500 mg (2.52 mmol) of 2,2-diphenylethanol was dissolved in 10 ml of toluene. 382 mg (3.78 mmol) of triethylamine was added to the obtained solution, and they were stirred at room temperature for 1 hour. 386 mg (3.03 mmol) of diketene was added to the obtained mixture under cooling with ice, and then they were stirred under heating at 100° C. for 2 hours. After the addition of saturated aqueous sodium hydrogencarbonate solution followed by the extraction with ethyl acetate, the organic layer was dried over anhydrous sodium sulfate and concentrated under reduced pressure to obtain the unpurified title compound.

Yield: 831 mg (2.94 mmol) (quantitative yield) MS (ESI, m/z) 281 (M–H)– 1H-NMR (CDCl3): 2.04 (3H, s), 3.34 (2H, s), 4.38 (1H, t), 4.70 (2H, d), 7.18–7.38 (10H, m)

2) Synthesis of 3-(2-cyanoethyl)5-(2,2-diphenylethyl)4-(3-chlorophenyl)-2,6-dimethyl-1,4-dihydropyridine-3,5-dicarboxylate:

The title compound was obtained from 356 mg (1.26 mmol) of 2,2-diphenylethyl acetoacetate, 177 mg (1.26 mmol) of 3-chlorobenzaldehyde and 195 mg (1.26 mmol) of 2-cyanoethyl 3-aminocrotonate in the same manner as that of Example 1-1).

Yield: 614 mg (1.13 mmol) (90.1%) MS (ESI, m/z) 541 (M+H)+ 1H-NMR (CDCl3): 2.12 (3H, s), 2.26 (3H, s), 2.54 (2H, t), 4.14–4.25 (2H, m), 4.32 (1H, t), 4.61 (2H, d), 4.78 (1H, s), 6.33 (1H, br), 6.89 (1H, d), 6.99–7.08 (3H, m), 7.16–7.31 (2H, m)

3) Synthesis of mono(2,2-diphenylethyl)4-(3-chlorophenyl)-2,6-dimethyl-1,4-dihydropyridine-3,5-dicarboxylate:

The title compound was obtained from 380 mg (0.702 mmol) of 3-(2-cyanoethyl)5-(2,2-diphenylethyl)4-(3-chlorophenyl)-2,6-dimethyl-1,4-dihydropyridine-3,5-dicarboxylate in the same manner as that of Example 1-2).

Yield: 113 mg (0.232 mmol) (33.0%) MS (ESI, m/z) 488 (M+H)+ 1H-NMR (DMSO-d6): 2.03 (3H, s), 2.21 (3H, s), 4.31 (1H, t), 4.56 (2H, d), 4.74 (1H, s), 6.86 (1H, br), 6.97 (1H, s), 7.13 (2H, d), 7.18–7.38 (10H, m)

EXAMPLE 3

Synthesis of mono(4,4-diphenylbutane-1-yl)4-(3-chlorophenyl)-2,6-dimethyl-1,4-dihydropyridine-3,5-dicarboxylate 1) Synthesis of 1,1-diphenyl-1,4-butanediol:

60 ml (120 mmol) of 2 M solution of phenyl magnesium bromide in THF was added dropwise to 4.33 g (50.3 mmol) of γ-butyrolactone in 60 ml of THF for the duration of 50 minutes. After stirring at room temperature overnight, a saturated aqueous ammonium chloride solution and then 2 N hydrochloric acid were added dropwise to the reaction mixture. After the extraction with ethyl acetate, the organic layer was dried over anhydrous sodium sulfate and concentrated under reduced pressure to obtain the title compound.

Yield: 12.24 g (50.5 mmol) (100%) 1H-NMR (CDCl3): 1.58 (2H, qui), 2.42 (2H, t), 3.65 (2H, t), 7.16–7.36 (6H, m), 7.42 (4H, d)

2) Synthesis of 4,4-diphenylbutane-1-ol:

11.2 g (46.2 mmol) of 1,1-diphenyl-1,4-butanediol was hydrogenated (45° C., 5 atm) in 100 ml of methanol in the presence of 0.5 ml of concentrated sulfuric acid and 10% palladium/carbon to obtain the title compound.

Yield: 3.49 g (15.4 mmol) (33.4%) 1H-NMR (CDCl3): 1.18 (1H, s), 1.49–1.61 (2H, m), 2.06–2.18 (2H, m), 3.65 (2H, t), 3.91 (1H, t), 7.08–7.31 (10H, m)

3) Synthesis of 4,4-diphenylbutane-1-yl acetoacetate:

825 mg (3.65 mmol) of 4,4-diphenylbutane-1-ol, 0.1 ml (0.72 mmol) of triethylamine and 0.40 ml (5.19 mmol) of diketene were stirred in 30 ml of toluene under heating at 80° C. for 4 hours. After the addition of saturated aqueous sodium hydrogencarbonate solution at room temperature followed by the extraction with ethyl acetate, the organic layer was dried over anhydrous sodium sulfate and concentrated under reduced pressure to obtain the title compound.

Yield: 1.13 g (3.64 mmol) (99.7%) 1H-NMR (CDCl3): 1.55–1.68 (2H, m), 2.06–2.17 (2H, m), 2.25 (3H, s), 3.43 (2H, s), 3.90 (1H, t), 4.15 (2H, t), 7.17–7.32 (10H, m)

4) Synthesis of 3-(2-cyanoethyl)5-(4,4-diphenylbutane-1-yl)4-(3-chlorophenyl)-2,6-dimethyl-dihydropyridine-3,5-dicarboxylate:

The title compound was obtained from 780 mg (2.51 mmol) of 4,4-diphenylbutane-1-yl acetoacetate, 390 mg (2.52 mmol) of 2-cyanoethyl 3-aminocrotonate and 0.285 ml (2.52 mmol) of 3-chlorobenzaldehyde in the same manner as that of Example 1-1).

Yield: 786 mg (1.38 mmol) (55.0%) MS (ESI, m/z) 567 (M–H)– 1H-NMR (CDCl3): 1.52–1.62 (2H, m), 1.96–2.04 (2H, m), 2.34 (3H, s), 2.35 (3H, s), 2.69 (2H, t), 3.86 (1H, t), 3.96–4.16 (2H, m), 4.94 (1H, s), 5.67 (1H, s), 7.03–7.31 (14H, m)

5) Synthesis of mono(4,4-diphenylbutane-1-yl)4-(3-chlorophenyl)-2,6-dimethyl-1,4-dihydropyridine-3,5-dicarboxylate:

The title compound was obtained from 615 mg (1.08 mmol) of 3-(2-cyanoethyl)5-(4,4-diphenylbutane-1-yl)4-(3-chlorophenyl)-2,6-dimethyl-1,4-dihydropyridine-3,5-dicarboxylate in the same manner as that in Example 1-2).

Yield: 252 mg (0.49 mmol) (45.2%) MS (ESI, m/z) 514 (M–H)– 1H-NMR (DMSO-d6): 1.37–1.48 (2H, m), 1.89–2.01 (2H, m), 2.24 (3H, s), 2.26 (3H, s), 3.85–4.07 (3H, m), 4.89 (1H, s), 7.04–7.32 (14H, m), 8.82 (1H, s)

EXAMPLE 4

Synthesis of mono(4-hydroxy-4,4-diphenylbutane-1-yl)4-(3-chlorophenyl)-2,6-dimethyl-1,4-dihydropyridine-3,5-dicarboxylate 1) Synthesis of (4-hydroxy-4,4-diphenylbutane-1-yl)acetoacetate:

The title compound was obtained from 811 mg (3.35 mmol) of 1,1-diphenyl-1,4-butanediol in the same manner as that of Example 3-3).

Yield: 770 mg (2.36 mmol) (70.4%) MS (ESI, m/z) 325 (M–H)– 1H-NMR (CDCl3): 1.61–1.72 (2H, m), 2.18 (1H, s), 2.25 (3H, s), 2.32–2.40 (2H, m), 3.44 (2H, s), 4.16 (2H, t), 7.19–7.43 (10H, m)

2) Synthesis of 3-(2-cyanoethyl)5-(4-hydroxy-4,4-diphenylbutane-1-yl)4-(3-chlorophenyl)-2,6-dimethyl-1,4-dihydropyridine-3,5-dicarboxylate:

The title compound was obtained from 766 mg (2.35 mmol) of (4-hydroxy-4,4-diphenylbutane-1-yl)acetoacetate, 360 mg (2.34 mmol) of 2-cyanoethyl3-aminocrotonate and 0.265 ml (2.34 mmol) of 3-chlorobenzaldehyde in the same manner as that of Example 1-1).

Yield: 769 mg (1.31 mmol) (56.0%) MS (ESI, m/z) 583 (M–H)– 1H-NMR (CDCl3): 1.58–1.69 (2H, m), 2.24–2.34 (2H, m), 2.35 (6H, s), 2.53–2.62 (2H, m), 4.05 (2H, t), 4.21 (2H, t), 4.99 (1H, s), 5.71 (1H, s), 7.05–7.08 (2H, m), 7.17–7.43 (12H, m)

3) Synthesis of mono(4-hydroxy-4,4-diphenylbutane-1-yl) 4-(3-chlorophenyl)-2,6-dimethyl-1,4-dihydropyridine-3,5-dicarboxylate:

The title compound was obtained from 762 mg (1.30 mmol) of 3-(2-cyanoethyl)5-(4-hydroxy-4,4-diphenylbutane-1-yl)4-(3-chlorophenyl)-2,6-dimethyl-1,4-dihydropyridine-3 5-dicarboxylate, in the same manner as that of Example 1-2).

Yield: 640 mg (1.20 mmol) (92.5%) MS (ESI, m/z) 530 (M−H)− 1H-NMR (DMSO-d6): 1.42–1.56 (2H, m), 2.14–2.26 (2H, m), 2.24–2.34 (2H, m), 2.24 (3H, s), 2.26 (3H, s), 3.88–4.00 (2H, m), 4.90 (1H, s), 5.51 (1H, s), 7.16–7.43 (14H, m), 8.82 (1H, s)

EXAMPLE 5

Synthesis of mono(3,3-diphenylpropane-1-yl)2,6-dimethyl-4-(2-nitrophenyl)-1,4-dihydropyridine-3,5-dicarboxylate:

1) Synthesis of 3-(2-cyanoethyl)5-(3,3-diphenylpropane-1-yl)2,6-dimethyl-4-(2-nitrophenyl)-1,4-dihydropyridine-3,5-dicarboxylate:

The title compound was obtained from 768 mg (2.59 mmol) of 3,3-diphenylpropyl acetoacetate, 401 mg (2.60 mmol) of 2-cyanoethyl 3-aminocrotonate and 391 mg (2.59 mmol) of 2-nitrobenzaldehyde in the same manner as that of Example 1-1).

Yield: 592 mg (1.05 mmol) (40.5%) MS (ESI, m/z) 564 (M−H)− 1H-NMR (CDCl3): 2.24–2.41 (2H, m), 2.32 (3H, s), 2.34 (3H, s), 2.67 (2H, t), 3.82–4.34 (5H, m), 5.71 (1H, s), 5.76 (1H, s), 7.11–7.70 (14H, m)

2) Synthesis of mono(3,3-diphenylpropane-1-yl)2,6-dimethyl-4-(2-nitrophenyl)-1,4-dihydropyridine-3,5-dicarboxylate:

The title compound was obtained from 586 mg (1.04 mmol) of 3-(2-cyanoethyl)5-(3,3-diphenylpropane-1-yl)2,6-dimethyl-4-(2-nitrophenyl)-1,4-dihydropyridine-3,5-dicarboxylate in the same manner as that of Example 1-2).

Yield: 409 mg (0.80 mmol) (76.7%) MS (ESI, m/z) 511 (M−H)− 1H-NMR (DMSO-d6): 2.19 (3H, s), 2.20–2.30 (2H, m), 2.26 (3H, s), 3.67–3.86 (3H, m), 5.59 (1H, s), 7.04–7.30 (10H, m), 7.37 (1H, t), 7.49 (1H, d), 7.63 (1H, t), 7.70 (1H, d), 8.84 (1H, s)

EXAMPLE 6

Synthesis of mono(diphenylmethyl)4-(3-chlorophenyl)-2,6-dimethyl-1,4-dihydropyridine-3,5-dicarboxylate:

1) Synthesis of Diphenylmethyl Acetoacetate:

The title compound was obtained from 500 mg (2.71 mmol) of benzhydrol in the same manner as that of Example 2-1).

Yield: 920 mg (3.43 mmol) (quantitative) 1H-NMR (CDCl3): 2.22 (3H, s), 3.55 (2H, s), 6.93 (1H, s), 7.25–7.40 (10H, m)

2) Synthesis of 3-(2-cyanoethyl)5-(diphenylmethyl)4-(3-chloorophenyl)-2,6-dimethyl-1,4-dihydropyridine-3,5-dicarboxylate:

The title compound was obtained from 200 mg (0.745 mmol) of diphenylmethyl acetoacetate, 109 mg (0.745 mmol) of 3-chlorobenzaldehyde and 115 mg (0.745 mmol) of 2-cyanoethyl 3-aminocrotonate in the same manner as that of Example 1-1).

Yield: 360 mg (0.68 mmol) (91.7%) MS (ESI, m/z) 525 (M−H)− 1H-NMR (CDCl3): 2.31 (3H, s), 2.34 (3H, s), 2.62 (2H, t), 4.26 (2H, t), 5.08 (1H, s), 6.00 (1H, s), 6.81 (1H, s), 6.97–7.00 (2H, m), 7.10–7.35 (12H, m)

3) Synthesis of mono(diphenylmethyl)4-(3-chlorophenyl)-2,6-dimethyl-1,4-dihydropyridine-3,5-dicarboxylate:

The title compound was obtained from 360 mg (0.683 mmol) of 3-(2-cyanoethyl)5-(diphenylmethyl)4-(3-chlorophenyl)-2,6-dimethyl-1,4-dihydropyridine-3,5-dicarboxylate in the same manner as that of Example 1-2).

Yield: 169 mg (0.36 mmol) (52.2%) MS (ESI, m/z) 472 (M−H)− 1H-NMR (DMSO-d6): 2.22 (3H, s), 2.30 (3H, s), 4.96 (1H, s), 6.72 (1H, s), 6.95–6.98 (2H, m), 7.15–7.34 (12H, m), 8.90 (1H, s)

EXAMPLE 7

Synthesis of (3,3-diphenylpropane-1-yl)5-(azepane-1-carbonyl)-4-(3-chlorophenyl)-2,6-dimethyl-1,4-dihydropyridine-3-carboxylate 152 mg (0.303 mmol) of mono(3,3-diphenylpropane-1-yl)4-(3-chlorophenyl)-2,6-dimethyl-1,4-dihydropyridine-3,5-dicarboxylate and 45.0 mg (0.454 mmol) of hexamethyleneimine were dissolved in 20 ml of dichloromethane. 87.1 mg (0.454 mmol) of 1-(3-dimethylaminopropyl)-3-ethylcarbodiimide hydrochloride and 46.4 mg (0.303 mmol) of 1-hydroxybenzotriazole were added to the obtained solution, and they were stirred at room temperature overnight. The reaction mixture was diluted with dichloromethane and then washed with saturated aqueous sodium hydrogencarbonate solution. The organic layer was dried over anhydrous sodium sulfate and then concentrated under reduced pressure. The residue was purified by the silica gel column chromatography (hexane/ethyl acetate=3/1 to 1/1) to obtain the title compound.

Yield: 30 mg (0.051 mmol) (17.0%) MS (ESI, m/z) 583 (M+H)+ 1H-NMR (CDCl3): 1.00 (2H, br), 1.25–1.50 (5H, m), 1.60–1.74 (6H, m), 2.12–2.20 (2H, m), 2.34 (3H, s), 3.14 (2H, br), 3.70–3.90 (3H, m), 4.92 (1H, s), 5.68 (1H, s), 6.96 (2H, d), 7.12–7.28 (12H, m)

EXAMPLE 8

Synthesis of mono(5,5-diphenyl-2-pentene-1-yl)4-(3-chlorophenyl)-2,6-dimethyl-1,4-dihydropyridine-3,5-dicarboxylate 1) Synthesis of ethyl 5,5-diphenyl-2-pentenoate:

2.37 g (18.7 mmol) of oxalyl chloride and 2.92 g (37.3 mmol) of DMSO were dissolved in 10 ml of dichloromethane at −78° C. After stirring for one hour, 2.00 g (9.33 mmol) of 3,3-diphenyl-1-propanol was added to the obtained solution at that temperature, and they were stirred for additional 2 hours. 5.66 g (56.0 mmol) of triethylamine was added to the obtained mixture and they were stirred for one hour while the temperature was returned to room temperature. After the dilution with dichloromethane followed by the washing with saturated aqueous sodium chloride solution, the organic layer was dried over anhydrous sodium sulfate and then concentrated under reduced pressure. The residue thus obtained was added to a THF solution obtained by stirring 2.67 g (11.9 mmol) of ethyl diethylphosphonoacetate and 596 mg (14.9 mmol) of sodium hydride (60% oily) under cooling with ice for one hour. They were stirred at room temperature for 2 hours. After the dilution with ethyl acetate followed by the washing with saturated aqueous sodium chloride solution, the organic layer was dried over anhydrous sodium sulfate and then concentrated under reduced pressure. The residue thus obtained was purified by the silica gel chromatography (hexane/ethyl acetate=5/1 to 3/1) to obtain the title compound.

Yield: 2.22 g (7.92 mmol) (79.2%) MS (ESI, m/z) 281 (M+H)+ 1H-NMR (CDCl3): 1.24 (3H, t), 2.96 (2H, t), 4.05–4.18 (3H, m), 5.81 (1H, d), 6.87 (1H, dt), 7.16–7.29 (10H, m)

2) Synthesis of 5,5-diphenyl-2-pentene-1-ol:

2.22 mg (7.92 mmol) of ethyl 5,5-diphenyl-2-pentenoate was dissolved in 30 ml of dichloromethane. 16.1 ml (15.1 mmol) of diisobutylaluminum hydride (0.94 mol/L: hexane solution) was added to the obtained solution under cooling with ice, and they were stirred at room temperature for 2 days. Water was added to the reaction mixture and they were stirred under cooling with ice. The precipitate thus formed was filtered through Celite. The precipitate was washed with ethyl acetate. The filtrate was concentrated under reduced pressure, and the obtained residue was purified by the silica gel chromatography (hexane/ethyl acetate=3/1 to 1/1) to obtain the title compound.

Yield: 1.42 g (5.96 mmol) (75.2%) 1H-NMR (CDCl3): 2.82 (2H, t), 3.97–4.00 (3H, m), 5.60–5.65 (2H, m), 7.17–7.29 (10H, m)

3) Synthesis of 5,5-diphenyl-2-pentene-1-yl acetoacetate:

The title compound was obtained from 500 mg (2.10 mmol) of 5,5-diphenyl-2-pentene-1-ol in the same manner as that of Example 2-1).

Yield: 860 mg (2.67 mmol) (quantitative yield) MS (ESI, m/z) 321 (M–H)– 1H-NMR (CDCl3): 2.22 (3H, s), 2.82 (2H, t), 3.40 (2H, s), 3.99 (1H, t), 4.49 (2H, d), 5.52–5.75 (2H, m), 7.16–7.28 (10H, m)

4) Synthesis of 3-(2-cyanoethyl)5-(5,5-diphenyl-2-pentene-1-yl)4-(3-chlorophenyl)-2,6-dimethyl-1,4-dihydropyridine-3,5-dicarboxylate:

The title compound was obtained from 310 mg (0.956 mmol) of 5,5-diphenyl-2-pentene-1-yl acetoacetate, 139 mg (0.956 mmol) of 3-chlorobenzaldehyde and 147 mg (0.956 mmol) of 2-cyanoethyl 3-aminocrotonate in the same manner as that of Example 1-1).

Yield: 440 mg (0.76 mmol) (79.2%) MS (ESI, m/z) 581 (M+H)+ 1H-NMR (CDCl3): 2.25 (3H, s), 2.33 (3H, s), 2.59 (2H, t), 2.79 (2H, t), 3.98 (1H, t), 4.18–4.27 (2H, m), 4.38–4.42 (2H, m), 4.93 (1H, s), 5.48–5.65 (2H, m), 5.95 (1H, s), 7.10–7.26 (14H, m)

5) Synthesis of mono(5,5-diphenyl-2-pentene-1-yl)4-(3-chlorophenyl)-2,6-dimethyl-1,4-dihydropyridine-3,5-dicarboxylate:

The title compound was obtained from 440 mg (0.76 mmol) of 3-(2-cyanoethyl)5-(5,5-diphenyl-2-pentene-1-yl) 4-(3-chlorophenyl)-2,6-dimethyl-1,4-dihydropyridine-3,5-dicarboxylate in the same manner as that of Example 1-2).

Yield: 244 mg (0.46 mmol) (60.1%) MS (ESI, m/z) 528 (M+H)+ 1H-NMR (DMSO-d6): 2.18 (3H, s), 2.26 (3H, s), 2.49–2.51 (2H, m), 3.98 (1H, t), 4.32 (2H, br), 4.81 (1H, s), 5.53 (2H, br), 7.06–7.30 (14H, m), 8.80 (1H, s)

EXAMPLE 9

Synthesis of mono(5,5-diphenyl-2-penene-1-yl)4-(3-chlorophenyl)-2,6-dimethyl-1,4-dihydropyridine-3,5-dicarboxylate 1) Synthesis of 5,5-diphenylpentanol:

10 ml of methanol was added to a mixture of 320 mg (1.34 mmol) of 5,5-diphenyl-2-pentene-1-ol and a catalytic amount of 10% palladium/carbon, and they were stirred in hydrogen atmosphere at room temperature under ambient pressure for 12 hours. The catalyst was filtered out and the obtained filtrate was concentrated under reduced pressure to obtain the unpurified title compound.

Yield: 320 mg (1.33 mmol) (quantitative yield) 1H-NMR (CDCl3): 1.26–1.38 (2H, m), 1.55–1.64 (2H, m), 2.00–2.11 (2H, m), 3.59 (2H, q), 3.85–3.92 (1H, m), 7.15–7.30 (10H, m)

2) Synthesis of (5,5-diphenylpentane-1-yl)acetoacetate:

The title compound was obtained from 320 g (1.33 mmol) of 5,5-diphenylpentanol in the same manner as that of Example 2-1).

Yield: 180 mg (0.56 mmol) (41.7%) MS (ESI, m/z) 323 (M–H)– 1H-NMR (CDCl3): 1.28–1.38 (2H, m), 1.63–1.73 (2H, m), 2.07 (2H, dd), 2.22 (3H, s), 3.40 (2H, s), 3.89 (1H, t), 4.10 (2H, t), 7.14–7.30 (10H, m)

3) Synthesis of 3-(2-cyanoethyl)5-(5,5-diphenylpentane-1-yl)4-(3-chlorophenyl)-2,6-dimethyl-1,4-dihydropyridine-3,5-dicarboxylate:

The title compound was obtained from 180 mg (0.555 mmol) of (5,5-diphenyl-2-pentane-1-yl)acetoacetate, 80.8 mg (0.555 mmol) of 3-chlorobenzaldehyde and 85.5 mg (0.555 mmol) of 2-cyanoethyl 3-aminocrotonate in the same manner as that of Example 1-1).

Yield: 150 mg (0.26 mmol) (55.6%) MS (ESI, m/z) 583 (M+H)+ 1H-NMR (CDCl3): 1.11–1.21 (2H, m), 1.50–1.62 (2H, m), 1.84 (3H, s), 1.93–1.98 (2H, m), 2.20 (3H, s), 2.65 (2H, t), 3.77 (1H, t), 3.89–3.99 (2H, m), 4.27 (2H, t), 4.84 (1H, s), 5.80 (1H, s), 7.02–7.20 (14H, m)

4) Synthesis of mono(5,5-diphenyl-pentane-1-yl)4-(3-chlorophenyl)-2,6-dimethyl-1,4-dihydropyridine-3,5-dicarboxylate:

The title compound was obtained from 150 mg (0.257 mmol) of 3-(2-cyanoethyl)5-(5,5-diphenylpentane-1-yl)4-(3-chlorophenyl)-2,6-dimethyl-1,4-dihydropyidine-3,5-dicarboxylate in the same manner as that of Example 1-2).

Yield: 54.0 mg (0.102 mmol) (39.6%) MS (ESI, m/z) 530 (M+H)+ 1H-NMR (DMSO-d6): 1.05–1.20 (2H, m), 1.55 (2H, t), 1.98 (2H, q), 2.19 (3H, s), 2.25 (3H, s), 3.81–3.99 (3H, m), 4.83 (1H, s), 7.05–7.27 (14H, m), 8.78 (1H, s)

EXAMPLE 10

Synthesis of 3-(3,3-diphenylpropane-1-yl)4-(3-chlorophenyl)-2-ethyl-6-methyl-1,4-dihydropyridine-3,5-dicarboxylate 1) Synthesis of (3,3-diphenylpropane-1-yl)3-oxopentanoate:

3.0 g (23.1 mg) of methyl 3-oxopentanoate and 4.9 g (23.1 mg) of 3,3-diphenylpropanol were stirred in 60 ml of toluene under heating at 100° C. overnight. Toluene was distilled out under reduced pressure to obtain the title compound.

MS (ESI, m/z) 311 (M+H)+ 1H-NMR (CDCl3): 1.10 (3H, t), 2.32–2.45 (3H, m), 2.55 (1H, q), 3.40 (2H, s), 4.03–4.12 (3H, m), 7.16–7.31 (10H, m)

2) Synthesis of 5-(2-cyanoethyl)3-(3,3-diphenylpropane-1-yl)4-(3-chlorophenyl)-2-ethyl-6-methyl-1,4-dihydropyridine-3,5-dicarboxylate:

The title compound was obtained from 300 mg (0.97 mmol) of (3,3-diphenylpropane-1-yl)3-oxopentanoate, 150 mg (0.97 mmol) of 2-cyanoethyl 3-aminocrotonate and 109 μl (0.97 mmol) of 3-chlorobenzaldehyde in the same manner as that of Example 1-1).

Yield: 249 mg (0.44 mmol) (45.2%) MS (ESI, m/z) 569 (M+H)+ 1H-NMR (CDCl3): 1.26 (3H, t), 2.32–2.44 (3H, m), 2.55 (1H, q), 3.40 (2H, s), 4.03–4.12 (3H, m), 7.16–7.31 (10H, m)

3) Synthesis of 5-(3,3-diphenylpropane-1-yl)4-(3-chlorophenyl)-2-ethyl-6-methyl-1,4-dihydropyridine-3,5-dicarboxylate:

The title compound was obtained from 157 mg (0.28 mmol) of 5-(2-cyanoethyl)3-(3,3-diphenylpropane-1-yl)4-(3-chlorophenyl)-2-ethyl-6-methyl-1,4-dihydropyidine-3,5-dicarboxylate in the same manner as that of Example 1-2).

Yield: 96.6 mg (0.19 mmol) (67.9%) MS (ESI, m/z) 516 (M+H)+ 1H-NMR (CDCl3): 1.26 (3H, t), 2.17 (3H, s), 2.64–2.90 (4H, m), 3.91–4.00 (3H, m), 4.28–4.30 (4H, m), 5.00 (1H, s), 5.67 (1H, s), 7.05–7.26 (14H, m)

EXAMPLE 11

Synthesis of 3-(3,3-diphenylpropane-1-yl)4-(3-chlorophenyl)-2-(2-cyclohexylethoxymethyl)-6-methyl-1,4-dihydropyridine-3,5-dicarboxylate 1) Synthesis of (3,3-diphenylpropane-1-yl)4-chloroacetoacetate:

3.2 ml (23.7 mmol) of ethyl 4-chloroacetoacetate and 5.00 g (23.6 mmol) of 3,3-diphenyl-1-propanol were heated at 130° C. in 100 ml of toluene overnight. Toluene was distilled out under reduced pressure to obtain the title compound.

Yield: 8.57 g (25.9 mmol) (quantitative yield) MS (ESI, m/z) 329 (M–H)– 1H-NMR (CDCl3): 2.30–2.46 (2H, m), 2.35 (2H, s), 3.59 (2H, s), 4.00–4.25 (3H, m), 7.15–7.31 (10H, m)

2) Synthesis of (3,3-diphenylpropane-1-yl)4-(2-cyclohexylethoxy)-3-oxobutanoate:

2.5 ml of a solution of 610 mg (1.84 mmol) of (3,3-diphenylpropane-1-yl)4-chloroacetoacetate in THF was added dropwise to a suspension of 158 mg (3.95 mmol) of sodium hydride (60% oily) in 5 ml of THF at 0° C., and they were stirred at room temperature for 20 minutes. An alkoxide solution previously prepared by adding 397 mg (3.09 mmol) of 2-cyclohexylethanol to 5 ml of a solution of 134 mg (3.36 mmol) of sodium hydride (60% oily) in THF was added to the obtained mixture at 0° C., and they were stirred at room temperature for 3 nights. THF was evaporated under reduced pressure. Water was added to the residue. The obtained mixture was washed with ethyl acetate. The aqueous layer was acidified with 2 N hydrochloric acid. After the extraction with ethyl acetate followed by drying over sodium sulfate, ethyl acetate was evaporated under reduced pressure to obtain the title compound.

Yield: 420 mg (0.99 mmol) (54%) MS (ESI, m/z) 423 (M+H)+ 1H-NMR (CDCl3): 0.94–1.78 (13H, m), 2.40 (2H, q), 3.49 (2H, s), 3.50 (2H, t), 4.05 (1H, t), 4.07 (2H, s), 4.10 (2H, t), 7.15–7.32 (10H, m)

3) Synthesis of 5-(2-cyanoethyl)3-(3,3-diphenylpropane-1-yl)4-(3-chlorophenyl)-2-(2-cyclohexylethoxymethyl)-6-methyl-1,4-dihydropyridine-3,5-dicarboxylic acid:

91.6 mg (0.217 mmol) of (3,3-diphenylpropane-1-yl)4-(2-cyclohexylethoxy)-3-oxobutanoate and 25 μl (0.221 mmol) of 3-chlorobenzaldehyde were stirred in the presence of catalytic amounts of acetic acid and piperidine at room temperature for 3 nights. The solvent was evaporated. 3 ml of 2-propanol and 37.5 mg (0.243 mmol) of 2-cyanoethyl 3-aminocrotonate were added to the residue and they were stirred under heating at 80° C. overnight. 2-Propanol was evaporated under reduced pressure, and the residue was purified by the thin layer silica gel chromatography (hexane/ethyl acetate=2/1) to obtain the title compound.

Yield: 37.9 mg (0.056 mmol) (25.6%) MS (ESI, m/z) 681 (M+H)+ 1H-NMR (CDCl3): 0.899–1.75 (13H, m), 2.33 (2H, q), 2.38 (3H, s), 2.64 (2H, t), 3.55–3.63 (2H, m), 3.91 (1H, t), 3.92–4.00 (2H, m), 4.21–4.35 (2H, m), 4.63 (1H, d), 4.70 (1H, d), 4.99 (1H, s), 7.08–7.30 (15H, m)

4) Synthesis of 3-(3,3-diphenylpropane-1-yl)4-(3-chlorophenyl)-2-(2-cyclohexylethoxymethyl)-6-methyl-1,4-dihydropyridine-3,5-dicarboxylate:

The title compound was obtained from 5-(2-cyanoethyl) 3-(3,3-diphenylpropane-1-yl)4-(3-chlorophenyl)-2-(2-cyclohexylethoxymethyl)-6-methyl-1,4-dihydropyridine-3,5-dicarboxylate in the same manner as that of Example 1-2).

Yield: 20.8 mg (0.033 mmol) (93.5%) MS (ESI, m/z) 628 (M+H)+ 1H-NMR (CDCl3): 0.870–1.76 (13H, m), 2.29–2.39 (2H, m), 2.37 (3H, s), 3.62 (2H, t), 3.89 (1H, t), 3.91–3.99 (2H, m), 4.64 (1H, d), 4.71 (1H, d), 5.02 (1H, s), 7.05–7.30 (15H, m)

EXAMPLE 12

Synthesis of 5-(3,3-diphenylpropane-1-yl)4-(3-chlorophenyl)-2-methyl-6-(2-piperidine-1-yl-ethoxymethyl)-1,4-dihydropyridine-3,5-dicarboxylate 1) Synthesis of (3,3-diphenylpropane-1-yl)3-oxo-4-(2-(piperidine-1-yl)ethoxy)butanoate:

2.5 ml of a solution of 350 mg (2.71 mmol) of 2-(piperidine-1-yl)ethanol in THF was added dropwise to a suspension of 333 mg (8.07 mmol) of sodium hydride (60% oily) in THF at 0° C., and they were stirred at room temperature for 1 hour. 2.5 ml of a solution of 808 mg (2.44 mmol) of 3,3-diphenylpropane-1-yl)4-chloroacetoacetate in THF was added dropwise to the obtained mixture at 0° C., and they were stirred at room temperature three nights. THF was evaporated under reduced pressure. The residue was acidified with 2 N hydrochloric acid. After the extraction with ethyl acetate followed by drying over sodium sulfate, ethyl acetate was evaporated under reduced pressure to obtain the title compound.

Yield: 739 mg (1.74 mmol) (71.3%) MS (ESI, m/z) 424 (M+H)+ 1H-NMR (CDCl3): 1.38–1.64 (6H, m), 2.32–2.44 (6H, m), 2.55 (2H, t), 3.52 (2H, bs), 3.62 (2H, t), 4.06 (1H, t), 4.09 (2H, t), 4.13 (2H, bs), 7.15–7.27 (10H, m)

2) Synthesis of 3-(2-cyanoethyl)5-(3,3-diphenylpropane-1-yl)4-(3-chlorophenyl)-2-methyl-6-(2-piperidine-1-yl-ethoxymethyl)-1,4-dihydropyridine-3,5-dicarboxylate:

The title compound was obtained from 147 mg (0.348 mmol) of (3,3-diphenylpropane-1-yl)3-oxo-4-(2-piperidine-1-yl-ethoxy)butanoate in the same manner as that of Example 11-3).

Yield: 20.4 mg (0.030 mmol) (8.6%) MS (ESI, m/z) 682 (M+H)+ 1H-NMR (CDCl3): 1.43–1.75 (6H, m), 2.34 (2H, q), 2.43 (3H, s), 2.50–2.65 (8H, m), 3.62–3.71 (2H, m), 3.86–4.01 (3H, m), 4.21–4.35 (2H, m), 4.65 (2H, d), 4.73 (2H, d), 4.99 (1H, s), 7.08–7.30 (14H, m), 8.12 (1H, bs)

3) Synthesis of 5-(3,3-diphenylpropane-1-yl)4-(3-chlorophenyl)-2-methyl-6-(2-(piperidine-1-yl)ethoxymethyl)-1,4-dihydropyridine-3,5-dicarboxylate:

3-(2-cyanoethyl)5-(3,3-diphenylpropane-1-yl)4-(3-chlorophenyl)-2-methyl-6-(2-(piperidine-1-yl)ethoxymethyl)-1,4-dihydropyridine-3,5-dicarboxylate was dissolved in 1 ml of methanol. 60 µl of 1 N aqueous sodium hydroxide solution was added to the obtained solution, and they were stirred at room temperature for 2 hours. Methanol was evaporated under reduced pressure. 2 N hydrochloric acid and water were added to the residue. After the extraction with ethyl acetate, ethyl acetate was evaporated under reduced pressure to obtain the title compound.

Yield: 13.6 mg (0.022 mmol) (72.2%) MS (ESI, m/z) 629 (M+H)+ 1H-NMR (CDCl3): 1.42–1.70 (6H, m), 2.24–2.36 (2H, m), 2.31 (3H, s), 2.55–2.62 (6H, m), 3.61 (2H, t), 3.84–3.94 (3H, m), 4.55 (1H, d), 4.85 (1H, d), 5.09 (1H, s), 7.03–7.32 (14H, m), 7.57 (1H, bs)

EXAMPLE 13

Synthesis of mono(3,3-diphenylpropane-1-yl)2,6-dimethyl-4-(3-nitrophenyl)-1,4-dihydropyridine-3,5-dicarboxylate 1) Synthesis of 3-(2-cyanoethyl)5-(3,3-diphenylpropane-1-yl)2,6-dimethyl-4-(3-nitrophenyl)-1,4-dihydropyridine-3,5-dicarboxylate:

The title compound was obtained from 740 mg (2.50 mmol) of 3,3-diphenylpropyl acetoacetate, 394 mg (2.56 mmol) of 2-cyanoethyl 3-aminocrotonate and 380 mg (2.51 mmol) of 3-nitrobenzaldehyde in the same manner as that of Example 1-1).

Yield: 841 mg (1.49 mmol) (59.6%) MS (ESI, m/z) 564 (M−H)− 1H-NMR (CDCl3):2.30–2.40 (8H, m), 2.66 (2H, t), 3.90 (1H, t), 3.99 (2H, t), 4.12 (2H, q), 4.20–4.36 (2H, m), 5.11 (1H, s), 5.90 (1H, s), 7.11–7.30 (10H, m), 7.38 (1H, t), 7.66–7.72 (1H, m), 7.98–8.04 (1H, m), 8.13 (1H; t)

2) Synthesis of mono(3,3-diphenylpropane-1-yl)2,6-dimethyl-4-(3-nitrophenyl)-1,4-dihydropyridine-3,5-dicarboxylate:

The title compound was obtained from 831 mg (1.47 mmol) of 3-(2-cyanoethyl)5-(3,3-diphenylpropane-1-yl)2,6-dimethyl-4-(3-nitrophenyl)-1,4-dihydropyridine-3,5-dicarboxylate in the same manner as that of Example 1-2).

Yield: 493 mg (0.96 mmol) (65.4%) MS (ESI, m/z) 511 (M−H)− 1H-NMR (DMSO-d6): 2.26 (3H, s), 2.30 (3H, s), 2.26–2.33 (2H, m), 3.75–3.90 (3H, m), 5.05 (1H, s), 7.10–7.29 (10H, m), 7.53–7.67 (2H, m), 8.01–8.08 (2H, m), 8.96 (1H, s)

EXAMPLE 14

Synthesis of 3-(3,3-diphenylpropane-1-yl)4-(3-chlorophenyl)-2-methoxymethyl-6-methyl-1,4-dihydropyridine-3,5-dicarboxylate 1) Synthesis of (3,3-diphenylpropane-1-yl)4-methoxy-3-oxobutanoate:

2.5 ml of a solution of 0.879 mg (2.66 mmol) of (3,3-diphenylpropane-1-yl)4-chloroacetoacetate in 2.5 ml of THF was added dropwise to a suspension of 160 mg of sodium hydride (60% oily) in 5 ml of THF at 0° C. and they were stirred for 30 minutes. 820 µl of 28% solution of sodium methoxide in methanol was added to the obtained mixture. After stirring overnight, methanol was added to the reaction mixture, and the obtained mixture was concentrated and fractionated with ethyl acetate and water. After the drying over sodium sulfate followed by the purification by the silica gel chromatography (hexane/ethyl acetate=3/1), the title compound was obtained.

Yield: 372 mg (1.13 mmol) (42.9%) MS (ESI, m/z) 327 (M+H)+ 1H-NMR (CDCl3): 2.39 (2H, dt), 3.41 (3H, s), 3.48 (2H, s), 4.03–4.12 (5H, m), 7.15–7.32 (10H, m)

2) Synthesis of 5-(2-cyanoethyl)3-(3,3-diphenylpropane-1-yl)4-(3-chlorophenyl)-2-methoxymethyl-6-methyl-1,4-dihydropyridine-3,5-dicarboxylate:

205.9 mg (0.63 mmol) of (3,3-diphenylpropane-1-yl)4-methoxy-3-oxobutanoate and 88.7 mg (0.63 mmol) of 3-chlorobenzaldehyde were stirred in the presence of a catalytic amount of acetic acid and piperidine in 4 ml of 2-propanol at room temperature overnight. 97.2 mg (0.63 mmol) of 2-cyanoethyl 3-aminocrotonate was added to the obtained mixture and they were stirred under heating at 70° C. overnight. 2-Propanol was evaporated under reduced pressure, and the residue was purified by the silica gel chromatography (methylene chloride/methanol=100/1) to obtain the title compound.

Yield: 24.9 mg (0.04 mmol) (6.7%) MS (ESI, m/z) 585 (M+H)+ 1H-NMR (CDCl3): 2.29–2.38 (5H, m), 2.62–2.71 (2H, m), 3.48 (3H, s), 3.88–3.99 (3H, m), 4.28 (2H, ddd), 4.60 (1H, d), 4.68 (1H, d), 4.99 (1H, s), 7.02–7.30 (14H, m)

3) Synthesis of 3-(3,3-diphenylpropane-1-yl)4-(3-chlorophenyl)-2-methoxymethyl-6-methyl-1,4-dihydropyidine-3,5-dicarboxylate:

The title compound was obtained from 23.9 mg (0.04 mmol) of 5-(2-cyanoethyl)3-(3,3-diphenylpropane-1-yl)4-(3-chlorophenyl)-2-methoxymethyl-6-methyl-1,4-dihydropyridine-3,5-dicarboxylate in the same manner as that of Example 1-2.

Yield: 10.9 mg (0.02 mmol) (50.1%) MS (ESI, m/z) 530 (M−H)− 1H-NMR (CDCl3): 2.33–2.38 (5H, m), 3.49 (3H, s), 3.87–3.96 (3H, m), 4.65 (1H, d), 4.66 (1H, d), 5.00 (1H, s), 7.08–7.28 (15H, m)

EXAMPLE 15

Synthesis of t-butyl 4-(4-(3-chlorophenyl)-5-(3,3-diphenylpropoxycarbonyl)-2,6-dimethyl-1,4-dihydropyridine-3-carbonyl)piperazine-1-carboxylate 258 mg (0.51 mmol) of mono(3,3-diphenylpropane-1-yl) 4-(3-chlorophenyl)-2,6-di(methyl-1,4-dihydropyridine-3,5-dicarboxylate, 143 mg (0.77 mmol) of 1-t-butoxycarbonylpiperazine, 117 mg (0.61 mmol) of 1-(3-dimethylaminopropyl)-3-ethylcarbodiimide hydrochloride and 18 mg (0.14 mmol) of 4-dimethylaminopyridine were stirred in 15 ml of dichloromethane at room temperature overnight. Water and 1 N hydrochloric acid were added to the obtained mixture. After the extraction with dichloromethane, the organic layer was dried over anhydrous sodium sulfate and then concentrated under reduced pressure. The residue was purified by the silica gel chromatography (hexane/ethyl acetate=1/2) to obtain the title compound.

Yield: 259 mg (0.39 mmol) (76.5%) MS (ESI, m/z) 668 (M−H)− 1H-NMR (CDCl3): 1.40–1.48 (2H, m), 1.43 (9H, s), 1.73 (3H, s), 2.10–2.22 (2H, m), 2.38 (3H, s), 2.85–3.15 (4H, m), 3.62–3.92 (5H, m), 4.96 (1H, s), 5.24 (1H, s), 6.92 (2H, d), 7.08–7.29 (12H, m)

EXAMPLE 16

Synthesis of (3,3-diphenylpropane-1-yl)5-carbamoyl-4-(3-chlorophenyl)-2,6-dimethyl-1,4-dihydropyridine-3-carboxylate 208 mg (2.06 mmol) of acetoacetamide, 0.23 ml (2.00 mmol) of 3-chlorobenzaldehyde and 0.02 ml (0.20 mmol) of piperidine were heated under reflux in the presence of a catalytic amount of p-toluenesulfonic acid in 30 ml of benzene overnight while removing water. Ethyl acetate was added to the reaction mixture and they were washed with 1 N hydrochloric acid and then with saturated aqueous sodium hydrogencarbonate solution. The organic layer was dried over anhydrous sodium sulfate and then concentrated under reduced pressure to obtain 2-acetyl-3-(3-chlorophenyl)acrylamide. 10 ml of 2-propanol and 486 mg (1.65 mmol) of (3,3-diphenylpropane-1-yl)3-aminocrotonate were added to the obtained product, and they were stirred under heating at 80° C. overnight. 2-Propanol was evaporated under reduced pressure, and the residue was purified by the silica gel chromatography (hexane/ethyl acetate=1/2) to obtain the title compound.

Yield: 428 mg (0.85 mmol) (41.3%) MS (ESI, m/z) 499 (M−H)− 1H-NMR (CDCl3): 2.30 (3H, s), 2.31 (3H, s), 2.38 (2H, q), 3.95 (1H, t), 4.02 (2H, t), 4.76 (1H, s), 5.21 (2H, s), 5.58 (1H, s), 7.13–7.30 (14H, m)

EXAMPLE 17

Synthesis of 5-(3,3-diphenylpropane-1-yl)4-(3-chlorophenyl)-2-methyl-6-(2-(pyridine-2-yl)ethoxymethyl)-1,4-dihydropyridine-3,5-dicarboxylate 1) Synthesis of (3,3-diphenylpropane-1-yl)3-oxo-4-(2-(pyridine-2-yl)ethoxy)butanoate:

503 mg (4.08 mmol) of 2-(pyridine-2-yl)ethanol was added dropwise to a suspension of 326 mg (8.16 mmol) of sodium hydride (60% oily) in 10 ml of THF at 0° C., and they were stirred for 30 minutes. A solution of 0.90 mg (2.72 mmol) of (3,3-diphenylpropane-1-yl)4-chloroacetoacetate in 3 ml of THF was added dropwise to the reaction mixture, and they were stirred at room temperature overnight. After the addition of methanol, the reaction mixture was concentrated and fractionated with ethyl acetate and water. After the drying over sodium sulfate followed by the purification by the silica gel chromatography (methylene chloride/methanol=100/1), the title compound was obtained.

Yield: 699 mg (1.68 mmol) (61.6%) MS (ESI, m/z) 418 (M+H)+ 1H-NMR (CDCl3): 2.34–2.45 (2H, m), 3.10 (2H, ddd), 3.42 (2H, s), 3.90 (1H, t), 4.00–4.12 (5H, m), 4.46 (1H, t), 711–7.26 (10H, m), 7.56–7.64 (2H, m), 8.51–8.54 (2H, m)

2) Synthesis of 3,3-diphenylpropane-1-yl)3-amino-4-(2-(pyridine-2-yl)ethoxy)crotonate:

652.7 mg (1.56 mmol) of (3,3-diphenylpropane-1-yl)3-oxo-4-(2-(pyridine-2-yl)ethoxy)butanoate and 361 mg (4.69 mmol) of ammonium acetate were heated at 50° C. under stirring in 2-propanol for 5 hours. 2-Propanol was concentrated. The aqueous layer made basic and was extracted with ethyl acetate. The extract was washed with saturated aqueous sodium hydrogencarbonate solution and saturated aqueous sodium chloride solution, dried over sodium sulfate, filtered and concentrated.

Yield: 650 mg (1.56 mmol) (99.8%) MS (ESI, m/z) 417 (M+H)+ 1H-NMR (CDCl3): 2.34–2.41 (2H, m), 3.11 (2H, ddd), 3.87 (1H, t), 3.99 (1H, t), 4.04–4.11 (3H, m), 4.46 (1H, t), 713–7.27 (10H, m), 7.59–7.64 (2H, m), 8.53–8.55 (2H, m)

3) Synthesis of 3-(2-cyanoethyl)5-(3,3-diphenylpropane-1-yl)4-(3-chlorophenyl)-2-methyl-6-(2-(pyridine-2-yl)ethoxymethyl)-1,4-dihydropyidine-3,5-dicarboxylate:

651 mg (1.56 mmol) of (3,3-diphenylpropane-1-yl)3-amino-4-(2-(pyridine-2-yl)ethoxy)crotonate and 440 mg (1.56 mmol) of 2-cyanoethyl 3-(3-chlorobenzylidene)acetoacetate were stirred in 8 ml of 2-propanol under heating at 70° C. overnight. 2-Propanol was evaporated under reduced pressure, and the residue was purified by the silica gel chromatography (methylene chloride/methanol=100/3) to obtain the title compound.

Yield: 514 mg (0.78 mmol) (49.6%)

MS(ESI, m/z) 676(M+H)+ 1H-NMR (CDCl3): 2.18 (3H, s), 2.32–2.39 (2H, m), 2.64 (2H, t), 3.85–4.10 (6H, m), 4.47 (2H, ddd), 5.30 (1H, s), 7.05–7.27 (15H, m), 7.59–7.64 (2H, m), 8.51–8.60 (2H, m)

4) Synthesis of 5-(3,3-diphenylpropane-1-yl)4-(3-chlorophenyl)-2-methyl-6-(2-(pyridine-2-yl)ethoxymethyl)-1,4-dihydropyridine-3,5-dicarboxylate:

198 mg (0.34 mmol) of 3-(2-cyanoethyl)5-(3,3-diphenylpropane-1-yl)4-(3-chlorophenyl)-2-methyl-6-(2-(pyridine-2-yl)ethoxymethyl)-1,4-dihydropyridine-3,5-dicarboxylate was dissolved in 10 ml of methanol. 0.68 ml of 1 N aqueous sodium hydroxide solution was added to the obtained solution, and they were stirred at room temperature for 2 hours. Methanol was evaporated under reduced pressure. 2 N hydrochloric acid was added to the residue. After the dilution with water followed by the extraction with ethyl acetate, the extract was concentrated, purified by the thin layer silica gel chromatography and recrystallized from hexane and ethyl acetate to obtain the title compound.

Yield: 43.8 mg (0.070 mmol) (21%) MS (ESI, m/z) 623 (M+H)+ 1H-NMR (CDCl3): 2.27–2.33 (5H, m), 3.14 (2H, t), 3.88–3.99 (5H, m), 4.74 (2H, s), 5.00 (1H, s), 7.04–7.40 (15H, m), 7.63–7.65 (2H, m), 8.59–8.61 (2H, m)

EXAMPLE 18

Synthesis of 3-(3,3-diphenylpropane-1-yl)2-(2-benzyloxyethoxymethyl)-4-(3-chlorophenyl)-6-methyl-1,4-dihydropyridine-3,5-dicarboxylate 1) Synthesis of (3,3-diphenylpropane-1-yl)4-(2-benzyloxyethoxy)-3-oxobutanoate:

The title compound was obtained from 433 mg (2.85 mmol) of 2-benzyloxyethanol and 777 mg (2.35 mmol) of (3,3-diphenylpropane-1-yl)4-chloroacetoacetate in the same manner as that of Example 12-1).

Yield: 821 mg (1.84 mmol) (78.3%) MS (ESI, m/z) 445 (M−H)− 1H-NMR (CDCl3): 2.38 (2H, q), 3.51 (2H, s), 3.59–3.72 (4H, m), 4.04 (1H, t), 4.06–4.16 (2H, m), 4.18 (2H, s), 4.54 (2H, s), 7.14–7.37 (15H, m)

2) Synthesis of 2-cyanoethyl 2-acetyl-3-(3-chlorophenyl) acrylate:

1.00 g (6.45 mmol) of 2-cyanoethyl acetoacetate and 730 μl (6.44 mmol) of 3-chlorobenzaldehyde were stirred in the presence of a catalytic amount of acetic acid and piperidine in 100 ml of 2-propanol at room temperature overnight. The solvent was evaporated under reduced pressure to obtain the title compound.

Yield: 1.79 g (6.44 mmol) (quantitative yield) MS (ESI, m/z) 278 (M+H)+ 1H-NMR (CDCl3): 2.05 (3H, s), 2.63 (2H, t), 3.92 (2H, t), 7.00–7.88 (5H, m)

3) Synthesis of 5-(2-cyanoethyl)3-(3,3-diphenylpropane-1-yl)2-(2-benzyloxyethoxymethyl)-4-(3-chlorophenyl)-6-methyl-1,4-dihydropyridine-3,5dicarboxylate:

821 mg (1.84 mmol) of (3,3-diphenylpropane-1-yl)3-oxo-4-(2-(pyridine-2-yl)ethoxy)butanoate and 435 mg (5.64 mmol) of ammonium acetate were stirred in 8 ml of 2-propanol under heating at 50° C. overnight. 2-Propanol was evaporated under reduced pressure and saturated aqueous sodium hydrogencarbonate solution was added to the residue. After the extraction with ethyl acetate followed by washing with saturated aqueous sodium chloride solution and drying over sodium sulfate, the solvent was evaporated. 503 mg (1.81 mmol) of 2-cyanoethyl 2-acetyl-3-(3-chlorophenyl)acrylate and 30 ml of 2-propanol were added to the residue, and they were stirred under heating at 70° C. overnight. 2-Propanol was evaporated under reduced pressure, and the residue was purified by the silica gel chromatography (hexane/ethyl acetate=2/1) to obtain the title compound.

Yield: 189 mg (0.27 mmol) (14.7%) 1H-NMR (CDCl3): 2.64 (3H, s), 2.32 (2H, q), 2.63 (2H, t), 3.65–3.73 (4H, m), 3.91 (1H, t), 3.90–4.00 (2H, m), 4.24–4.32 (2H, m), 4.60 (2H, s), 4.71 (1H, d), 4.78 (1H, d), 4.98 (1H, s), 7.08–7.38 (19H, m), 7.64 (1H, bs)

4) Synthesis of 3-(3,3-diphenylpropane-1-yl)2-(2-benzyloxyethoxymethyl)-4-(3-chlorophenyl)-6-methyl-1,4-dihydropyridine-3,5-dicarboxylate:

75.0 mg (0.106 mmol) of 5-(2-cyanoethyl)3-(3,3-diphenylpropane-1-yl)2-(2-benzyloxyethoxymethyl)-4-(3-chlorophenyl)-6-methyl-1,4-dihydropyridine-3,5-dicarboxylate was dissolved in 4 ml of methanol. 212 µl of 1 N aqueous sodium hydroxide solution was added to the obtained solution, and they were stirred at room temperature for 3.5 hours. Methanol was evaporated under reduced pressure, and then 2 N hydrochloric acid and water were added to the residue to precipitate a yellow solid. The solid was collected by the filtration and then purified by the thin layer silica gel chromatography (hexane/ethyl acetate=2/1) to obtain the title compound.

Yield: 49.6 mg (0.076 mmol) (71.8%) MS (ESI, m/z) 650 (M−H)− 1H-NMR (CDCl3): 2.16 (3H, s), 2.32 (2H, q), 3.66–3.73 (4H, m), 3.88 (1H, t), 3.90–3.98 (2H, m), 4.59 (2H, s), 4.72 (1H, d), 4.79 (1H, d), 5.00 (1H, s), 7.04–7.36 (19H, m), 7.64 (1H, bs)

EXAMPLE 19

Synthesis of 3-(3,3-diphenylpropane-1-yl)2-(2-(azepane-1-yl)ethoxymethyl)-4-(3-chlorophenyl)-6-methyl-1,4-dihydropyridine-3,5-dicarboxylate:

1) Synthesis of (3,3-diphenylpropane-1-yl)4-(2-azepane-1-yl)ethoxy)-3-oxobutanoate:

2.5 ml of a solution of 410 mg (2.86 mmol) of 2-(azepane-1-yl)ethanol in THF was added dropwise to a suspension of 339 mg (8.46 mmol) of sodium hydride (60% oily) in 5 ml of THF at 0° C., and they were stirred at room temperature for 1 hour. 2.5 ml of a solution of 769 mg (2.32 mmol) of (3,3-diphenylpropane-1-yl)4-chloroacetoacetate in THF was added dropwise to the obtained mixture at 0° C., and they were stirred at room temperature overnight. THF was evaporated under reduced pressure. The residue was acidified with 2 N hydrochloric acid. After the extraction with methylene chloride, the extract was washed with saturated aqueous sodium hydrogencarbonate solution and saturated aqueous sodium chloride solution and then dried over sodium sulfate. Methylene chloride was evaporated under reduced pressure to obtain the title compound.

Yield: 929 mg (2.12 mmol) (91.3%) MS (ESI, m/z) 438 (M+H)+ 1H-NMR (CDCl3): 1.54–1.78 (8H, m), 2.40 (2H, q), 2.68–2.76 (4H, m), 2.75 (2H, t), 3.52 (2H, bs), 3.60 (2H, t), 4.05 (1H, t), 4.09 (2H, t), 4.13 (2H, s), 7.15–7.31 (10H, m)

2) Synthesis of 5-(2-cyanoethyl)3-(3,3-diphenylpropane-1-yl)2-(2-azepane-1-yl)ethoxymethyl)-4-(3-chlorophenyl)-6-methyl-1,4-dihydropyridine-3,5-dicarboxylate:

981 mg (2.24 mmol) of (3,3-diphenylpropane-1-yl)4-(2-(azepane-1-yl)ethoxy)-3-oxobutanoate and 529 mg (6.86 mmol) of ammonium acetate were stirred in 10 ml of 2-propanol under heating at 50° C. overnight. 2-Propanol was evaporated under reduced pressure. An aqueous saturated sodium hydrogencarbonate solution was added to the residue. After the extraction with ethyl acetate, the extract was washed with saturated aqueous sodium chloride solution and then dried over sodium sulfate. Ethyl acetate was evaporated under reduced pressure. 563 mg (2.03 mmol) of 2-cyanoethyl 2-acetyl-3-(3-chlorophenyl)acrylate and 50 ml of 2-propanol were added to the residue, and they were stirred under heating at 70° C. overnight. 2-Propanol was evaporated under reduced pressure, and the remaining product was purified by the silica gel chromatography (methylene chloride/methanol=95:5) to obtain the title compound.

Yield: 331 mg (0.48 mmol) (23.4%) MS (ESI, m/z) 696 (M+H)+ 1H-NMR (CDCl3): 1.50–1.75 (8H, m), 2.30–2.43 (2H, m), 2.40 (3H, s), 2.57–2.66 (4H, m), 2.70–2.85 (4H, m), 3.55–3.72 (2H, m), 3.85–4.00 (3H, m), 4.22–4.33 (2H, m), 4.68 (1H, d), 4.76 (1H, d), 4.99 (1H, s), 7.05–7.30 (14H, m), 8.08 (1H, s)

3) Synthesis of 3-(3,3-diphenylpropane-1-yl)2-(2-(azepane-1-yl)ethoxymethyl)-4-(3-chlorophenyl)-6-methyl-1,4-dihydropyridine-3,5-dicarboxylate:

331 mg (0.475 mmol) of 5-(2-cyanoethyl)3-(3,3-diphenylpropane-1-yl)2-(2-(azepane-1-yl)ethoxymethyl)-4-(3-chlorophenyl)-6-methyl-1,4-dihydropyridine-3,5-dicarboxylate was dissolved in 15 ml of methanol. 950 µl of 1 N aqueous sodium hydroxide solution was added to the obtained solution, and they were stirred at room temperature for 3.5 hours. Methanol was evaporated under reduced pressure. 2 N hydrochloric acid and water were added to the residue to precipitate a yellow solid. The solid was taken by the filtration and then purified by the thin layer silica gel chromatography (methylene chloride/methanol=10:1). The purified product was crystallized in hexane/ethyl acetate (3/1), and the crystals were taken by the filtration, washed and dried under reduced pressure to obtain the title compound.

Yield: 9.3 mg (0.0145 mmol) (3.1%) MS (ESI, m/z) 643 (M+H)+ 1H-NMR (CDCl3) 1.56–1.71 (8H, m), 2.22–2.32 (2H, m), 2.29 (3H, s), 2.70–2.88 (6H, m), 3.65–3.74 (2H, m), 3.85–3.95 (3H, m), 4.60 (1H, d), 4.88 (1H, d), 5.09 (1H, s), 7.02–7.32 (14H, m), 7.53 (1H, bs)

EXAMPLE 20

Synthesis of 3-(3,3-diphenylpropane-1-yl)4-(3-chlorophenyl)-2-(2-hydroxyethoxymethyl)-6-methyl-1,4-dihydropyridine-3,5-dicarboxylate 1) Synthesis of 3-(2-cyanoethyl)5-(3,3-diphenylpropane-1-yl)4-(3-chlorophenyl)-6-(2-hydroxyethoxymethyl)-2-methyl-1,4-dihydropyridine-3,5-dicarboxylate:

98.9 mg (0.140 mmol) of 3-(2-cyanoethyl)5-(3,3-diphenylpropane-1-yl)2-(2-benzyloxyethoxymethyl)-4-(3-chlorophenyl)-6-methyl-1,4-dihydropyridine-3,5-dicarboxylate was dissolved in 10 ml of ethyl acetate. The obtained solution was stirred in the presence of 5% palladium carbon in hydrogen atmosphere at room temperature for 4 days. 5% Palladium carbon was filtered out, and the filtrate was concentrated under reduced pressure to obtain the title compound.

Yield: 87.5 mg (0.142 mmol) (quantitative yield) MS (ESI, m/z) 613 (M−H)− 1H-NMR (CDCl3): 2.34 (2H, q), 2.38 (3H, s), 2.64 (2H, t), 3.66–3.71 (4H, m), 3.91–4.00 (3H, m), 4.23–4.35 (2H, m), 4.74 (1H, d), 4.81 (1H, d), 5.00 (1H, s), 7.08–7.30 (14H, m), 7.58 (1H, bs)

2) Synthesis of 3-(3,3-diphenylpropane-1-yl)4-(3-chlorophenyl)-2-(2-hydroxyethoxymethyl)-6-methyl-1,4-dihydropyridine-3,5-dicarboxylate:

The title compound was obtained from 87.5 mg (0.142 mmol) of 3-(2-cyanoethyl)5-(3,3-diphenylpropane-1-yl)4-(3-chlorophenyl)-6-(2-hydroxyethoxymethyl)-2-methyl-1,4-dihydropyridine-3,5-dicarboxylate in the same manner as that of Example 1-2).

Yield: 50.4 mg (0.09 mmol) (64.1%) MS (ESI, m/z) 562 (M+H)+ 1H-NMR (DMSO-d6): 2.25–2.34 (2H, m), 2.29 (3H, s), 3.45–3.60 (4H, m), 3.80–3.89 (3H, m), 4.63 (1H, d), 4.69 (1H, d), 4.97 (1H, s), 7.09–7.34 (14H, m), 8.58 (1H, bs)

EXAMPLE 21

Synthesis of (3,3-diphenylpropane-1-yl)4-(3-chlorophenyl)-5-(2-dimethylaminoethylcarbamoyl)-2,6-dimethyl-1,4-dihydropyridine-3-carboxylate 304 mg (0.60 mmol) of mono(3,3-diphenylpropane-1-yl) 4-(3-chlorophenyl)-2,6-dimethyl-1,4-dihydropyridine-3,5-dicarboxylate, 0.1 ml (0.91 mmol) of N,N-dimethylethylenediamine, 140 mg (0.73 mmol) of 1-(3-dimethylaminopropyl)-3-ethylcarbodiimide hydrochloride and 18 mg (0.15 mmol) of 4-dimethylaminopyridine were stirred in 10 ml of dichloromethane at room temperature overnight. Saturated aqueous sodium hydrogencarbonate solution was added to the reaction mixture. After the extraction with dichloromethane, the organic layer was dried over anhydrous sodium sulfate and then concentrated under reduced pressure. The residue was purified by the silica gel chromatography (chloroform/methanol=95/5) to obtain the title compound.

Yield: 257 mg (0.45 mmol) (74.9%) MS (ESI, m/z) 570 (M−H)− 1H-NMR (CDCl3): 2.08 (6H, s), 2.23–2.39 (4H, m), 2.26 (3H, s), 2.30 (3H, s), 3.13–3.34 (2H, m), 3.90–4.03 (3H, m), 4.76 (1H, s), 5.44 (1H, s), 6.08 (1H, s), 7.10–7.32 (14H, m)

EXAMPLE 22

Synthesis of (3,3-diphenylpropane-1-yl)4-(3-chlorophenyl)-5-cyano-2,6-dimethyl-1,4-dihydropyridine-3-carboxylate The title compound was obtained from 544 mg (1.84 mmol) of (3,3-diphenylpropane-1-yl)acetoacetate, 155 mg (1.89 mmol) of 3-aminocrotonitrile and 0.21 ml (1.85 mmol) of 3-chlorobenzaldehyde in the same manner as that of Example 1-1).

Yield: 560 mg (1.16 mmol) (63.0%) MS (ESI, m/z) 481 (M−H)− 1H-NMR (CDCl3): 2.09 (3H, s), 2.17–2.27 (2H, m), 2.39 (3H, s), 3.73 (1H, t), 3.91 (2H, t), 4.58 (1H, s), 5.77 (1H, s), 6.96–7.01 (2H, m), 7.11–7.30 (12H, m)

EXAMPLE 23

Synthesis of 3-(3,3-diphenylpropane-1-yl)4-(3-chlorophenyl)-2-methyl-6-(2-(piperidine-1-yl)ethoxymethyl)-1,4-dihydropyridine-3,5-dicarboxylate 1) Synthesis of benzyl 3-oxo-4-(2-(piperidine-1-yl)ethoxy)butanoate:

4.4 ml (33 mmol) of 2-(1-piperidine)ethanol was added dropwise to a suspension of 2.6 g (66 mmol) of sodium hydride (60% oily) in 150 ml of THF at 0° C., and the obtained mixture was stirred for 30 minutes. A solution of 5.00 g (22 mmol) of benzyl 4-chloroacetoacetate in 10 ml of THF was added dropwise to the reaction mixture at 0° C., and they were stirred at room temperature overnight. Methanol was added to them and the obtained mixture was concentrated and then fractionated with ethyl acetate and acidic water. The obtained extract was washed with saturated aqueous sodium hydrogencarbonate solution and saturated aqueous sodium chloride solution and then dried over sodium sulfate to obtain the title compound.

Yield: 6.56 g (20.5 mmol) (93.1%) MS (ESI, m/z) 320 (M+H)+ 1H-NMR (CDCl3): 1.43–1.46 (2H, m), 1.68–1.73 (4H, m), 2.64–2.68 (2H, m), 2.74 (2H, t), 3.54–3.58 (2H, m), 3.72 (2H, dd), 4.15 (2H, s), 5.17 (2H, s), 7.31–7.37 (5H, m)

2) Synthesis of benzyl 3-amino-4-(2-(piperidine-1-yl)ethoxy)crotonate:

The title compound was obtained from 500 mg (1.57 mmol) of benzyl 3-oxo-4-(2-(piperidine-1-yl)ethoxy)butanoate and 362 mg (4.70 mmol) of ammonium acetate in the same manner as that of Example 17-2).

Yield: 435 mg (1.37 mmol) (87.3%) MS (ESI, m/z) 319 (M+H)+ 1H-NMR (CDCl3): 1.43–1.47 (2H, m),1.54–1.61 (4H, m), 2.40–2.46 (4H, m), 2.52 (2H, t), 3.57 (2H, t), 4.08 (2H, s), 4.53 (1H, s), 5.12 (2H, s), 7.27–7.36 (5H, m)

3) Synthesis of 5-benzyl 3-(3,3-diphenylpropane-1-yl)4-(3-chlorophenyl)-2-methyl-6-(2-(piperidine-1-yl)ethoxymethyl)-1,4-dihydropyridine-3,5-dicarboxylate:

444 mg (1.5 mmol) of (3,3-diphenylpropane-1-yl)acetoacetate and 210 mg (1.5 mmol) of 3-chlorobenzaldehyde were stirred in the presence of catalytic amounts of acetic acid and piperidine in 9 ml of 2-propanol at room temperature overnight. 435 mg (1.37 mmol) of benzyl 3-amino-4-(2-(piperidine-1-yl)ethoxy)crotonate was added to the obtained mixture, and they were stirred under heating at 70° C. overnight. 2-Propanol was evaporated under reduced pressure, and the residue was purified by the silica gel chromatography (methylene chloride/methanol=100/1) to obtain the title compound.

Yield: 425 mg (0.59 mmol) (39%) MS (ESI, m/z) 719 (M+H)+ 1H-NMR (CDCl3): 1.41–1.51 (2H, m),1.57–1.67 (4H, m),2.29 (2H, dd), 2.42 (3H, s), 2.44–2.54 (4H, m), 3.57–3.72 (2H, m), 3.85–3.97 (3H, m), 4.66 (2H, dd), 5.10 (2H, dd), 5.30 (1H, s), 7.04–7.27 (19H, m), 7.74 (1H, s)

4) Synthesis of 3-(3,3-diphenylpropane-1-yl)4-(3-chlorophenyl)-2-methyl-6-(2-(piperidine-1-yl)ethoxymethyl)-1,4-dihydropyridine-3,5-dicarboxylate:

147 mg of 5-benzyl 3-(3,3-diphenylpropane-1-yl)4-(3-chlorophenyl)-2-methyl-6-(2-(piperidine-1-yl)ethoxymethyl)-1,4-dihydropyridine-3,5-dicarboxylate was violently stirred in the presence of a catalytic amount of 5% palladium carbon in 3 ml of ethyl acetate in hydrogen atmosphere 6 nights. After the filtration of rhe reaction mixture followed by the concentration and recrystallization from hexane/ethyl acetate, the title compound was obtained.

Yield: 21.5 mg (0.034 mmol) (39%) MS (ESI, m/z) 629 (M+H)+ 1H-NMR (CDCl3): 1.48–1.57 (2H, m), 1.60–1.72 (4H, m), 2.28–2.63 (11H, m), 2.42, 3.66–3.75 (2H, m), 3.81–3.96 (3H, m), 4.53 (1H, d), 4.79 (1H, d), 5.05 (1H, s), 7.00–7.35 (15H, m)

EXAMPLE 24

Synthesis of 3,3-diphenylpropane-1-yl5-(benzyloxycarbonylmethylcarbamoyl)-4-(3-chlorophenyl)-2,6-dimethyl-1,4-dihydropyridine-3-carboxylate The title compound was obtained from 304 mg (0.60 mmol) of mono(3,3-diphenylpropane-1-yl)4-(3-chlorophenyl)-2,6-dimethyl-1,4-dihydropyridine-3,5-dicarboxylate and 196 mg (1.19 mmol) of glycine benzyl ester in the same manner as that of Example 15.

Yield: 313 mg (0.48 mmol) (80.0%) MS (ESI, m/z) 647 (M−H)− 1H-NMR (CDCl3): 2.20–2.42 (2H, m), 2.26 (3H, s), 2.31 (3H, s), 3.90–4.08 (5H, m), 4.81 (1H, s), 5.15 (2H, s), 5.51 (1H, s), 5.87 (1H, t), 7.08–7.40 (19H, m)

EXAMPLE 25

Synthesis of (3,3-diphenylpropane-1-yl)4-(3-chlorophenyl)-2,6-dimethyl-5-(3-phenyl-2-propene-1-yl)carbamoyl-1,4-dihydropyridine-3-carboxylate The title compound was obtained from 301 mg (0.60 mmol) of mono(3,3-diphenylpropane-1-yl)4-(3-chlorophenyl)-2,6-dimethyl-1,4-dihydropyridine-3,5-dicarboxylate and 120 mg (0.90 mmol) of cinnamylamine in the same manner as that of Example 15.

Yield: 166 mg (0.27 mmol) (44.9%) MS (ESI, m/z) 615 (M−H)− 1H-NMR (CDCl3): 2.25 (3H, s), 2.31 (3H, s), 2.28–2.40 (2H, m), 3.90 (1H, t), 3.94–4.08 (4H, m), 4.80 (1H, s), 5.44 (1H, s), 5.49 (1H, s), 6.07 (1H, dt), 6.30 (1H, d), 7.06–7.32 (19H, m)

EXAMPLE 26

Synthesis of 5-(3,3-diphenyl-1-propyl)4-(3-chlorophenyl)-6-methyl-2-(2-(1-pyrrolidiine)ethoxy)methyl-1,4-dihydropyridine-3,5-dicarboxylate 1) Synthesis of benzyl 4-(2-(1-pyrrolidine)ethoxy)acetoacetate:

The title compound was obtained from 0.76 ml (6.6 mmol) of 2-(1-pyrrolidine)ethanol in the same manner as that of Example 23-2).

Yield: 1.14 g (3.74 mmol) (84.8%) MS (ESI, m/z) 306 (M+H)+ 1H-NMR (CDCl3): 1.90–1.92 (4H, m),2.89–2.92 (6H, m), 3.59 (2H, s), 3.76 (2H, t), 4.18 (2H, s), 5.17 (2H, s), 7.26–7.37 (5H, m)

2) Synthesis of benzyl 3-amino-4-(2-(1-pyrrolidine)ethoxy)crotonate:

The title compound was obtained from 1.14 g (3.74 mmol) of benzyl 4-(2-(1-pyrrolidine)ethoxy)acetoacetate in the same manner as that of Example 17-2).

Yield: 0.98 g (3.23 mmol) (86.2%) MS (ESI, m/z) 305 (M+H)+ 1H-NMR (CDCl3): 1.68–1.70 (2H, m), 2.53–2.57 (6H, m), 3.58 (2H, t), 4.54 (2H, s), 5.12 (2H, s), 7.26–7.38 (5H, m)

3) Synthesis of 3-benzyl 5-(3,3-diphenyl-1-propyl)4-(3-chlorophenyl)-6-methyl-2-(2-(1-pyrrolidine)ethoxy)methyl-1,4-dihydropyridine-3,5-dicarboxylate:

The title compound was obtained from 490 mg (1.62 mmol) of benzyl 3-amino-4-(2-(1-pyrrolidine)ethoxy)crotonate in the same manner as that of Example 23-3).

Yield: 484 mg (0.69 mmol) (37%) MS (ESI, m/z) 627 (M+H)+ 1H-NMR (CDCl3): 1.81–1.83 (4H, m), 2.38 (3H, s), 2.60–2.62 (6H, m), 3.66 (2H, dt), 4.66–4.84 (4H, m), 5.00 (1H, d), 5.04(1H, s), 5.12(1H, d), 6.21 (1H, dt), 6.51(1H, d), 7.07–7.33 (14H, m), 8.11 (1H, s)

4) Synthesis of 5-(3,3-diphenyl-1-propyl)4-(3-chlorophenyl)-6-methyl-2-(2-(1-pyrrolidine)ethoxy)methyl-1,4-dihydropyridine-3,5-dicarboxylate:

The title compound was obtained from 485 mg (0.69 mmol) of 3-benzyl 5-(3,3-diphenyl-1-propyl)4-(3-chlorophenyl)-6-methyl-2-(2-(1-pyrrolidine)ethoxy)methyl-1,4-dihydropyridine-3,5-dicarboxylate in the same manner as that of Example 23-4).

Yield: 64.9 mg (0.11 mmol) (15%) MS (ESI, m/z) 615 (M+H)+ 1H-NMR (CDCl3): 1.23–1.32 (4H, m),1.70–2.02 (6H, m), 2.27–2.34 (2H, m), 2.49(3H, s), 3.60–4.00 (5H, m), 4.69 (1H, d), 4.78 (1H, d), 5.04 (1H, s), 7.01–7.25 (14H, m), 7.71(1H, s)

EXAMPLE 27

Synthesis of 3,3-diphenylpropyl 5-(carboxymethylcarbamoyl)-4-(3-chlorophenyl)-2,6-dimethyl-1,4-dihydropyridine-3-carboxylate The title compound was obtained from 214 mg (0.33 mmol) of the compound obtained in Example 24 in the same manner as that of Example 23-4).

Yield: 171 mg (0.31 mmol) (93.9%) MS (ESI, m/z) 557 (M−H)− 1H-NMR (DMSO-d6): 2.06 (3H, s), 2.21–2.30 (2H, m), 2.29 (3H, s), 3.60–3.69 (1H, m), 3.73–3.83 (4H, m), 4.87 (1H, s), 7.05–7.31 (14H, m), 7.86 (1H, t), 8.49 (1H, s)

EXAMPLE 28

Synthesis of 3,3-diphenylpropyl5-(4-benzylpiperazine-1-carbonyl)-4-(3-chlorophenyl)-2,6-dimethyl-1,4-dihyddropyridine-3-carboxylate The title compound was obtained from 302 mg (0.60 mmol) of the compound obtained in Example 1 and 0.16 ml (0.90 mmol) of 1-benzylpiperazine in the same manner as that of Example 15.

Yield: 291 mg (0.44 mmol) (73.3%) MS (ESI, m/z) 658 (M−H)− 1H-NMR (CDCl3): 1.73 (3H, s), 2.00–3.25 (10H, m), 2.37 (3H, s), 3.34 (2H, d), 3.66 (1H, t), 3.73–3.88 (2H, m), 4.98 (1H, s), 5.18 (1H, s), 6.92 (2H, d), 7.09–7.33 (17H, m)

EXAMPLE 29

Synthesis of 3,3-diphenylpropyl 4-(3-chlorophenyl)-2,6-dimethyl-5-(piperazine-1-carbonyl)-1,4-dihydropyridine-3-carboxylate The title compound was obtained from 164 mg (0.25 mmol) of the compound obtained in Example 28 in the same manner as that of Example 23-4).

Yield: 38 mg (0.07 mmol) (28.0%) MS (ESI, m/z) 568 (M–H)– 1H-NMR (CDCl3): 1.74 (3H, s), 2.08–2.20 (2H, m), 2.37 (3H, s), 2.62–3.40 (6H, m), 3.63–3.70 (2H, m), 3.77–3.90 (3H, m), 4.96 (1H, s), 5.26 (1H, s), 6.93–7.28 (14H, m)

EXAMPLE 30

Synthesis of 5-(3,3-diphenyl-1-propyl)4-(3chlorophenyl)-2-methyl-6-(2-(1-pyrrolidine)ethoxy)methyl-1,4-dihydropyridine-3,5-dicarboxylate 1) Synthesis of 3,3-diphenyl-1-propyl4-(2-(1-pyrrolidine)ethoxy)acetoacetate:

2.5 ml of a solution of 327 mg (2.83 mmol) of 2-(1-pyrrolidine)ethanol in tetrahydrofuran was added dropwise to a suspension of 328 mg (8.19 mmol) of sodium hydride (60% oily) in 5 ml of tetrahydrofuran at 0° C., and they were stirred at room temperature for 2 hours. 2.5 ml of a solution of 780 mg (2.36 mmol) of 3,3-diphenyl-1-propyl 4-chloroacetoacetate in tetrahydrofuran was added dropwise to the reaction mixture at 0° C., and they were stirred at room temperature overnight. Tetrahydrofuran was evaporated under reduced pressure, and the residue was acidified with 2 N hydrochloric acid. After the extraction with dichloromethane, the extract was washed with a saturated aqueous sodium hydrogencarbonate solution and saturated aqueous sodium chloride solution and then dried over sodium sulfate. Dichloromethane was evaporated under reduced pressure to obtain the title compound.

Yield: 813 mg (1.99 mmol) (84.3%) MS (ESI, m/z) 410 (M+H)+ 1H-NMR (CDCl3): 1.76–1.80 (4H, m), 2.40(2H,q), 2.52–2.60 (4H, m), 2.71 (2H, t), 3.50 (2H, bs), 3.64 (2H, t), 4.00–4.16(3H, m), 4.13 (2H, s), 715–7.31 (10H, m)

2) Synthesis of 3-(2-cyanoethyl)5-(3,3-diphenyl-1-propyl) 4-(3-chlorophenyl)-2-methyl-6-(2-(1-pyrrolidine)ethoxy) methyl-1,4-dihydropyridine-3,5-dicarboxylate:

174 mg (0.425 mmol) of 3,3-diphenyl-1-propyl 4-(2-(1-pyrrolidine)ethoxy)acetoacetate and 111 mg (1.44 mmol) of ammonium acetate were stirred in 2 ml of 2-propanol under heating at 50° C. overnight. 2-Propanol was evaporated under reduced pressure and then a saturated aqueous sodium hydrogencarbonate solution was added to the residue. After the extraction with ethyl acetate, the extract was washed with saturated aqueous sodium chloride solution and then dried over sodium sulfate. The solvent was evaporated. 97.6 mg (0.351 mmol) of 2-cyanoethyl 2-acetyl-3-(3-chlorophenyl)acrylate and 5 ml of 2-propanol were added to the residue, and they were stirred under heating at 70° C. for 2 hours. 2-Propanol was evaporated under reduced pressure, and the residue was purified by the thin layer silica gel chromatography (dichloromethane/methanol=10:1) to obtain the title compound.

Yield: 52 mg (0.78 mmol) (22.6%) MS (ESI, m/z) 668 (M+H)+ 1H-NMR (CDCl3): 1.78–1.86(4H, m), 2.34 (2H, q), 2.38(3H, s), 2.60–2.64(4H, m), 3.59–3.76(2H, m), 3.91 (1H, t), 3.89–4.02(2H, m), 4.21–4.35(2H, m), 4.68(1H, d), 4.78(1H, d), 4.99(1H, s), 7.08–7.32(14H, m), 8.25 (1H, bs)

3) Synthesis of 5-(3,3-diphenyl-1-propyl)4-(3-chlorophenyl)-2-methyl-6-(2-(1-pyrrolidine)ethoxy)methyl-1,4-dihydropyridine-3,5-dicarboxylate:

The title compound was obtained from 63.1 mg (0.106 mmol) of 3-(2-cyanoethyl)5-(3,3-diphenyl-1-propyl)4-(3-chlorophenyl)-2-methyl-6-(2-(1-pyrrolidine)ethoxy)methyl-1,4-dihydropyridine-3,5-dicarboxylate in the same manner as that of Example 1-2).

Yield: 40 mg (0.07 mmol) (68.9%) MS (ESI, m/z) 615 (M+H)+ 1H-NMR (CDCl3): 1.80–1.96(4H, m), 2.20–2.36 (5H, m), 2.70–3.30(6H, m), 3.64–3.87(5H, m), 4.61 (1H, d), 4.88 (1H, d), 5.09 (1H, s), 7.04–7.36 (15H, m)

EXAMPLE 31

Synthesis of 3,3-diphenylpropyl 5-(2-benzyloxyethylcarbamoyl)-4-(3-chlorophenyl)-2,6-dimethyl-1,4-dihydropyridine-3-carboxylate The title compound was obtained from 303 mg (0.60 mmol) of the compound obtained in Example 1 and 141 mg (0.93 mmol) of 2-benzyloxyethylamine in the same manner as that of Example 15.

Yield: 351 mg (0.55 mmol) (91.7%) MS (ESI, m/z) 633 (M–H)– 1H-NMR (CDCl3): 2.19 (3H, s), 2.28–2.36 (2H, m), 2.31 (3H, s), 3.40–3.46 (4H, m), 3.86–4.00 (3H, m), 4.40 (2H, s), 4.79 (1H, s), 5.46 (1H, s), 5.74 (1H, s), 7.05–7.35 (19H, m)

EXAMPLE 32

Synthesis of 5-(3,3-diphenyl-1-propyl)4-(3-chlorophenyl)-6-methyl-2-(2-(1-morpholine)ethoxy)methyl-1,4-dihydropyridine-3,5-dicarboxylate:

1) Synthesis of benzyl 4-(2-(1-morpholine)ethoxy)acetoacetate:

The title compound was obtained from 0.43 g (3.3 mmol) of 2-(1-morpholine)ethanol in the same manner as that of Example 23-1).

Yield: 0.57 g (1.77 mmol) (61.2%) MS (ESI, m/z) 322 (M+H)+ 1H-NMR (CDCl3): 2.60–2.76 (2H, m), 3.56 (2H, s), 3.66 (2H, t), 3.76 (4H, t), 4.14 (2H, s), 5.17(2H, s), 7.26–7.47 (5H, m)

2) Synthesis of benzyl 3-amino-4-(2-(1-morphoine)ethoxy) crotonate:

The title compound was obtained from 0.57 g (1.77 mmol) of benzyl 4-(2-(1-morpholine)ethoxy)acetoacetate in the same manner as that of Example 17-2).

Yield: 0.42 g (1.31 mmol) (73%) MS (ESI, m/z) 321 (M+H)+ 1H-NMR (CDCl3): 2.50 (4H, t), 2.57 (2H, t), 3.57 (2H, t), 3.71(4H, t), 4.07 (2H, s), 4.52 (1H, s), 5.12 (2H, s), 7.26–7.36 (5H, m)

3) Synthesis of 3-benzyl 5-(3,3-diphenyl-1-propyl)4-(3-chlorophenyl)-6-methyl-2-(2-(1-morpholine)ethoxy)methyl-1,4-dihydropyridine-3,5-dicarboxy-late:

The title compound was obtained from 418 mg (1.31 mmol) of benzyl 3-amino-4-(2-(1-morpholine)ethoxy)crotonate in the same manner as that of Example 23-3).

Yield: 401 mg (0.56 mmol) (45%) MS (ESI, m/z) 721 (M+H)+ 1H-NMR (CDCl3): 2.28–2.30 (2H, m), 2.41 (3H, s), 2.51 (4H, t), 2.61 (4H, m), 3.62–3.75 (6H, m), 3.86–3.97 (3H, m), 4.70 (1H, d), 4.75(1H, d), 5.07 (1H, s), 5.11(2H, s), 7.04–7.29 (20H, m)

4) Synthesis of 5-(3,3-diphenyl-1-propyl)4-(3-chlorophenyl)-6-methyl-2-(2-(1-morpholine)ethoxy)methyl-1,4-dihydropyridine-3,5-dicarboxylate:

The title compound was obtained from 200 mg (0.27 mmol) of 3-benzyl 5-(3,3-diphenyl-1-propyl)4-(3-chlorophenyl)-6-methyl-2-(2-(1-morpholine)ethoxy)methyl-1,4-dihydropyridine-3,5-dicarboxylate in the same manner as that of Example 23-4).

Yield: 98 mg (0.14 mmol) (57%) MS (ESI, m/z) 631 (M+H)+ 1H-NMR (CDCl3): 2.25–2.32 (2H, m), 2.42(3H, s), 2.48–2.65 (6H, m), 3.63–3.72 (6H, m), 3.86–3.95(3H, m), 4.62 (1H, d), 4.73 (1H, d), 5.01 (1H, s), 7.05–7.44 (15H, m)

EXAMPLE 33

Synthesis of 5-(3,3-diphenyl-1-propyl)4-(3-chlorophenyl)-2-methyl-6-(2-(3-pyridine)ethoxy)methyl-1,4-dihydropyridine-3,5-dicarboxylate 1) Synthesis of 3,3-diphenylpropyl4-(2-(3-pyridine)ethoxy) acetoacetate:

The title compound was obtained from 419 mg (3.5 mmol) of 2-(3-pyridine)ethanol in the same manner as that of Example 30.

Yield: 940 mg (2.3 mmol) (99%) MS (ESI, m/z) 418 (M+H)+ 1H-NMR (CDCl3): 2.34–2.43 (2H, m), 2.86–2.95 (2H, m), 3.42 (2H, s), 3.69 (2H, t), 4.00–4.16 (5H, m), 7.15–7.28 (10H, m), 7.58 (1H, m), 8.48 (3H, m)

2) Synthesis of 3,3-diphenylpropyl3-amino-4-(2-(3-pyridine)ethoxy)crotonate:

The title compound was obtained from 940 mg (2.3 mmol) of 3,3-diphenylpropyl 4-(2-(3-pyridine)ethoxy)acetoacetate in the same manner as that of Example 17-2).

Yield: 928 mg (2.2 mmol) (97%) MS (ESI, m/z) 417 (M+H)+ 1H-NMR (CDCl3): 2.34–2.41 (2H, m), 3.11 (2H, ddd), 3.87 (1H, t), 3.99 (1H, t), 4.04–4.11 (3H, m), 4.46 (1H, t), 713–7.27 (10H, m), 7.59–7.64 (2H, m), 8.53–8.55 (2H, m)

3) Synthesis of 3-(2-cyanoethyl)5-(3,3-diphenyl-1-propyl) 4-(3-chlorophenyl)-2-methyl-6-(2-(3-pyridine)ethoxy)methyl-1,4-dihydro-pyridine-3,5-dicarboxylate:

The title compound was obtained from 356 mg (2.3 mmol) of cyanoethyl acetoacetate, 356 mg (2.5 mmol) of 3-chlorobenzaldehyde and 928 mg (2.2 mmol) of 3,3-dihenyl-1-propyl 3-amino-4-(2-(3-pyridine)ethoxy)crotonate in the same manner as that of Example 14-2).

Yield: 413 mg (0.61 mmol) (61%) MS (ESI, m/z) 719 (M+H)+ 1H-NMR (CDCl3): 1.41–1.51 (2H, m), 1.57–1.67 (4H, m), 2.29 (2H, dd), 2.42 (3H, s), 2.44–2.54 (4H, m), 3.57–3.72 (2H, m), 3.85–3.97 (3H, m), 4.66 (2H, dd), 5.10 (2H, dd), 5.30 (1H, s), 7.04–7.27 (19H, m), 7.74 (1H, s)

4) Synthesis of 5-(3,3-diphenyl-1-propyl)4-(3-chlorophenyl)-2-methyl-6-(2-(3-pyridine)ethoxy)methyl-1,4-dihydropyridine-3,5-dicarboxylate:

0.46 ml of 1 N sodium hydroxide solution was added to 160 mg (0.23 mmol) of 3-(2-cyanoethyl)5-(3,3-diphenyl-1-propyl)4-(3-chlorophenyl)-2-methyl-6-(2-(3-pyridine) ethoxy)methyl-1,4-dihydropyridine-3,5-dicarboxylate in 2 ml of methanol, and they were stirred at room temperature for 2 hours. Methanol was evaporated under reduced pressure. The residue was neutralized with 2 N hydrochloric acid, and water was added thereto. After the extraction with ethyl acetate, the organic layer was concentrated under reduced pressure, and the residue was purified by the silica gel chromatography to obtain the title compound.

Yield: 60 mg (0.10 mmol) (42%) MS (ESI, m/z) 623 (M+H)+ 1H-NMR (CDCl3): 2.27–2.33 (5H, m), 3.14 (2H, t), 3.88–3.99 (5H, m), 4.74 (2H, s), 5.00 (1H, s), 7.04–7.40 (15H, m), 7.63–7.65 (2H, m), 8.59–8.61 (2H, m)

EXAMPLE 34

Synthesis of 3,3-diphenylpropyl 4-(3-chlorophenyl)-5-(2-hydroxyethylcarbamoyl)-2,6-dimethyl-1,4-dihydropyridine-3-carboxylate The title compound was obtained from 234 mg (0.43 mmol) of the compound obtained in Example 31 in the same manner as that of Example 23-4).

Yield: 50 mg (0.09 mmol) (20.9%) MS (ESI, m/z) 543 (M−H)− 1H-NMR (CDCl3): 2.24 (3H, s), 2.30–2.38 (2H, m), 2.31 (3H, s), 3.28–3.41 (2H, m), 3.54–3.64 (2H, m), 3.88–4.02 (3H, m), 4.78 (1H, s), 5.55 (1H, s), 5.78 (1H, t), 7.10–7.29 (14H, m)

EXAMPLE 35

Synthesis of 3,3-diphenylpropyl 5-(4-benzyl-[1,4] diazepane-1-carbonyl)-4-(3-chlorophenyl)-2,6-dimethyl-1,4-dihydro-pyridine-3-carboxylate The title compound was obtained from 403 mg (0.80 mmol) of the compound obtained in Example 1 and 232 mg (1.22 mmol) of 1-benzyl-[1,4]diazepane in the same manner as that of Example 21.

Yield: 426 mg (0.63 mmol) (78.8%) MS (ESI, m/z) 674 (M+H)+ 1H-NMR (CDCl3): 1.50–3.40 (15H, m), 2.35 (3H, s), 3.44–3.98 (5H, m), 4.96 (1H, s), 5.24 (1H, s), 6.92–7.33 (19H, m)

EXAMPLE 36

Synthesis of 5-(3,3-diphenyl-1-propyl)4-(3-chlorophenyl)-2-methyl-6-(2-(1-morpholine)ethoxy)methyl-1,4-dihydropyridine-3,5-dicarboxylate 1) Synthesis of 3,3-diphenylpropyl4-(2-(1-morpholine) ethoxy) acetoacetate:

The title compound was obtained from 446 mg (3.40 mmol) of 2-(1-morpholine)ethanol in the same manner as that of Example 30.

Yield: 975 mg (2.3 mmol) (99%) MS (ESI, m/z) 418 (M+H)+ 1H-NMR (CDCl3): 2.34–2.45 (2H, m), 3.10 (2H, ddd), 3.42 (2H, s), 3.90 (1H, t), 4.00–4.12 (5H, m), 4.46 (1H, t), 711–7.26 (10H, m), 7.56–7.64 (2H, m), 8.51–8.54 (2H, m)

2) Synthesis of 3,3-diphenylpropyl 3-amino-4-(2-(1-morpholine) ethoxy)crotonate:

The title compound was obtained from 975 mg (2.3 mmol) of 3,3-diphenylpropyl 4-(2-(1-morpholine)ethoxy) acetoacetate in the same manner as that of Example 17-2).

Yield: 922 mg (2.2 mmol) (94%) MS (ESI, m/z) 417 (M+H)+ 1H-NMR (CDCl3): 2.34–2.41 (2H, m), 3.11 (2H, ddd), 3.87 (1H, t), 3.99 (1H, t), 4.04–4.11 (3H, m), 4.46 (1H, t), 713–7.27 (10H, m), 7.59–7.64 (2H, m), 8.53–8.55 (2H, m)

3) Synthesis of 3-cyanoethyl 5-(3,3-diphenyl-1-propyl)4-(3-chlorophenyl)-6-methyl-2-(2-(1-morpholine)ethoxy)methyl-1,4-dihydropyridine-3,5-dicarboxylate:

The title compound was obtained from 357 mg (2.3 mmol) of (2-cyanoethyl)acetoacetate, 388 mg (2.8 mmol) of 3-chlorobenzaldehyde and 922 mg (2.2 mmol) of 3,3-diphenylpropyl 3-amino-4-(2-(1-morpholine)ethoxy)crotonate in the same manner as that of Example 14-2).

Yield: 1.14 g (1.7 mmol) (77%) MS (ESI, m/z) 719 (M+H)+ 1H-NMR (CDCl3): 1.41–1.51 (2H, m), 1.57–1.67 (4H,m), 2.29 (2H, dd), 2.42 (3H, s), 2.44–2.54 (4H, m), 3.57–3.72 (2H, m), 3.85–3.97 (3H, m), 4.66 (2H, dd), 5.10 (2H, dd), 5.30 (1H, s), 7.04–7.27 (19H, m), 7.74 (1H, s)

4) Synthesis of 5-(3,3-diphenyl-1-propyl)4-(3-chlorophenyl)-2-methyl-6-(2-(1-morpholine)ethoxy)methyl-1,4-dihydropyridine-3,5-dicarboxylate:

The title compound was obtained from 142 mg (0.21 mmol) of 3-(2-cyanoethyl)5-(3,3-diphenyl-1-propyl)4-(3-chlorophenyl)-2-methyl-6-(2-(1-morpholine)ethoxy)-1,4-dihydropyridine-3,5-dicarboxylate in the same manner as that of Example 33-4).

Yield: 44 mg (0.07 mmol) (34%) MS (ESI, m/z) 623 (M+H)+ 1H-NMR (CDCl3): 2.27–2.33 (5H, m), 3.14 (2H, t), 3.88–3.99 (5H, m), 4.74 (2H, s), 5.00 (1H, s), 7.04–7.40 (15H, m), 7.63–7.65 (2H, m), 8.59–8.61 (2H, m)

EXAMPLE 37

Synthesis of 5-(3,3-diphenyl-1-propyl)4-(3-chlorophenyl)-6-methyl-2-(2-(3-pyridine)ethoxy)methyl-1,4-dihydropyridine-3,5-dicarboxylate 1) Synthesis of benzyl 4-(2-(3-pyridine)ethoxy)acetoacetate:

The title compound was obtained from 406 mg (3.3 mmol) of 2-(3-pyridine)ethanol in the same manner as that of Example 23-1).

Yield: 689 g (2.2 mmol) (99%) MS (ESI, m/z) 320 (M+H)+ 1H-NMR (CDCl3): 1.43–1.46 (2H, m), 1.68–1.73 (4H, m), 2.64–2.68 (2H, m), 2.74 (2H, t), 3.54–3.58 (2H, m), 3.72 (2H, dd), 4.15 (2H, s), 5.17 (2H, s), 7.31–7.37 (5H, m)

2) Synthesis of benzyl 3-amino-4-(2-(3-pyridine)ethoxy)crotonate:

The title compound was obtained from 689 mg (2.2 mmol) of benzyl 4-(2-(3-pyridine)ethoxy)acetoacetate in the same manner as that of Example 17-2).

Yield: 594 mg (1.9 mmol) (86.5%) MS (ESI, m/z) 319 (M+H)+ 1H-NMR (CDCl3): 1.43–1.47 (2H, m),1.54–1.61 (4H, m), 2.40–2.46 (4H, m), 2.52 (2H, t), 3.57 (2H, t), 4.08 (2H, s), 4.53 (1H, s), 5.12 (2H, s), 7.27–7.36 (5H, m)

3) Synthesis of 3-benzyl 5-(3,3-diphenyl-1-propyl)4-(3-chlorophenyl)-6-methyl-2-(2-(3-pyridine)ethoxy)methyl-1,4-dihydropyridine-3,5-dicarboxylate:

The title compound was obtained from 594 mg (1.9 mmol) of benzyl 3-amino-4-(2-(3-pyridine)ethoxy)crotonate in the same manner as that of Example 23-3).

Yield: 1.02 g (1.4 mmol) (75%) MS (ESI, m/z) 719 (M+H)+ 1H-NMR (CDCl3): 1.41–1.51 (2H, m), 1.57–1.67 (4H, m), 2.29 (2H, dd), 2.42 (3H, s), 2.44–2.54 (4H, m), 3.57–3.72 (2H, m), 3.85–3.97 (3H, m), 4.66 (2H, dd), 5.10 (2H, dd), 5.30 (1H, s), 7.04–7.27 (19H, m), 7.74 (1H, s)

4) Synthesis of 5-(3,3-diphenyl-1-propyl)4-(3-chlorophenyl)-6-methyl-2-(2-(3-pyridine)ethoxy)methyl-1,4-dihydropyridine-3,5-dicarboxylate:

The title compound was obtained from 145 mg (0.20 mmol) of 3-benzyl 5-(3,3-diphenyl-1-propyl)4-(3-chlorophenyl)-6-methyl-2-(2-(3-pyridine)ethoxy)methyl-1,4-dihydropyridine-3,5-dicarboxylate in the same manner as that of Example 23-4).

Yield: 12 mg (0.02 mmol) (10%) MS (ESI, m/z) 629 (M+H)+ 1H-NMR (CDCl3): 1.48–1.57 (2H, m), 1.60–1.72 (4H, m), 2.28–2.63 (11H, m), 2.42, 3.66–3.75 (2H, m), 3.81–3.96 (3H, m), 4.53 (1H, d), 4.79 (1H, d), 5.05 (1H, s), 7.00–7.35 (15H, m)

EXAMPLE 38

Synthesis of 3,3-diphenylpropyl 4-(3-chlorophenyl)-5-[1,4]diazepane-1-carboxyl)-2,6-dimethyl-1,4-dihydropyridine-3-carboxylate The title compound was obtained from 297 mg (0.44 mmol) of the compound obtained in Example 35 in the same manner as that of Example 23-4).

Yield: 56 mg (0.10 mmol) (21.8%) MS (ESI, m/z) 582 (M−H)− 1H-NMR (CDCl3): 1.78 (3H, s), 2.10–2.22 (2H, m), 2.37 (3H, s), 2.55–3.40 (10H, m), 3.71 (1H, t), 3.78–3.95 (2H, m), 4.96 (1H, s), 5.25 (1H, s), 6.96–7.28 (14H, m)

EXAMPLE 39

Synthesis of 3,3-diphenylpropyl 5-(4-benzyloxycarbonylpiperidine-1-carbonyl)-4-(3-chlorophenyl)-2,6-dimethyl-1,4-dihydropyridine-3-carboxylate The title compound was obtained from 304 mg (0.61 mmol) of the compound obtained in Example 1 and 306 mg (0.92 mmol) of benzyl piperidine-4-carboxylate in the same manner as that of Example 15.

Yield: 45 mg (0.06 mmol) (10.5%) MS (ESI, m/z) 702 (M−H)− 1H-NMR (CDCl3): 1.20–2.00 (4H, m), 1.73 (3H, s), 2.08–2.18 (2H, m), 2.37 (3H, s), 2.60–3.40 (3H, m), 3.64 (1H, t), 3.74–3.86 (2H, m), 3.90–4.76 (2H, m), 4.97 (1H, s), 5.10 (2H, s), 5.20 (1H, s), 6.88–7.28 (19H, m)

EXAMPLE 40

Synthesis of 3,3-diphenylpropyl 4-(3-chlorophenyl)-2,6-dimethyl-5-(4-phenylpiperazine-1-carboxyl)-1,4-dihydropyridine-3-carboxylate The title compound was obtained from 304 mg (0.61 mmol) of the compound obtained in Example 1 and 0.14 ml (0.92 mmol) of 1-phenylpiperazine in the same manner as that of Example 21.

Yield: 403 mg (0.62 mmol) (quantitative yield) MS (ESI, m/z) 645 (M−H)− 1H-NMR (CDCl3): 1.78 (3H, s), 2.10–2.18 (2H, m), 2.39 (3H, s), 2.78–3.40 (4H, m), 3.66 (1H, t), 3.77–3.86 (2H, m), 4.99 (1H, s), 5.24 (1H, s), 6.79–7.30 (23H, m)

EXAMPLE 41

Synthesis of mono(8,8-diphenyloctyl)4-(3-chlorophenyl)-2,6-dimethyl-1,4-dihydropyridine-3,5-dicarboxylate 1) Synthesis of ethyl 8-benzyloxyoctanoate:

403 mg (10.1 mmol) of sodium hydride (60% oily) was added to 1.102 g (10.2 mmol) of benzyl alcohol in 15 ml of DMF, and they were stirred for 30 minutes. 2.51 g (9.99 mmol) of ethyl 8-bromooctanoate was dissolved in 5 ml of DMF, and the obtained solution was added dropwise to the reaction mixture in ice bath. After stirring at room temperature for 1.5 hours, 2 N hydrochloric acid was added to the mixture. DMF was evaporated under reduced pressure. After the extraction with ethyl acetate, the organic layer was dried over anhydrous sodium sulfate and then concentrated under reduced pressure. The residue was purified by the silica gel chromatography (hexane/ethyl acetate=9/1/) to obtain the title compound.

Yield: 1.44 g (5.17 mmol) (51.8%) MS (ESI, m/z) 279 (M+H)+ 1H-NMR (CDCl3): 1.25 (3H, t), 1.20–1.68 (10H, m), 2.28 (2H, t), 3.42–3.50 (2H, m), 4.12 (2H, q), 4.50 (2H, s), 7.24–7.38 (5H, m)

2) Synthesis of 8-benzyloxy-1,1-diphenyloctanol:

Ethyl 8-benzyloxyoctanoate was dissolved in 15 ml of THF. 15 ml (30 mmol) of phenylmagnesium bromide (2 M THF solution) was added dropwise to the obtained solution in ice bath. After stirring at room temperature for 4 hours, a saturated aqueous ammonium chloride solution and then 1 N hydrochloric acid were added to the reaction mixture to terminate the reaction. After the extraction with ethyl acetate, the organic layer was dried over anhydrous sodium sulfate and then concentrated under educed pressure. The residue was purified by the silica gel chromatography (hexane/ethyl acetate=9/1) to obtain the title compound.

Yield: 1.75 g (4.50 mmol) (87.1%)

3) Synthesis of 8,8-diphenyl-1-octanol:

20 ml of ethanol and 1 ml of concentrated sulfuric acid were added to 1.525 g (3.92 mmol) of 8-benzyloxy-1,1-dihenyloctanol, and the hydrogenation was conducted in the presence of a catalytic amount of palladium/carbon (10%, dry) at 50° C. under 5 atm. After stirring overnight followed by the concentration under reduced pressure, water was added to the residue. After the extraction with ethyl acetate, the organic layer was dried over anhydrous sodium sulfate and then concentrated under reduced pressure to obtain the title compound.

Yield: 1.10 g (3.89 mmol) 99.4%.

4) Synthesis of (8,8-diphenyloctane-1-yl)acetoacetate:

0.3 ml (3.89 mmol) of diketene and 0.1 ml (0.72 mmol) of triethylamine were added to 532 mg (1.88 mmol) of 8,8-diphenyl-1-octanol in 10 ml of toluene, and they were stirred under heating at 80° C. for 6.5 hours. A saturated aqueous sodium hydrogencarbonate solution was added to the reaction mixture. After the extraction with ethyl acetate, the organic layer was dried over anhydrous sodium sulfate and then concentrated under reduced pressure to obtain the title compound.

Yield: 470 mg (1.28 mmol) (68.1%) MS (ESI, m/z) 365 (M–H)– 1H-NMR (CDCl3): 1.19–1.36 (8H, m), 1.54–1.66 (2H, m), 1.88–2.08 (2H, m), 2.26 (3H, s), 3.43 (2H, s), 3.87 (1H, t), 4.10 (2H, t), 7.12–7.30 (10H, m)

5) Synthesis of 3-(2-cyanoethyl)5-(8,8-diphenyloctane-1-yl) 4-(3-chlorophenyl)-2,6-dimmethyl-1,4-dihydropyridine-3,5-dicarboxylate:

The title compound was obtained from (8,8-diphenyloctane-1-yl)acetoacetate in the same manner as that of Example 1-1).

Yield: 235 mg (0.38 mmol) (29.6%) MS (ESI, m/z) 623 (M–H)– 1H-NMR (CDCl3): 1.12–1.62 (10H, m), 1.96–2.08 (2H, m), 2.34 (3H, s), 2.36 (3H, s), 2.61 (2H, t), 3.84–4.10 (3H, m), 4.18–4.32 (2H, m), 4.95 (1H, s), 5.66 (1H, s), 7.07–7.31 (14H, m)

6) Synthesis of mono(8,8-diphenyloctyl)4-(3-chlorophenyl)-2,6-dimethyl-1,4-dihydropyridine-3,5-dicarboxylate:

The title compound was obtained from 230 mg (0.37 mmol) of 3-(2-cyanoethyl)5-(8,8-diphenyloctane-1-yl)4-(3-chlorophenyl)-2,6-dimethyl-1,4-dihydropyridine-3,5-dicarboxylate in the same manner as that of Example 33-4).

Yield: 95 mg (0.17 mmol) (45.1%) MS (ESI, m/z) 570 (M–H)– 1H-NMR (DMSO-d6): 1.05–1.28 (8H, m), 1.38–1.52 (2H, m), 1.93–2.04 (2H, m), 2.24 (3H, s), 2.26 (3H, s), 3.82–4.03 (3H, m), 4.85 (1H, s), 7.06–7.32 (14H, m), 8.80 (1H, s)

EXAMPLE 42

Synthesis of 3,3-diphenylpropyl 4-(3-chlorophenyl)-2,6-dimethyl-5-[4-(pyridine-2-yl)piperazine-1-carbonyl]-1,4-dihydropyridine-3-carboxylate The title compound was obtained from 303 mg (0.60 mmol) of the compound obtained in Example 1 and 150 mg(0.92 mmol) of 1-(pyridine-2-yl)piperazine in the same manner as that of Example 21.

Yield: 309 mg (0.48 mmol) (80.0%) MS (ESI, m/z) 645 (M–H)– 1H-NMR (CDCl3): 1.77 (3H, s), 2.08–2.19 (2H, m), 2.40 (3H, s), 2.80–3.50 (8H, m), 3.66 (1H, t), 3.75–3.90 (2H, m), 4.99 (1H, s), 5.25 (1H, s), 6.54 (1H, d), 6.66 (1H, t), 6.92 (2H, d), 7.13–7.26 (12H, m), 7.47 (1H, t), 8.15 (1H, d)

EXAMPLE 43

Synthesis of 3,3-diphenylpropyl 5-(4-benzhydrylpiperazine-1-carbonyl)-4-(3-chlorophenyl)-2,6-dimethyl-1,4-dihydropyridine-3-carboxylate The title compound was obtained from 302 mg (0.60 mmol) of the compound obtained in Example 1 and 228 mg (0.90 mmol) of 1-benzhydrylpiperazine in the same manner as that of Example 21.

Yield: 400 mg (0.54 mmol) (90.0%) MS (ESI, m/z) 735 (M–H)– 1H-NMR (CDCl3): 1.73 (3H, s), 2.08–2.20 (2H, m), 2.36 (3H, s), 2.42–3.20 (8H, m), 3.60–3.71 (1H, m), 3.73–3.87 (2H, m), 4.04 (1H, s), 4.97 (1H, s), 5.16 (1H, s), 6.92 (2H, d), 7.01–7.33 (22H, m)

EXAMPLE 44

Synthesis of 5-(3,3-diphenyl-1-propyl)4-(3-chlorophenyl)-2-methyl-6-(2-(N-benzyloxycarbonyl-4-piperidine)ethoxy)methyl-1,4-dihydropyridine-3,5-dicarboxylate 1) Synthesis of 3,3-diphenylpropyl 4-(2-(N-benzyloxycarbonyl-4-piperidine)ethoxy)acetoacetate:

The title compound was obtained from 1.32 g (5.2 mmol) of 2-(N-benzyloxycarbonyl-4-piperidine)ethanol in the same manner as that of Example 30.

Yield: 680 mg (1.2 mmol) (31%) MS (ESI, m/z) 558 (M+H)+ 1H-NMR (CDCl3): 1.24–2.11 (7H, m), 2.37–2.41 (2H, m), 3.50–3.55 (4H, m), 4.05–4.20 (9H, m), 5.15 (2H, s) 7.26–7.37 (15H, m)

2) Synthesis of 3,3-diphenylpropyl 3-amino-4-(2-(N-benzyloxycarbonyl-4-piperidine)ethoxy)crotonate:

The title compound was obtained from 680 mg (1.2 mmol) of 3,3-diphenylpropyl 4-(2-(N-benzyloxycarbonyl-4-piperidine)ethoxy)acetoacetate in the same manner as that of Example 17-2).

Yield: 0.67 g (1.2 mmol) (99%) MS (ESI, m/z) 557 (M+H)+ 1H-NMR (CDCl3): 1.09–1.16 (3H, m), 1.68–1.70 (2H, m), 2.36–2.40 (2H, m), 2.43–2.81 (2H, m), 3.49 (2H, t), 4.00–4.19 (9H, m), 4.55 (1H, s), 5.12(2H, s) 7.14–7.37 (15H, m)

3) Synthesis of 3-(2-cyanoethyl)5-(3,3-diphenyl-1-propyl) 4-(3-chlorophenyl)-6-methyl-2-(2-(N-benzyloxycarbonyl-4-piperidine)ethoxy)methyl-1,4-dihydropyridine-3,5-dicarboxylate:

The title compound was obtained from 388 mg (2.5 mmol) of cyanoethyl acetoacetate, 421 mg (3.0 mmol) of 3-chlorobenzaldehyde and 678 mg (1.22 mmol) of 3,3-diphenyl-1-propyl 3-amino-4-(2-(N-benzyloxycarbonyl-4-piperidine)ethoxy)crotonate in the same manner as that of Example 14-2).

Yield: 723 mg (0.89 mmol) (74%) MS (ESI, m/z) 816 (M+H)+ 1H-NMR (CDCl3): 1.60–1.74 (5H, m), 2.32–2.35 (2H, m), 2.37 (3H, s), 2.42 (3H, s), 2.61–2.68 (2H, m), 2.70–2.89(2H, m) 3.51–3.96 (2H, m), 3.96–4.30 (9H, m), 4.66 (1H, s), 4.68 (1H, s), 4.99 (1H, s), 5.12(2H, s) 7.06–7.35 (20H, m)

4) Synthesis of 5-(3,3-diphenyl-1-propyl)4-(3-chlorophenyl)-2-methyl-6-(2-(N-benzyloxycarbonyl-4-piperidine)ethoxy)methyl-1,4-dihydro-pyridine-3,5-dicarboxylate:

The title compound was obtained from 313 mg (0.38 mmol) of 3-(2-cyanoethyl)5-(3,3-diphenyl-1-propyl)4-(3-chlorophenyl)-2-methyl-6-(2-(N-benzyloxycarbonyl-4-piperidine)ethoxy)methyl-1,4-dihydropyridine-3,5-dicarboxylate in the same manner as that of Example 33-4).

Yield: 272 mg (0.35 mmol) (93%) MS (ESI, m/z) 761 (M−H)− 1H-NMR (CDCl3): 1.66–1.77 (5H, m), 2.28–2.31 (2H, t), 2.32(3H, s), 2.74–2.76 (2H, m), 3.59 (2H, t), 3.87–4.16 (7H, m), 4.67(2H, d), 5.02(1H, s), 5.12(2H, s), 7.04–7.35 (15H, m)

EXAMPLE 45

Synthesis of 3,3-diphenylpropyl 5-(4-carboxypiperidine-1-carbonyl)-4-(3-chlorophenyl)-2,6-dimethyl-1,4-dihydropyridine-3-carboxylate The title compound was obtained from 35 mg (0.05 mmol) of the compound obtained in Example 39 in the same manner as that of Example 23-4).

Yield: 39 mg (0.06 mmol) (quantitative yield) MS (ESI, m/z) 612 (M−H)− 1H-NMR (CDCl3): 1.40–2.05 (4H, m), 1.73 (3H, s), 2.10–2.20 (2H, m), 2.37 (3H, s), 2.60–3.35 (3H, m), 3.62–3.94 (3H, m), 3.94–4.40 (2H, m), 4.96 (1H, s), 5.23 (1H, s), 6.91–7.26 (14H, m)

EXAMPLE 46

Synthesis of 3,3-diphenylpropyl 4-(3-chlorophenyl)-5-diisopropylcarbamoyl-2,6-dimethyl-1,4-dihydropyridine-3-carboxylate The title compound was obtained from 315 mg (0.63 mmol) of the compound obtained in Example 1 and 0.13 ml (0.93 mmol) of diisopropylamine in the same manner as that of Example 21.

Yield: 287 mg (0.49 mmol) (77.8%) MS (ESI, m/z) 585 (M+H)+ 1H-NMR (CDCl3): 0.86–2.57 (20H, m), 3.18–3.74 (2H, m), 3.84–4.05 (3H, m), 4.90 (1H, d), 5.69 (1H, d), 7.01–7.27 (14H, m)

EXAMPLE 47

Synthesis of 5-(3,3-diphenyl-1-propyl)4-(3-chlorophenyl)-2-methyl-6-(2-(4-piperidine)ethoxy)methyl-1,4-dihydropyridine-3,5-dicarboxylate The title compound was obtained from 210 mg (0.27 mmol) of the compound obtained in Example 44 in the same manner as that of Example 23-4).

Yield: 53 mg (0.08 mmol) (31%) MS (ESI, m/z) 629 (M+H)+ 1H-NMR (CDCl3): 1.48–1.57 (2H, m), 1.60–1.72 (4H, m), 2.28–2.63 (11H, m), 2.42, 3.66–3.75 (2H, m), 3.81–3.96 (3H, m), 4.53 (1H, d), 4.79 (1H, d), 5.05 (1H, s), 7.00–7.35 (15H, m)

EXAMPLE 48

Synthesis of 5-(3,3-diphenyl-1-propyl)4-(3-chlorophenyl)-2-methyl-6-(2-azidoethoxy)methyl-1,4-dihydropyridine-3,5-dicarboxylate 1) Synthesis of 3,3-diphenylpropyl 4-(2-chloroethoxy)acetoacetate:

A solution of 2.09 g (26 mmol) of 2-chloroethanol in 10 ml of tetrahydrofuran was added dropwise to a suspension of 1.84 g (46 mmol) of sodium hydride (60% oily) in 100 ml of tetrahydrofuran at −50° C., and they were stirred for 2 hours. A solution of 7.51 g (20 mmol) of 3,3-diphenylpropyl 4-bromoacetoacetate in 3 ml of tetrahydrofuran was added dropwise to the reaction mixture at −50° C. The temperature was elevated to room temperature, and they were stirred overnight. A small amount of hydrochloric acid was added to the reaction mixture. After the concentration followed by the fractionation with ethyl acetate and water, the extract was washed with 1 N sodium hydroxide and saturated aqueous sodium chloride solution and then dried over sodium sulfate to obtain the title compound.

Yield: 2.24 g (6.0 mmol) (30%) MS (ESI, m/z) 373 (M+H)+ 1H-NMR (CDCl3): 2.31–2.44 (2H, m), 3.51 (2H, s), 3.63 (2H, s), 3.78 (2H, t), 4.03–4.13 (3H, m), 7.16–7.31 (10H, m)

2) Synthesis of 3,3-diphenylpropyl 3-amino-4-(2-chloroethoxy)crotonate:

The title compound was obtained from 2.24 g (6.0 mmol) of 3,3-diphenylpropyl 4-(2-chloroethoxy)acetoacetate in the same manner as that of Example 17-2).

Yield: 2.26 g (6.0 mmol) (99%) MS (ESI, m/z) 374 (M+H)+ 1H-NMR (CDCl3): 2.31–2.42 (2H, m), 3.66 (2H, t), 3.73 (2H, t), 3.99–4.13 (5H, m), 4.55 (1H, s), 7.14–7.30 (10H, m)

3) Synthesis of 3-(2-cyanoethyl)5-(3,3-diphenyl-1-propyl) 4-(3-chlorophenyl)-6-methyl-2-(2-chloroethoxy)methyl-1, 4-dihydropyridine-3,5-dicarboxylate:

The title compound was obtained from 905 mg (6.0 mmol) of 2-cyanoethyl acetoacetate, 661 mg (6.0 mmol) of 3-chlorobenzaldehyde and 2.26 g (6.0 mmol) of 3,3-diphenyl-1-propyl 3-amino-4-(2-chloroethoxy)crotonate in the same manner as that of Example 14-2).

Yield: 2.09 g (3.28 mmol) (55%) MS (ESI, m/z) 633 (M+H)+ 1H-NMR (CDCl3): 2.30–2.37 (2H, m), 2.39 (3H, t), 2.65 (2H, t), 3.72–3.99 (7H, m), 4.78 (2H, dt), 4.79 (1H, d), 4.99 (1H, s), 7.08–7.36 (15H, m)

4) Synthesis of 3-(2-cyanoethyl)5-(3,3-diphenyl-1-propyl) 4-(3-chlorophenyl)-6-methyl-2-(2-azidoethoxy)methyl-1,4-dihydropyridine-3,5-dicarboxylate:

14.1 mg (0.09 mmol) of sodium iodide and 79.4 mg (1.22 mmol) of sodium azide were added to a solution of 592 mg (0.9 mmol) of 3-(2-cyanoethyl)5-(3,3-diphenyl-1-propyl)4-(3-chlorophenyl)-6-methyl-2-(2-chloroethoxy)methyl-1,4-dihydropyridine-3,5-dicarboxylate in DMF, and they were stirred at 50° C. overnight. After the extraction with ethyl acetate, the extract was washed with water and saturated aqueous sodium chloride solution, and dried over sodium sulfate to obtain the title compound.

Yield: 596 g (0.94 mmol) (99%) MS (ESI, m/z) 640 (M+H)+ 1H-NMR (CDCl3): 2.30–2.35 (2H, m), 2.38 (3H, s), 2.64 (2H, t), 3.50 (2H, dt), 3.76 (2H, dt), 3.90–3.96 (3H, m), 4.29 (2H, dt), 4.75 (1H, d), 4.79(1H, d), 4.99(1H, s), 7.08–7.28 (14H, m), 8.01(1H, s)

5) Synthesis of 5-(3,3-diphenyl-1-propyl)4-(3-chlorophenyl)-2-methyl-6-(2-azidoethoxy)methyl-1,4-dihydropyridine-3,5-dicarboxylate:

The title compound was obtained from 272 mg (0.43 mmol) of 3-(2-cyanoethyl)5-(3,3-diphenyl-1-propyl)4-(3-chlorophenyl)-2-methyl-6-(2-azidoethoxy)methyl-1,4-dihydropyridine-3,5-dicarboxylate in the same manner as that of Example 33-4).

Yield: 210 mg (0.37 mmol) (84%) MS (ESI, m/z) 585 (M+H)+ 1H-NMR (CDCl3): 2.22 (3H, s), 2.25–2.38 (2H, m), 3.42(2H, dt), 3.66–3.82 (5H, m), 4.67 (1H, d), 4.70(1H, d), 5.18 (1H, s), 7.19–7.27 (15H, m)

EXAMPLE 49

Synthesis of 5-(3,3-diphenyl-1-propyl)4-(3-chlorophenyl)-2-methyl-6-(2-aminoethoxy)methyl-1,4-dihydropyridine-3,5-dicarboxylate The title compound was obtained from 200 mg (0.34 mmol) of the compound obtained in Example 48 in the same manner as that of Example 23-4).

Yield: 138 mg (0.14 mmol) (72%) MS (ESI, m/z) 561 (M+H)+ 1H-NMR (CDCl3): 2.21–2.25 (5H, m), 2.72 (2H, t), 3.43 (2H, t), 3.74–3.81 (3H, m), 4.63 (1H, d), 4.66 (1H, d), 5.22 (1H, s), 7.01–7.31 (14H, m), 7.95(1H, s)

EXAMPLE 50

Synthesis of mono(3,3-diphenylpropyl)4-(3-carboxyphenyl)-2,6-dimethyl-1,4-dihydropyridine-3,5-dicarboxylate 1) Synthesis of 3-(2-cyanoethyl)5-(3,3-diphenylpropyl)4-(3-carboxyphenyl)-2,6-dimethyl-1,4-dihydropyridine-3,5-dicarboxylate:

753 mg (5.02 mmol) of 3-carboxybenzaldehyde, 1.49 g (5.02 mmol) of (3,3-diphenylpropyl)acetoacetate and 0.05 ml (0.51 mmol) of piperidine were stirred in 50 ml of benzene at 105° C. overnight. Ethyl acetate was added to the obtained mixture. After washing with 1 N hydrochloric acid and drying over anhydrous sodium sulfate, the reaction mixture was concentrated under reduced pressure. The residue was dissolved in 30 ml of 2-propanol. 775 mg (5.03 mmol) of 2-cyano 3-aminocrotonate was added to the obtained solution, and they were stirred at 80° C. overnight. After the concentration under reduced pressure, the residue was purified by the silica gel chromatography (chloroform/methanol=100/1) to obtain the title compound.

Yield: 629 mg (1.11 mmol) (22.1%) MS (ESI, m/z) 563(M−H)− 1H-NMR (DMSO-d6): 2.23–2.35 (2H, m), 2.28 (3H, s), 2.29 (3H, s), 2.73–2.90 (2H, m), 3.76–3.88 (3H, m), 4.18 (2H, t), 4.99 (1H, s), 7.09–7.28 (10H, m), 7.36 (1H, t), 7.46–7.50 (1H, m), 7.72–7.77 (1H, m), 7.86–7.88 (1H, m), 9.03 (1H, s)

2) Synthesis of mono(3,3-diphenylpropyl)4-(3-carboxyphenyl)-2,6-dimethyl-1,4-dihydropyridine-3,5-dicarboxylate:

311 mg (0.55 mmol) of 3-(2-cyanoethyl)5-(3,3-diphenylpropyl)4-(3-carboxyphenyl)-2,6-dimethyl-1,4-dihydropyridine-3,5-dicarboxylate was dissolved in 15 ml of methanol. 1.10 ml (1.10 mmol) of 1 N aqueous sodium hydroxide solution was added to the obtained solution, and they were stirred at room temperature for 6 hours. 1 N hydrochloric acid was added to the reaction mixture. The obtained mixture was concentrated under reduced pressure and water was added to the obtained residue. After the extraction with ethyl acetate, the organic layer was dried over anhydrous sodium sulfate and then concentrated under reduced pressure. Hexane was added to the residue to precipitate a solid, which was taken by the filtration, washed with hexane/ethyl acetate (3/1) and dried under reduced pressure to obtain the title compound.

Yield: 200.2 mg (0.39 mmol) (70.9%) MS (ESI, m/z) 510(M−H)− 1H-NMR (DMSO-d6): 2.24 (3H, s), 2.24–2.35 (2H, m), 2.29 (3H, s), 3.76–3.85 (3H, m), 4.99 (1H, s), 7.07–7.28 (10H, m), 7.34–7.45 (2H, m), 7.73–7.76 (1H, m), 7.88 (1H, s), 8.85(1H, s)

EXAMPLE 51

Synthesis of mono(2-benzhydryloxyethyl)4-(3-chlorophenyl)-2,6-dimethyl-1,4-dihydropyridine-3,5-dicarboxylate 1) Synthesis of 2-benzhydryloxyethanol:

8 ml of toluene and 2 drops of concentrated sulfuric acid were added to 621 mg (10.0 mmol) of ethylene glycol, and they were heated to 90° C. 737 mg (4.0 mmol) of benzhydrol was added dropwise to the obtained mixture for the duration of 50 minutes. 30 minutes after, 621 mg (10.0 mmol) of ethylene glycol was added thereto and they were stirred under heating for 40 minutes. Ether was added to the reaction mixture, and the organic layer was successively washed with water, saturated aqueous sodium hydrogencarbonate solution, water and finally saturated aqueous sodium chloride solution. The organic layer was dried over anhydrous magnesium sulfate and concentrated under reduced pressure. The residue was purified by silica gel chromatography (hexane/ethyl acetate=2/1) to obtain the title compound.

Yield: 873 mg (3.82 mmol) (95.6%) 1H-NMR (CDCl3): 2.04 (1H, t), 3.54–3.64 (2H, m), 3.74–3.83 (2H, m), 5.41 (1H, s), 7.22–7.38 (10H, m)

2) Synthesis of 3-(2-benzhydryloxyethyl)5-(2-cyanoethyl)4-(3-chlorophenyl)-2,6-dimethyl-1,4-dihydropyridine-3,5-dicarboxylate:

108 mg (0.30 mmol) of mono(2-cyanoethyl)4-(3-chlorophenyl)-2,6-dimethyl-1,4-dihydropyridine-3,5-dicarboxylate, 63 mg (0.33 mmol) of WSC hydrochloride and 75 mg (0.33 mmol) of 2-benzhydryloxyethanol were stirred in 4 ml of dichloromethane and 1 ml of DMF at room temperature overnight. After the addition of water followed by the extraction with ethyl acetate, the reaction product was washed with water, saturated aqueous ammonium chloride solution and saturated aqueous sodium chloride solution. The organic layer was dried over anhydrous magnesium sulfate and concentrated under reduced pressure. The residue was purified by the silica gel chromatography (hexane/ethyl acetate=1/1) to obtain the title compound.

MS (ESI, m/z) 569 (M–H)– 1H-NMR (CDCl3): 2.33 (3H, s), 2.37 (3H, s), 2.48 (2H, t), 3.63 (2H, t), 4.14–4.28 (4H, m), 5.00 (1H, s), 5.39 (1H, s), 5.70 (1H, s), 7.01–7.37

3) Synthesis of mono(2-benzhydryloxyethyl)4-(3-chlorophenyl)-2,6-dimethyl-1,4-dihydropyridine-3,5-dicarboxylate:

The title compound was obtained from 3-(2-benzhydryloxyethyl)5-(2-cyanoethyl)4-(3-chlorophenyl)-2,6-dimethyl-1,4-dihydropyridine-3,5-dicarboxylate in the same manner as that of Example 50-2).

Yield: 43 mg (0.08 mmol) (27.7%) (2 steps) MS (ESI, m/z) 516 (M–H)– 1H-NMR (DMSO-d6): 2.25 (3H, s), 2.28 (3H, s), 3.56 (2H, t), 4.08–4.19 (2H, m), 4.97 (1H, s), 5.47 (1H, s), 7.05–7.45 (14H, m), 8.86 (1H, s)

EXAMPLE 52

Synthesis of mono((2-benzhydryloxyethoxy)ethyl)4-(3-chlorophenyl)-2,6-dimethyl-1,4-dihydropyridine-3,5-dicarboxylate 1) Synthesis of 2-(2-benzhydryloxyethoxy)ethanol:

The title compound was obtained from 796 mg (7.5 mmol) of diethylene glycol in the same manner as that of Example 51-1).

Yield: 344 mg (1.26 mmol) (84.2%) 1H-NMR (CDCl3): 2.25 (1H, t), 3.59–3.67 (4H, m), 3.68–3.76 (4H, m), 5.41 (1H, s), 7.21–7.40 (10H, m)

2) Synthesis of 3-((2-benzhydryloxyethoxy)ethyl)5-(2-cyanoethyl)4-(3-chlorophenyl)-2,6-dimethyl-1,4-dihydropyridine-3,5-dicarboxylate:

The title compound was obtained from 90 mg (0.33 mmol) of 2-(2-benzhydryloxyethoxy)ethanol in the same manner as that of Example 51-2).

MS (ESI, m/z) 613 (M–H)– 1H-NMR (CDCl3): 2.30 (3H, s), 2.36 (3H, s), 2.54 (2H, t), 3.59–3.76 (6H, m),4.12–4.26 (4H, m), 4.98 (1H, s), 5.41 (1H, s), 5.68 (1H, s), 7.07–7.38 (14H, m)

3) Synthesis of mono((2-benzhydryloxyethoxy)ethyl)4-(3-chlorophenyl)-2,6-dimethyl-1,4-dihydropyridine-3,5-dicarboxylate:

The intended compound was obtained from 3-((2-benzhydryloxyethoxy)ethyl 5-(2-cyanoethyl)4-(3-chlorophenyl)-2,6-dimethyl-1,4-dihydropyridine-3,5-dicarboxylate in the same manner as that of Example 50-2).

Yield: 19 mg (0.03 mmol) (11.0%) (2 steps) MS (ESI, m/z) 560 (M–H)– 1H-NMR (DMSO-d6): 2.25 (3H, s), 2.27 (3H, s), 3.44–3.54 (2H, m), 3.56–3.66 (4H, m), 4.02–4.18 (2H, m), 4.88 (1H, s), 5.46 (1H, s), 7.05–7.38 (14H, m), 8.82 (1H, s)

EXAMPLE 53

Synthesis of 3,3-diphenylpropyl 5-(4-benzyl-[1,4]diazepane-1-carbonyl)-4-(3-carboxyphenyl)-2,6-dimethyl-1,4-dihydropyridine-3-carboxylate 1) Synthesis of 2-(2-cyanoethoxycarbonyl)benzaldehyde:

1.51 g (10.0 mmol) of 3-carboxybenzaldehyde, 1.85 g (26.0 mmol) of ethylene cyanohydrin, 4.99 g (26.2 mmol) of WSC hydrochloride, 1.82 ml (13.1 mmol) of triethylamine and 1.49 g (11.0 mmol) of HOBt were stirred in 20 ml of dichloromethane at room temperature overnight. 1 N hydrochloric acid was added to the reaction mixture. After extraction with dichloromethane, the organic layer was dried over anhydrous sodium sulfate, and concentrated under reduced pressure to obtain the title compound.

Yield: 2.24 g (11.0 mmol) (quantitative yield) 1H-NMR (CDCl3): 2.89 (2H, t), 4.59 (2H, t), 7.67 (1H, t), 8.11–8.17 (1H, m), 8.30–8.35 (1H, m), 8.54–8.56 (1H, m), 10.09 (1H, s)

2) Synthesis of 2-cyanoethyl 3-[2-(4-benzyl-[1,4]-diazepane-1-carbonyl)-3-oxobutenyl]benzoate:

1.12 g (5.00 mmol) of 3-(2-cyanoethoxycarbonyl)benzaldehyde, 1.38 g (5.03 mmol) of 1-(4-benzyl[1,4]-diazepane-1-yl)butane-1,3-dion and 0.05 ml (0.51 mmol) of piperidine were stirred in 50 ml of benzene at 105° C. overnight. Ethyl acetate was added to the reaction mixture. After drying over anhydrous sodium sulfate, the product was concentrated under reduced pressure to obtain the title compound.

Yield: 2.58 g (5.61 mmol) (quantitative yield) MS (ESI, m/z) 460 (M+H)+

3) Synthesis of 3,3-diphenylpropyl (5-(4-benzyl-[1,4]diazepane-1-carbonyl)-4-[3-(2-cyanoethoxycarbonyl)phenyl]-2,6-dimethyl-1,4-dihydropyridine-3-carboxylate:

2.05 g (3.99 mmol) of 2-cyanoethyl 3-[2-(4-benzyl-[1,4] diazepane-1-carbonyl)-3-oxobutenyl]benzoate and 1.18 g (3.99 mmol) of (3,3-diphenylpropyl)3-aminocrotonate were stirred in 40 ml of 2-propanol at 80° C. overnight. After the concentration under reduced pressure, the product was purified by the silica gel chromatography (chloroform/methanol=100/1) to obtain the title compound.

Yield: 328 mg (0.44 mmol) (11.0%) MS (ESI, m/z) 736 (M–H)– 1H-NMR (CDCl3): 1.80 (3H, s), 2.12–2.22 (2H, m), 2.37 (3H, s), 2.62–3.90 (17H, m), 4.34–4.44 (2H, m), 4.96 (1H, s), 5.33 (1H, s), 6.94–7.98 (19H, m)

4) Synthesis of 3,3-diphenylpropyl 5-(4-benzyl-[1,4]diazepane-1-carbonyl)-4-(3-carboxyphenyl)-2,6-dimethyl-1,4-dihydropyridine-3-carboxylate:

The title compound was obtained from 323 mg (0.44 mmol) of 3,3-diphenylpropyl (5-(4-benzyl-[1,4]diazepane-1-carbonyl)-4-[3-(2-cyano-ethoxycarbonyl)phenyl]-2,6-dimethyl-1,4-dihydropyridine-3-carboxylate in the same manner as that of Example 33-4).

Yield: 28.1 mg (0.04 mmol) (9.1%) MS (ESI, m/z) 683 (M–H)– 1H-NMR (DMSO-d6): 1.69 (3H, s), 2.07–2.18 (2H, m), 2.29 (3H, s), 2.43–3.82 (15H, m), 4.82 (1H, s), 6.91–7.83 (19H, m), 8.38 (1H,s)

EXAMPLE 54

Synthesis of 5-(3,3-diphenylpropyl)4-(3-chlorophenyl)-2-methyl-6-(2-[pyridine-4-yl]ethoxymethyl)-1,4-dihydropyridine-3,5-dicarboxylate 1) Synthesis of (3,3-diphenylpropyl)4-(2-[pyridine-4-yl]ethoxy)-3-oxobutanoate:

The title compound was obtained from 1.57 g (12.7 mmol) of 2-(4-pyridyl)ethanol in the same manner as that of Example 30.

Yield: 1.88 g (4.50 mmol) (35.3%) MS (ESI, m/z) 416 (M−H)− 1H-NMR (CDCl3): 2.31–2.43 (3H, m), 2.89 (2H, t), 3.42 (2H, s), 3.73 (2H, t), 4.00–4.10 (4H, m), 7.13–7.31 (12H, m), 8.49–8.51 (2H, m)

2) Synthesis of 3-(2-cyanoethyl)5-(3,3-diphenylpropyl)4-(3-chloro-phenyl)-2-methyl-6-(2-[pyridine-4-yl]ethoxymethyl)-1,4-dihydropyridine-3,5-dicarboxylate:

10 ml of 2-propanol and 1.07 g (13.9 mmol) of ammonium acetate were added to 1.88 g (4.50 mmol) of (3,3-diphenylpropyl)4-(2-[pyridine-4-yl]ethoxy)-3-oxobutanoate, and they were stirred at 50° C. for 4 hours. After the concentration under reduced pressure, ethyl acetate was added to the reaction mixture. The obtained mixture was washed with water and then saturated aqueous sodium hydrogencarbonate solution. The organic layer was dried over anhydrous sodium sulfate and then concentrated under reduced pressure. 18 ml of 2-propanol and 1.05 g (3.70 mmol) of 2-cyanoethyl 2-acetyl-3-(3-chlorophenyl)acrylate were added to the residue, and they were stirred at 80° C. three nights. After the concentration under reduced pressure, the residue was purified by the silica gel chromatography to obtain the title compound.

Yield: 1.87 g (2.76 mmol) (74.6%) MS (ESI, m/z) 674 (M−H)− 1H-NMR (CDCl3): 2.18 (3H, s), 2.29–2.34 (2H, m), 2.63 (2H, t), 2.96 (2H, t), 3.80–3.98 (5H, m), 4.24–4.30 (2H, m), 4.70 (2H, s), 4.96 (1H, s), 6.81 (1H, s), 7.07–7.26 (16H, m), 8.56–8.58 (2H, m)

3) Synthesis of 5-(3,3-diphenylpropyl)4-(3-chlorophenyl)-2-methyl-6-(2-[pyridine-4-yl]ethoxymethyl)-1,4-dihydropyridine-3,5-dicarboxylate:

The title compound was obtained from 1.87 g (2.76 mmol) of 3-(2-cyanoethyl)5-(3,3-diphenylpropyl)4-(3-chlorophenyl)-2-methyl-6-(2-[pyridine-4-yl]ethoxymethyl)-1,4-dihydropyridine-3,5-dicarboxylate in the same manner as that of Example 33-4).

Yield: 878.9 mg (1.41 mmol) (50.9%) MS (ESI, m/z) 621 (M−H)− 1H-NMR (CDCl3): 2.18 (3H, s), 2.28–2.35 (2H, m), 2.96 (2H, t), 3.78–3.98 (5H, m), 4.72 (2H, s), 5.00 (1H, s), 6.82 (1H, s), 7.04–7.27 (16H, m), 8.56–8.58 (2H, m)

EXAMPLE 55

Synthesis of 3-(3,3-diphenylpropyl)4-(3-chlorophenyl)-2-(2,2-dimethyl-[1,3]dioxalone-4-ylmethoxymethyl)-6-methyl-1,4-dihydro-pyridine-3,5-dicarboxylate 1) Synthesis of 5-(2-cyanoethyl)3-(3,3-diphenylpropyl)4-(3-chloro-phenyl)-2-(2,2-dimethyl-[1,3]dioxolane-4-yl-methoxymethyl)-6-methyl-1,4-dihydropyridine-3,5-dicarboxylate:

The title compound was obtained from a compound obtained from 397 mg (3.00 mmol) of (3,3-dimethyl-2,4-dioxyanyl)-1-methanol according to Example 30 in the same manner as that of Example 1-1.

Yield: 127 mg (0.186 mmol) (37.4%) 1H-NMR (CDCl3): 1.40 (3H, s), 1.43 (3H, s), 2.23–2.40 (5H, m), 2.63 (2H, t), 3.49–4.40 (10H, m), 4.75 (2H, q), 4.99 (1H, s), 7.08–7.40 (14H, m), 7.55 (1H, s)

2) Synthesis of 3-(3,3-diphenylpropyl)4-(3-chlorophenyl)-2-(2,2-dimethyl-[1,3]dioxolane-4-ylmethoxymethyl)-6-methyl-1,4-dihydro-pyridine-3,5-dicarboxylate:

The title compound was obtained from 127 mg (0.186 mmol) of 5-(2-cyanoethyl)3-(3,3-diphenylpropyl)4-(3-chlorophenyl)-2-(2,2-dimethyl-[1,3]dioxolane-4-ylmethoxymethyl)-6-methyl-1,4-dihydropyridine-3,5-dicarboxylate in the same manner as that of Example 50-2).

Yield: 65 mg (0.103 mmol) (55.4%) MS (ESI, m/z) 630 (M−H)− 1H-NMR (CDCl3): 1.39 (3H, s), 1.47 (3H, s), 2.29–2.40 (5H, m), 3.52–4.16 (7H, m), 4.34 (1H, m), 4.78 (2H, q), 5.01 (1H, s), 7.04–7.28 (14H, m), 7.51 (1H, d)

EXAMPLE 56

Synthesis of 3-(3,3-diphenylpropyl)4-(3-chlorophenyl)-2-(2-(2,2-dimethyl-[1,3]dioxolane-4-ylmethoxy)ethoxymethyl)-6-methyl-1,4-dihydropyridine-3,5-dicarboxylate:

1) Synthesis of 5-(2-cyanoethyl)3-(3,3-diphenylpropyl)4-(3-chlorophenyl)-2-(2-(2,2-dimethyl-[1,3]dioxolan-4-yl-methoxy)ethoxy-methyl)-6-methyl-1,4-dihydropyridine-3,5-dicarboxylate:

The title compound was obtained from a compound obtained from 397 mg (3.00 mmol) of (3,3-dimethyl-2,4-dioxyanyl)-1-methanol and 750 mg (2.15 mmol) of 3,3-diphenyl-1-propyl 4-(2-chloroethoxy)acetoacetate according to Example 30 in the same manner as that of Example 1-1).

Yield: 111 mg (0.164 mmol) (25.8%) 1H-NMR (CDCl3): 1.36 (3H, s), 1.43 (3H, s), 2.33 (2H, q), 2.38 (3H, s), 2.64 (2H, t), 3.52–3.75 (8H, m), 3.88–4.10 (4H, m), 4.24–4.36 (3H, m), 4.74 (2H, q), 4.99 (1H, s), 7.07–7.30 (14H, m), 7.48 (1H, brs)

2) Synthesis of 3-(3,3-diphenylpropyl)4-(3-chlorophenyl)-2-(2-(2,2-dimethyl-[1,3]dioxolane-4-ylmethoxy) ethoxymethyl)-6-methyl-1,4-dihydropyridine-3,5-dicarboxylate:

The title compound was obtained from 111 mg (0.164 mmol) of 5-(2-cyanoethyl)3-(3,3-diphenylpropyl)4-(3-chlorophenyl)-2-(2-(2,2-dimethyl-[1,3]dioxolane-4-ylmethoxy) ethoxymethyl)-6-methyl-1,4-dihydropyridine-3,5-dicarboxylate in the same manner as that of Example 50-2).

Yield: 48 mg, (0.071 mmol) (43.4%) MS (ESI, m/z) 674(M−H)− 1H-NMR (CDCl3): 1.35 (3H, s), 1.42 (3H, s), 2.32 (2H, q), 2.38 (3H, s), 3.51–3.78 (8H, m), 3.84–4.16 (4H, m), 4.31 (1H, m), 4.75 (2H, q), 5.02 (1H), s), 7.03–7.30 (14H, m), 7.49 (1H, s)

EXAMPLE 57

Synthesis of 5-(3,3-diphenylpropyl)4-(3-chlorophenyl)-2-methyl-6-trifluoromethyl-1,4-dihydropyridine-3,5-dicarboxylate:

1) Synthesis of 5-benzyl 3-(2-cyanoethyl)4-(3-chlorophenyl)-2-methyl-6-trifluoromethyl-1,4-dihydropyridine-3,5-dicarboxylate:

3.35 g (11.8 mmol) of benzyl 4,4,4-trifluoro-3-oxobutanoate, 1.60 g (11.8 mmol) of 3-chlorobenzaldehyde and 1.76 g (11.8 mmol) of 2-cyanoethyl 3-aminocrotonate were stirred in 35 ml of 1,2-dichloroethane at 75° C. overnight. 5.7 g of silica gel containing phosphoryl chloride and pyridine adsorbed thereon (prepared by a method described in Tetrahedron Lett., 1996, 37, 4177) was added to the obtained mixture, and they were stirred overnight. Silica gel was filtered out and then the solvent was evaporated under reduced pressure. The residue was purified by the silica gel chromatography (ethyl acetate/hexane=1/2) to obtain the title compound.

Yield: 3.75 g (7.52 mmol) (63.7%) 1H-NMR (CDCl3): 2.39 (3H, s), 5.02 (1H, s), 5.13 (2H, d-d), 6.20 (1H, bs), 7.06–7.38 (9H, m)

2) Synthesis of 3-(2-cyanoethyl)4-(3-chlorophenyl)-2-methyl-6-trifluoromethyl-1,4-dihydropyridine-3,5-dicarboxylate:

The title compound was obtained from 1.1 g (22.1 mmol) of 5-benzyl 3-(2-cyanoethyl)-4-(3-chlorophenyl)-2-methyl-6-trifluoromethyl-1,4-dihydropyridine-3,5-dicarboxylate in the same manner as that of Example 23-4).

Yield: 1.08 g (26.4 mmol) 1H-NMR (CDCl3): 2.44 (3H, s), 2.64 (2H, t), 4.29 (2H, m), 5.06 (1H, s), 6.38 (1H, bs), 7.18–7.25 (4H, m)

3) Synthesis of 3-(2-cyanoethyl)5-(3,3-diphenylpropyl)4-(3-chlorophenyl)-2-methyl-6-trifluoromethyl-1,4-dihydropyridine-3,5-dicarboxylate:

204 mg (0.50 mmol) of 3-(2-cyanoethyl)4-(3-chlorophenyl)-2-methyl-6-trifluoromethyl-1,4-dihydropyridine-3,5-dicarboxylate, 106 mg (0.5 mmol) of 3,3-diphenylpropyl alcohol, 6 mg (0.05 mmol) of DMAP and 105 mg (0.55 mmol) of WSC.HCl were dissolved in 1 ml of dichloromethane. 101 mg (1.0 mmol) of triethylamine was added to the obtained solution, and they were stirred overnight. Water was added thereto. After the extraction with ethyl acetate three times, the extract was dried over anhydrous sodium sulfate. The solvent was evaporated under reduced pressure. The residue was purified by the thin layer silica gel chromatography (ethyl acetate/hexane=1/1) to obtain the title compound.

Yield: 240 mg (0.40 mmol) (80.0%) 1H-NMR (CDCl3): 2.33 (2H, q), 2.43 (3H, s), 2.63 (2H, t), 3.90 (1H, t), 4.06 (2H, t), 7.28 (2H, m), 5.03 (1H, s), 6.20 (1H, bs), 7.14–7.32 (14H, m)

4) Synthesis of 5-(3,3-diphenylpropyl)4-(3-chlorophenyl)-2-methyl-6-trifluoromethyl-1,4-dihydropyridine-3,5-dicarboxylate:

The title compound was obtained from 122 mg (0.20 mmol) of 3-(2-cyanoethyl)4-(3-chlorophenyl)-2-methyl-6-trifluoromethyl-1,4-dihydro-pyridine-3,5-dicarboxylate in the same manner as that of Example 1-2).

Yield: 58 mg (0.10 mmol) (50.0%) MS (ESI, m/z) 554 (M–H) 1H-NMR (CDCl3): 2.32(2H, q), 2.42(3H, s), 3.62 (1H, t), 3.90(1H, t), 4.04(1H, t), 5.04(1H, s), 6.21(1H, s), 7.10–7.32(14H, m)

EXAMPLE 58

Synthesis of 3-(3,3-diphenylpropyl)4-(3-chlorophenyl)-2-(2,3-dihydropropoxymethyl)-6-methyl-1,4-dihydropyridine-3,5-dicarboxylate 1) Synthesis of 5-(2-cyanoethyl)3-(3,3-diphenylpropyl)4-(3-chlorophenyl)-2-(2,3-dihydropropoxymethyl)-6-methyl-1,4-dihydro-pyridine-3,5-dicarboxylate:

246 mg (0.36 mmol) of 5-(2-cyanoethyl)3-(3,3-diphenylpropyl)4-(3-chlorophenyl)-2-(2,2-dimethyl-[1,3]dioxolane-4-ylmethoxymethyl)-6-methyl-1,4-dihydropyridine-3,5-dicarboxylate was dissolved in 2 ml of 1,4-dioxane. 5 ml of 4 N hydrochloric acid/dioxane was added to the obtained solution. After stirring at room temperature for 4 hours, dioxane was evaporated under reduced pressure. Saturated aqueous sodium hydrogencarbonate solution was added to the residue. After the extraction with ethyl acetate, the organic layer was dried over anhydrous sodium hydrogensulfate and then concentrated under reduced pressure. The residue was purified by the silica gel chromatography (chloroform/methanol=50/1) to obtain the title compound.

Yield: 50 mg (0.08 mmol) (21.5%) MS (ESI, m/z) 643 (M–H)– 1H-NMR (CDCl3): 2.29–2.39 (2H, m), 2.38 (3H, s), 2.64 (2H, t), 3.54–3.82 (5H, m), 3.86–4.03 (3H, m), 4.21–4.36 (2H, m), 4.68–4.84 (2H, m), 4.99 (1H, s), 7.06–7.32 (14H, m), 7.61 (1H, s)

2) Synthesis of 3-(3,3-diphenylpropyl)4-(3-chlorophenyl)-2-(2,3-dihydropropoxymethyl)-6-methyl-1,4-dihydropyridine-3,5-dicarboxylate:

The title compound was obtained from 50 mg (0.08 mmol) of 5-(2-cyanoethyl)3-(3,3-diphenylpropyl)4-(3-chlorophenyl)-2-(2,3-dihydroxy-propoxymethyl)-6-methyl-1,4-dihydropyridine-3,5-dicarboxylate in the same manner as that of Example 33-4).

Yield: 28 mg (0.05 mmol) (60.3%) MS (ESI, m/z) 590 (M–H)– 1H-NMR (DMSO-d6): 2.22–2.37 (5H, m), 3.34–3.72 (4H, m), 3.78–3.89 (3H, m), 4.58–4.74 (3H, m), 4.97 (1H, s), 5.10 (1H, t), 7.08–7.36 (14H, m), 8.61 (1H, s), 11.94 (1H, brd)

EXAMPLE 59

Synthesis of 3-benzyl 5-(3,3-diphenylpropyl)4-(3-chlorophenyl)-2-methyl-6-trifluoromethyl-1,4-dihydropyridine-3,5-dicarboxylate 1) Synthesis of 3-benzyl 5-(2-cyanoethyl)4-(3-chlorophenyl)-2-methyl-6-trifluoromethyl-1,4-dihydropyridine-3,5-dicarboxylate:

1.2 g (5.7 mmol) of 2-cyanoethyl 4,4,4-trifluoro-3-oxobutanoate, 878 mg (4.6 mmol) of 3-chlorobenzaldehyde and 646 mg (4.6 mmol) of 2-cyanoethyl 3-aminocrotonate were stirred in 50 ml of 1,2-dichloroethane at 75° C. overnight. 2.0 g of silica gel containing phosphoryl chloride and pyridine adsorbed thereon was added to the obtained mixture, and they were stirred overnight. Silica gel was filtered out and then the solvent was evaporated under reduced pressure. The residue was purified by the basic silica gel chromatography (ethyl acetate/hexane=1/2 to 1/1) to obtain the title compound.

Yield: 954 mg (1.91 mmol) (41.5%) 1H-NMR (CDCl3): 2.44(3H, s), 2.66(2H, t), 4.32(2H, m), 5.04(1H, s), 6.29(1H, bs), 7.17–7.24(4H, m)

2) Synthesis of 3-benzyl 5-(2-cyanoethyl)4-(3-chlorophenyl)-2-methyl-6-trifluoromethyl-1,4-dihydropyridine-3,5-dicarboxylate:

The title compound was obtained from 3-benzyl 5-(2-cyanoethyl)4-(3-chlorophenyl)-2-methyl-6-trifluoromethyl-1,4-dihydropyridine-3,5-dicarboxylate in the same manner as that of Example 23-4).

Yield: 778 mg (1.91 mmol) 100% 1H-NMR (CDCl3): 2.43(3H, s), 2.63(2H, t), 4.30(2H, m), 5.05(1H, s), 5.06(1H, d), 5.15(1H, d), 6.23(1H, bs), 7.10–7.39(9H, m)

3) Synthesis of 5-(2-cyanoethyl)4-(3-chlorophenyl)-2-methyl-6-trifluoromethyl-1,4-dihydropyidine-3,5-dicarboxylate:

175 mg (1.02 mmol) of N,N,N,N-tetramethylazodicarboxamide was added to a solution of 248 mg (0.61 mmol) of 3-benzyl 5-(2-cyanoethyl)4-(3-chlorophenyl)-2-methyl-6-trifluoromethyl-1,4-dihydropyridine-3,5-dicarboxylate, 128 mg (0.61 mmol) of 3,3-diphenylpropanol and 176 mg (0.67 mmol) of triphenylphosphine in 5 ml of THF, and they were stirred overnight. 15 ml of benzene was added to the obtained solution, and they were further stirred overnight. The obtained precipitate was filtered out and roughly purified by the thin layer silica gel chromatography (ethyl acetate/hexane=175/200) and then by the silica gel chromatography (ethyl acetate/hexane=15/85) to obtain the title compound.

Yield: 54.2 mg (0.089 mmol) 14.5% 1H-NMR (CDCl3): 2.31 (2H, q), 2.42 (3H, s), 2.61 (2H, m), 3.89 (1H, t), 4.02 (2H, m), 4.26 (2H, m), 5.02 (1H, s), 6.16 (1H, bs), 7.12–7.28 (14H, m)

4) Synthesis of 3-benzyl 5-(3,3-diphenylpropyl)4-(3-chlorophenyl)-2-methyl-6-trifluoromethyl-1,4-dihydropyridine-3,5-dicarboxylate:

The title compound was obtained from 54.2 mg (0.089 mmol) of 5-( 2-cyanoethyl)4-(3-chlorophenyl)-2-methyl-6-trifluoromethyl-1,4-dihydropyridine-3,5-dicarboxylate in the same manner as that of Example 50-2).

Yield: 40.4 mg (0.072 mmol) (80.9%) MS (ESI, m/z) 554(M–H) 1H-NMR (CDCl3): 2.34 (2H, q), 2.42(3H, s), 3.88 (1H, t), 4.01 (2H, m), 5.09 (1H, s), 6.26 (1H, bs), 7.06–7.35 (14H, m)

EXAMPLE 60

Synthesis of 3-(3,3-diphenylpropyl)4-(3-chlorophenyl)-2-dimethoxymethyl-6-methyl-1,4-dihydropyridine-3,5-dicarboxylate 1) Synthesis of 5-2-(cyanoethyl)3-(3,3-diphenylpropyl)4-(3-chlorophenyl)-2-dimethoxymethyl-6-methyl-1,4-dihydropyridine-3,5-dicarboxylate:

0.10 g (0.24 mmol) of 5-(2-cyanoethyl)4-(3-chlorophenyl)-2-dimethoxymethyl-6-methyl-1,4-dihydropyridine-3, 5-dicarboxylate, 66 mg (0.31 mmol) of 3,3-diphenylpropanol and 94 mg (0.36 mmol) of triphenylphosphine were dissolved in 1 ml of THF, and the obtained solution was diluted with 15 ml of benzene. 61 mg (0.35 mmol) of 1,1'-azobis(N,N-dimethylformamide) was slowly added to the obtained solution, and they were stirred at room temperature for 48 hours. Ethyl acetate was added to the reaction mixture. The obtained mixture was successively washed with 1 N hydrochloric acid, water and saturated aqueous sodium chloride solution. The organic layer was dried over anhydrous magnesium sulfate and then concentrated under reduced pressure. The residue was purified by the silica gel column chromatography (hexane/ethyl acetate=7/3 to 1/1) to obtain the title compound.

Yield: 0.13 g (0.22 mmol (90.8%) MS (ESI, m/z) 613 (M–H)– 1H-NMR (CDCl3): 2.35 (2H, m), 2.37 (3H, s), 2.64 (2H, t), 3.44 (3H, s), 3.46 (3H, s), 3.92 (1H, t), 4.00 (2H, t), 4.27 (2H, m), 5.04 (1H, s), 6.03 (1H, s), 6.83 (1H, s), 7.26–7.37 (14H, m)

2) Synthesis of 3-(3,3-diphenylpropyl)4-(3-chlorophenyl)-2-dimethoxymethyl-6-methyl-1,4-dihydropyridine-3,5-dicarboxylate:

The title compound was obtained from 0.13 g (0.22 mmol) of 5-(2-cyano ethyl)3-(3,3-diphenylpropyl)4-(3-chlorophenyl)-2-dimethoxy-methyl-6-methyl-1,4-dihydropyridine-3,5-dicarboxylate in the same manner as that of Example 1-2).

Yield: 0.10 g (0.22 mmol) (83.8%) MS (ESI, m/z) 560 (M–H)– 1H-NMR (CDCl3): 2.36 (2H, m), 2.37 (3H, s), 3.44 (3H, s), 3.46 (3H, s), 3.85 (1H, t), 3.99 (2H, t), 5.06 (1H, s), 6.05 (1H, s), 6.86 (1H, s), 7.05–7.35 (14H, m)

EXAMPLE 61

Synthesis of 3,3-diphenylpropyl 5-(1-benzylpiperidine-4-yl-carbamoyl)-4-(3-chlorophenyl)-2,6-dimethyl-1,4-dihydropyridine-3-carboxylate The title compound was obtained from 304 mg (0.61 mmol) of mono(3,3-diphenylpropane-1-yl)4-(3-chlorophenyl)-2,6-dimethyl-1,4-dihydropyridine-3,5-dicarboxylate and 0.18 ml (0.88 mmol) of 4-amino-1-benzylpiperidine in the same manner as that of Example 21.

Yield: 403 mg (0.60 mmol) (98.4%) MS(ESI, m/z) 672 (M–H)– 1H-NMR (CDCl3): 1.26–1.33 (2H, m), 1.70–1.90 (2H, m), 2.03–2.15 (2H, m) 2.18 (3H, s), 2.28–2.38 (2H, m), 2.30 (3H, s), 2.54–2.69 (2H, m), 3.43 (2H, s), 3.72–4.00 (4H, m), 4.74 (1H, s), 5.16 (1H, d), 5.43 (1H, s), 7.09–7.30 (19H, m)

EXAMPLE 62

Synthesis of 5-(3,3-diphenyl-1-propyl)4-(3-chlorophenyl)-2-methyl-6-hexyloxymethyl-1,4-dihydropyridine-3,5-dicarboxylate 1) Synthesis of 3,3-diphenylpropyl 4-hexyloxyacetoacetate:

The title compound was obtained from 370 mg (3.63 mmol) of hexanol in the same manner as that of Example 30.

Yield: 952 mg (2.40 mmol) (99%) MS (ESI, m/z) 395 (M–H)– 1H-NMR (CDCl3): 0.90(3H, t), 1.27–1.32 (8H, m), 2.40 (2H, dt), 3.45–3.51 (4H, m), 4.01–4.14 (5H, m), 7.19–7.29 (10H, m)

2) Synthesis of 3,3-diphenylpropyl 3-amino-4-hexyloxycrotonate:

The title compound was obtained from 952 mg (2.40 mmol) of 3,3-diphenylpropyl4-hexyloxyacetoacetate in the same manner as that of Example 17-2).

Yield: 0.88 mg (2.24 mmol) (91%) MS (ESI, m/z) 396 (M+H)+ 1H-NMR (CDCl3): 0.89((3H, t), 1.20–1.30 (8H, m), 2.38 (2H, dt), 3.43 (2H, t), 3.93–4.13 (5H, m), 4.53 (1H, s), 7.16–7.27 (10H, m)

3) Synthesis of 3-benzyl 5-(3,3-diphenyl-1-propyl)4-(3-chlorophenyl)-6-methyl-2-hexyloxymethyl-1,4-dihydropyridine-3,5-dicarboxylate:

The title compound was obtained from 372 mg (2.40 mmol) of 2-cyanoethyl acetoacetate, 371 mg (2.60 mmol) of 3-chlorobenzaldehyde and 0.88 mg (2.24 mmol) of 3,3-diphenyl-1-propyl 3-amino-4-hexyloxycrotonate in the same manner as that of Example 14-2).

Yield: 402 mg (0.59 mmol) (25%) MS (ESI, m/z) 655 (M+H)+ 1H-NMR (CDCl3): 0.92(3H, t), 1.29–1.37 (6H, m), 1.66 (2H, m), 2.30–2.39 (5H, m), 2.65 (2H, t), 3.55 (2H, dt), 3.89–3.99 (3H, m), 4.29(2H, dt), 4.67 (1H, d), 4.69(1H, d), 5.00 (1H, s), 5.31 (1H, s), 7.08–7.30 (14H, m)

4) Synthesis of 5-(3,3-diphenyl-1-propyl)4-(3-chlorophenyl)-2-methyl-6-hexyloxymethyl-1,4-dihydropyridine-3,5-dicarboxylate:

The title compound was obtained from 115 mg (0.17 mmol) of 3-(2-cyanoethyl)5-(3,3-diphenyl-1-propyl)4-(3-chlorophenyl)-2-methyl-6-hexyloxymethyl-1,4-dihydropyridine-3,5-dicarboxylate in the same manner as that of Example 33-4).

Yield: 43.3 mg (0.072 mmol) (42%) MS (ESI, m/z) 602 (M+H)+ 1H-NMR (CDCl3): 0.85(3H, t), 1.14–1.26 (6H, m), 1.52 (2H, t), 2.24–2.49 (5H, m), 3.44 (2H, t), 3.76(2H, t), 3.98(1H, m), 4.61(2H, s), 5.23 (1H, s), 7.03–7.30 (14H, m), 7.65 (1H, s)

EXAMPLE 63

Synthesis of 5-(3,3-diphenyl-1-propyl)4-(3-carboxyphenyl)-2-methyl-6-hexyloxymethyl-1,4-dihydropyridine-3,5-dicarboxylate 1) Synthesis of 3-benzyl 5-(3,3-diphenyl-1-propyl)4-(3-carboxyphenyl)-6-methyl-2-hexyloxymethyl-1,4-dihydropyridine-3,5-dicarboxylate:

The title compound was obtained from 310 mg (2.0 mmol) of cyanoethyl acetoacetate, 360 mg (2.4 mmol) of 3-carboxybenzaldehyde and 794 mg (2.0 mmol) of 3,3-diphenyl-1-propyl 3-amino-4-hexyloxycrotonate in the same manner as that of Example 14-2).

Yield: 832 mg (1.3 mmol) (63%) MS (ESI, m/z) 665 (M+H)+ 1H-NMR (CDCl3): 0.89(3H, t), 1.22–1.28 (8H, m),2.30–2.35 (2H, m), 2.39 (3H, s), 2.64 (2H, t), 3.55(2H, dt), 3.88–3.96 (3H, m), 4.26 (2H, t), 4.67(1H, d), 4.70 (1H, d), 5.08 (1H, s), 7.07–7.26 (10H, m), 7.35 (1H, t), 7.56(1H, d), 7.92(1H, d), 8.04(1H, s)

2) Synthesis of 5-(3,3-diphenyl-1-propyl)4-(3-carboxyphenyl)-2-methyl-6-hexyloxymethyl-1,4-dihydropyridine-3,5-dicarboxylate:

The title compound was obtained from 417 mg (0.60 mmol) of 3-(2-cyanoethyl)5-(3,3-diphenyl-1-propyl)4-(3-carboxyphenyl)-2-methyl-6-hexyloxymethyl-1,4-dihydropyridine-3,5-dicarboxylate in the same manner as that of Example 33-4).

Yield: 311 mg (0.47 mmol) (78%) MS (ESI, m/z) 611 (M+H)+ 1H-NMR (CDCl3): 0.84(3H, t), 1.18–1.26 (6H, m), 1.52 (2H, t), 2.28–2.31 (5H, m), 3.79–4.04 (5H, m), 4.50 (1H, d), 4.66 (1H, d), 5.03(1H, s), 7.11–7.29 (11H, m), 7.68–7.83(3H, m), 8.42 (1H, s)

EXAMPLE 64

Synthesis of 3-(3,3-diphenylpropyl)2-(2-carboxyethoxymethyl)-4-(3-chlorophenyl)-6-methyl-1,4-dihydropyridine-3,5-dicarboxylate 1) Synthesis of 3,3-diphenylpropyl 4-(3-hydroxypropoxy)-3-oxobutanoate:

4.33 g (9.41 mmol) of 3,3-diphenylpropyl 4-(3-benzyloxypropoxy)-3-oxobutanoate was hydrogenated in the presence of a catalytic amount of 5% palladium/carbon in 50 ml of ethanol under 5 atm. for 14 days. After an ordinary after treatment followed by the purification by the silica gel chromatography (hexane/ethyl acetate=1/1), the title compound was obtained.

Yield: 1.36 g (3.66 mmol) (38.9%) MS (ESI, m/z) 369 (M–H)– 1H-NMR (CDCl3): 1.79–1.92 (2H, m), 2.29–2.50 (2H, m), 3.46 (2H, s), 3.58–3.82 (4H, m), 4.01–4.20 (5H, m), 7.15–7.33 (10H, m)

2) Synthesis of 3,3-diphenylpropyl 4-(2-carboxyethoxy)-3-oxobutanoate:

625 mg (6.25 mmol) of chromic acid, 0.65 ml of concentrated sulfuric acid and 2.9 ml of water were added to 1.36 g (3.66 mmol) of 3,3-diphenylpropyl 4-(3-hydroxypropoxy)-3-oxobutanoate in 17 ml of acetone, and they were stirred at room temperature for 1.5 hours. After the addition of water and extraction with ethyl acetate, the organic layer was washed with water and then saturated aqueous sodium chloride solution, dried over anhydrous sodium sulfate and concentrated under reduced pressure. The residue was purified by the silica gel chromatography (hexane/ethyl acetate=1/1) to obtain the title compound.

Yield: 918 mg (2.39 mmol) (65.2%) MS (ESI, m/z) 383 (M–H)– 1H-NMR (CDCl3):2.36–2.46 (2H, m), 2.65 (2H, t), 3.48 (2H, s), 3.78 (2H, t), 4.01–4.14 (3H, m), 4.15 (2H, s), 7.16–7.33 (10H, m)

3) Synthesis of 5-(2-cyanoethyl)3-(3,3-diphenylpropyl)2-(2-carboxyethoxymethyl)-4-(3-chlorophenyl)-6-methyl-1, 4-dihydropyridine-3,5-dicarboxylate:

913 mg (2.37 mmol) of 3,3-diphenylpropyl 4-(2-carboxyethoxy)-3-oxobutanoate, 0.27 ml (2.44 mmol) of 3-chlorobenzaldehyde and 0.025 ml (0.25 mmol) of piperidine were refluxed in 30 ml of benzene for 3 hours while water was removed. Ethyl acetate was added to the reaction mixture. The organic layer was washed with 1 N hydrochloric acid, dried over anhydrous sodium sulfate and concentrated under reduced pressure. 20 ml of 2-propanol and 365 mg (2.37 mmol) of 2-cyanoethyl 3-aminocrotonate were added to the residue, and they were stirred under heating at 80° C. overnight. 2-propanol was evaporated under reduced pressure, and the residue was purified by the silica gel chromatography (hexane/ethyl acetate=1/1, 0.2% acetic acid) to obtain the title compound.

Yield: 195 mg (0.30 mmol) (12.7%) MS (ESI, m/z) 641 (M–H)– 1H-NMR (CDCl3): 2.28–2.48 (7H, m), 2.62–2.78 (4H, m), 3.72–3.82 (1H, m), 3.87–3.92 (2H, m), 4.20–4.34 (2H, m), 4.76 (2H, d), 4.99 (1H, s), 7.06–7.32 (14H, m), 7.70 (1H, s)

4) Synthesis of 3-(3,3-diphenylpropyl)2-(2-carboxyethoxymethyl)-4-(3-chlorophenyl)-6-methyl-1,4-dihydropyridine-3,5-dicarboxylate:

The title compound was obtained from 195 mg (0.30 mmol) of 5-(2-cyanoethyl)3-(3,3-diphenylpropyl)2-(2-carboxyethoxymethyl)-4-(3-chlorophenyl)-6-methyl-1,4-dihydropyridine-3,5-dicarboxylate in the same manner as that of Example 50-2).

Yield: 57 mg (0.10 mmol) (32.3%) MS (ESI, m/z) 588 (M–H)– 1H-NMR (DMSO-d6): 2.25–2.36 (5H, m), 2.57 (2H, t), 3.64 (2H, t), 3.80–3.90 (3H, m), 4.65 (2H, d), 4.97 (1H, s), 7.09–7.35 (14H, m), 8.61 (1H, s)

The structural formulae of the compounds obtained in Examples 1 to 64 are shown in the following tables, wherein the numerals correspond to the numbers of Examples.

TABLE 1
| Example | Structure |
|---|---|
| 1 | 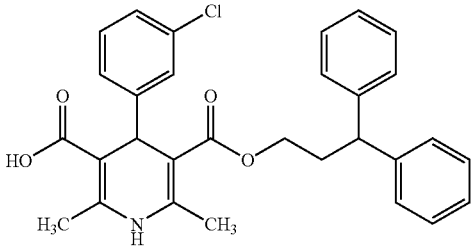 |
| 2 | 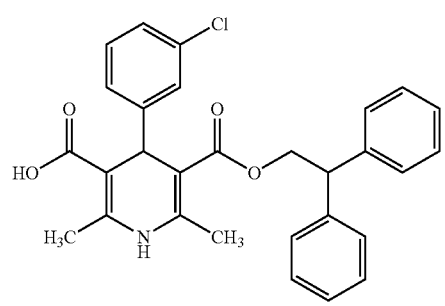 |
| 3 | 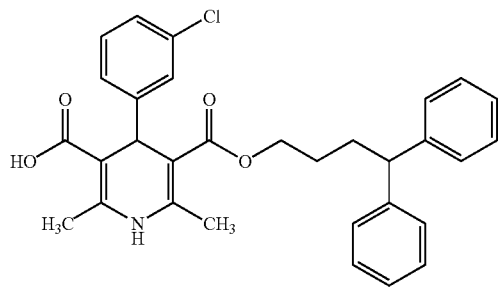 |
| 4 | 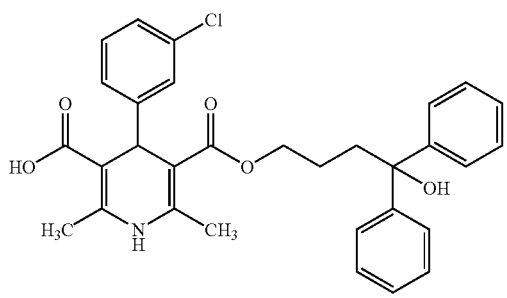 |
TABLE 1-continued
| Example | Structure |
|---|---|
| 5 | 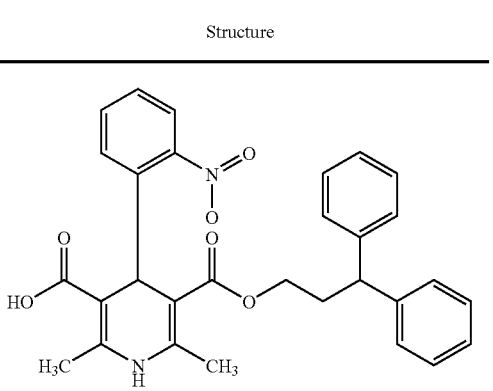 |
| 6 | 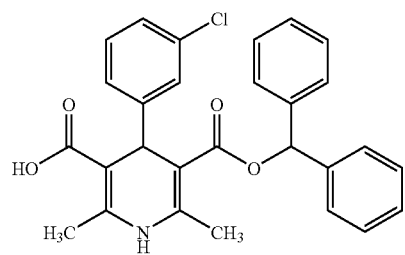 |
| 7 | 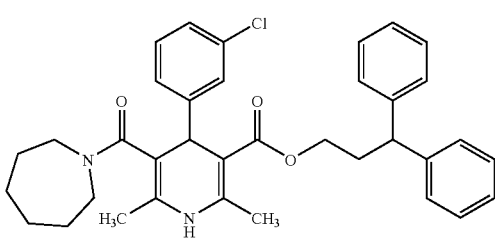 |
| 8 | 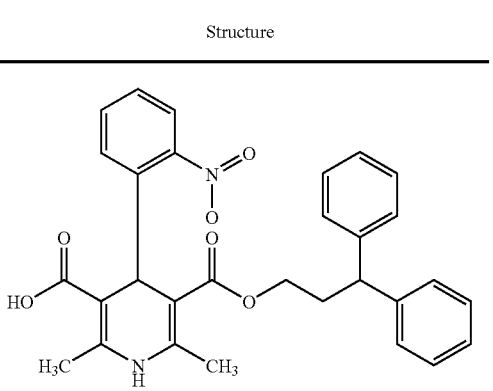 |

TABLE 2
| | |
|---|---|
| 9 | 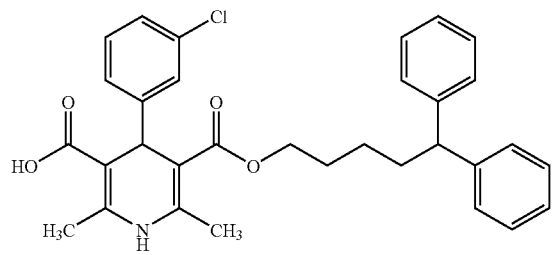 |
| 10 | 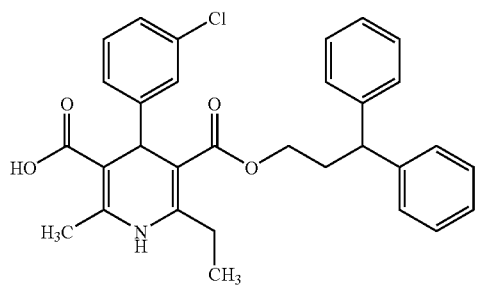 |
| 11 | 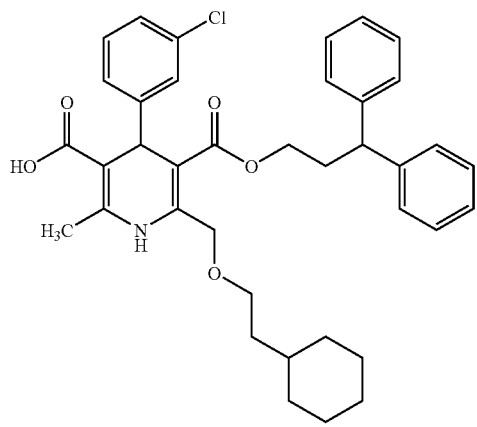 |
| 12 | 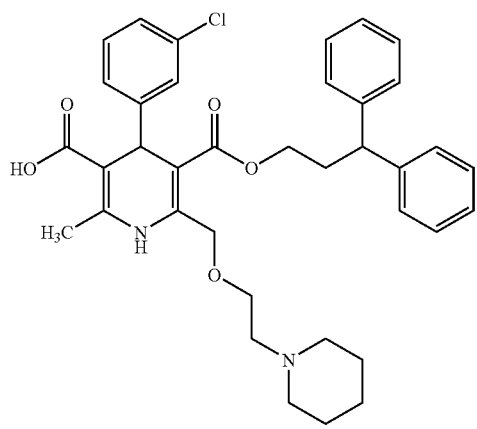 |

TABLE 2-continued
13
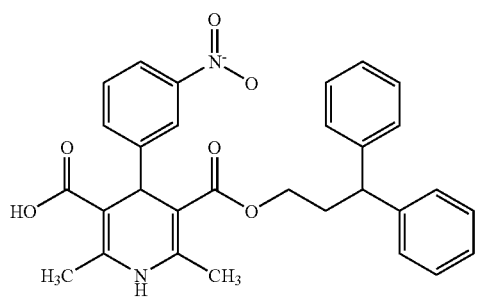
14
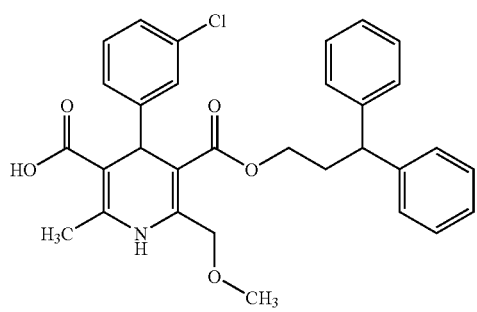
15
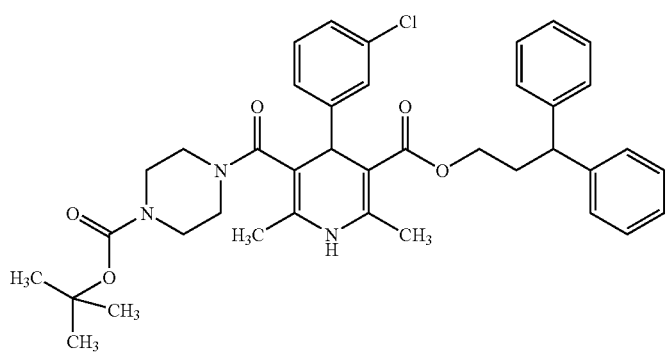
16
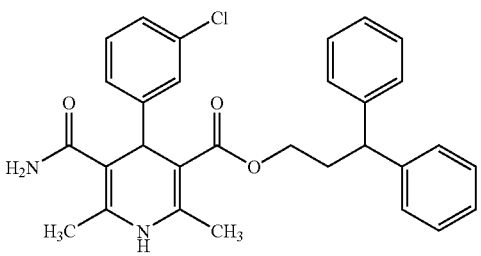

TABLE 3
17 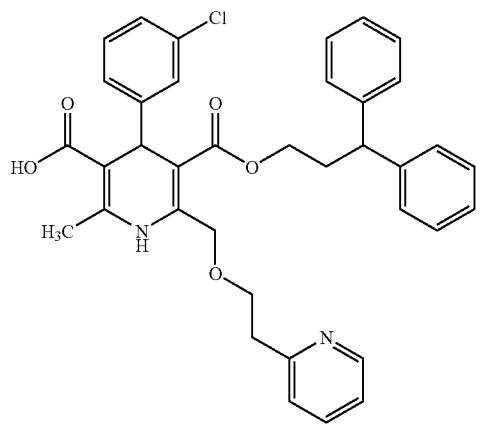
18 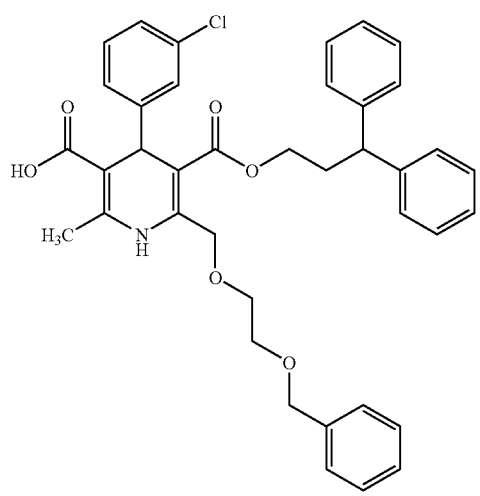
19 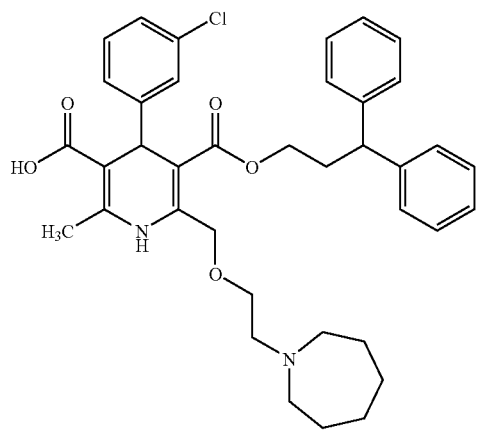

TABLE 3-continued
20 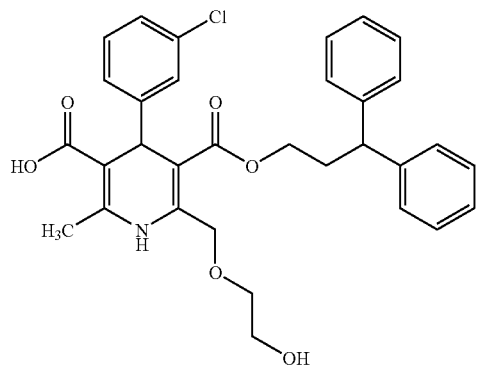
21 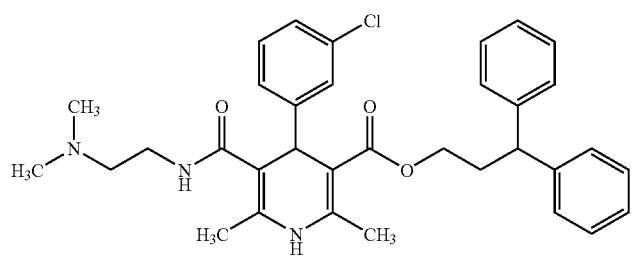
22 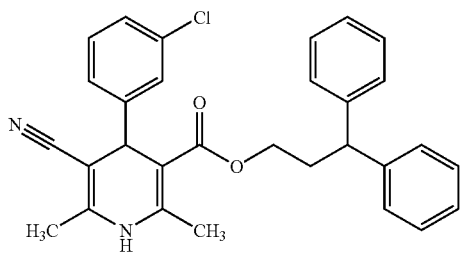
23 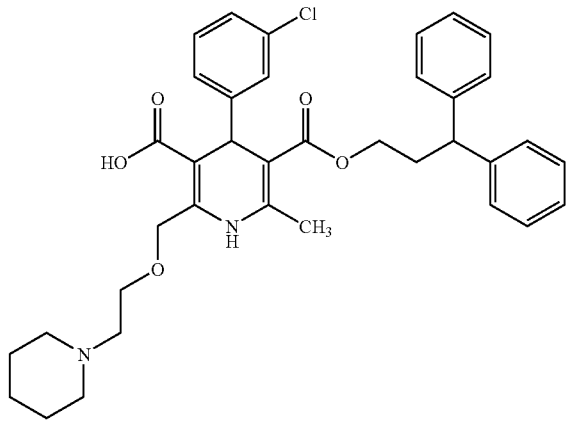
24 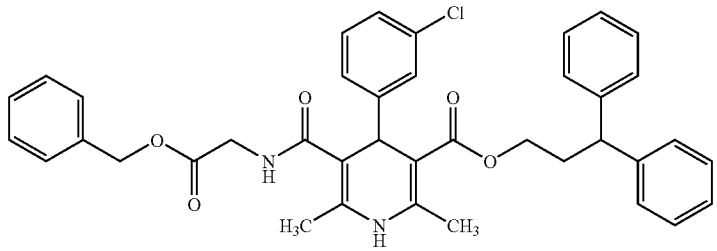

TABLE 4
| | |
|---|---|
| 25 | 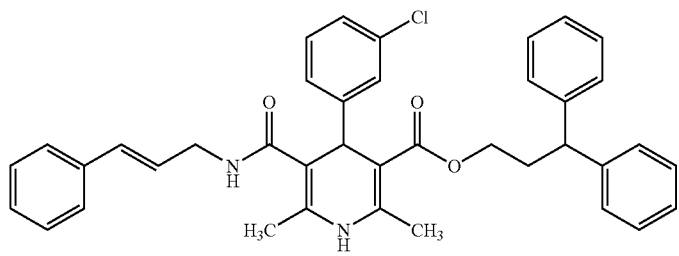 |
| 26 | 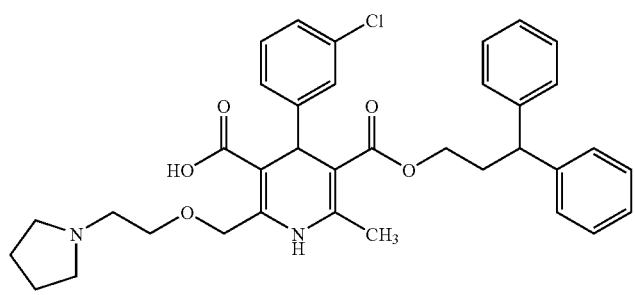 |
| 27 | 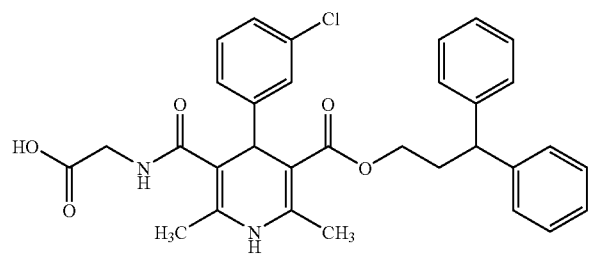 |
| 28 | 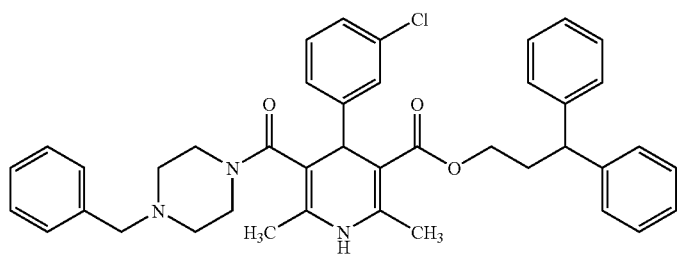 |
| 29 | 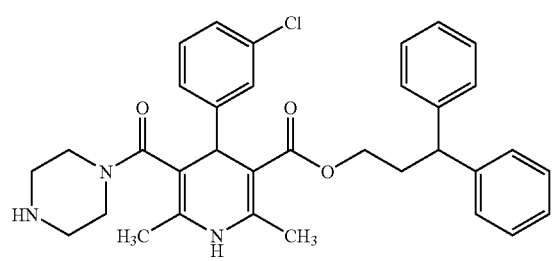 |

TABLE 4-continued
30 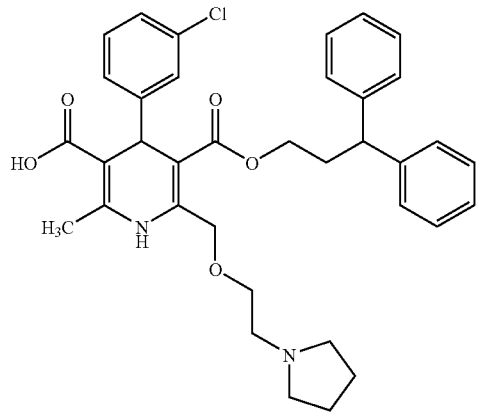
31 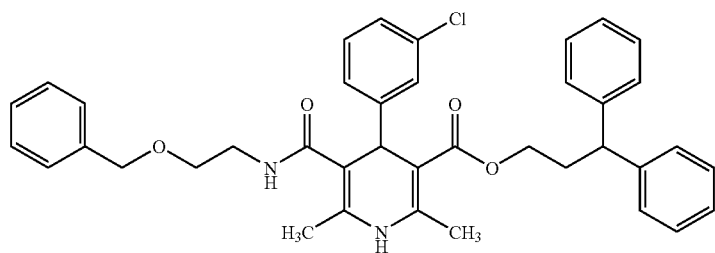
32 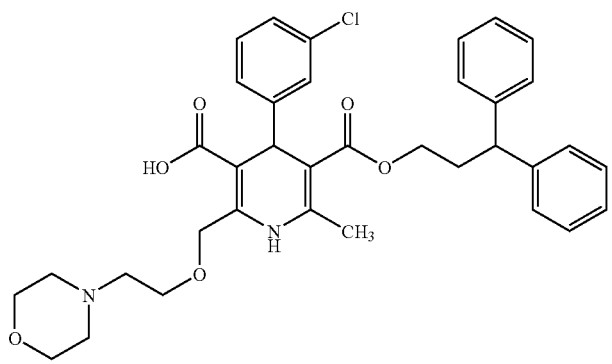
TABLE 5
33 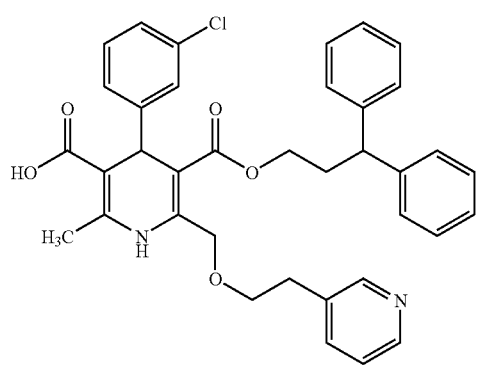

TABLE 5-continued
| 34 | 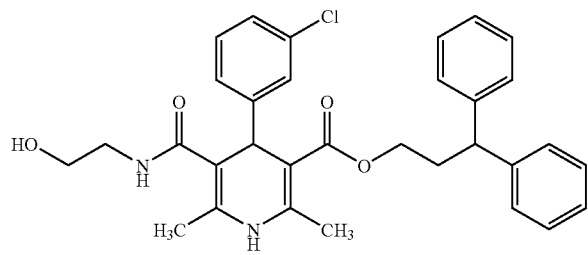 |
| --- | --- |
| 35 | 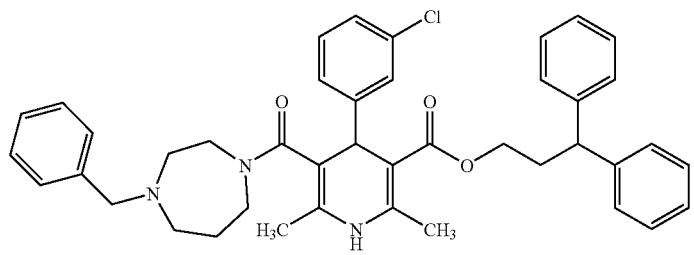 |
| 36 | 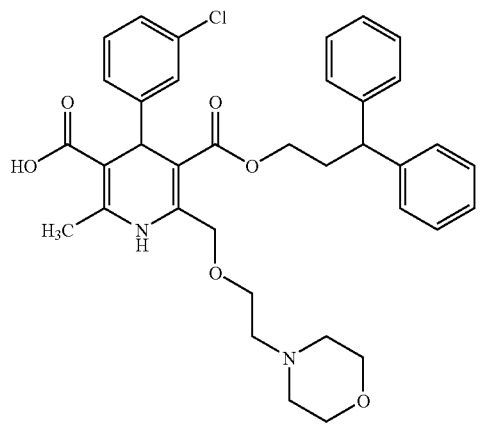 |
| 37 | 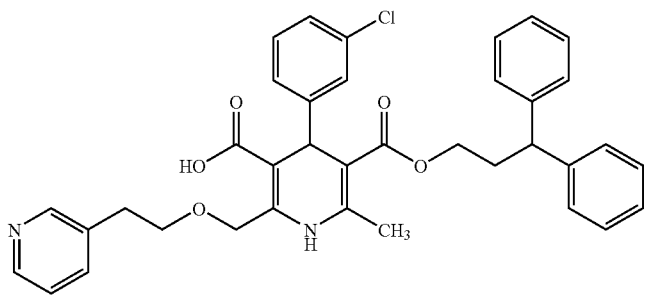 |
| 38 | 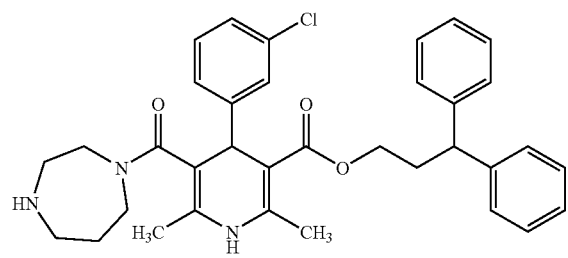 |

TABLE 5-continued
39
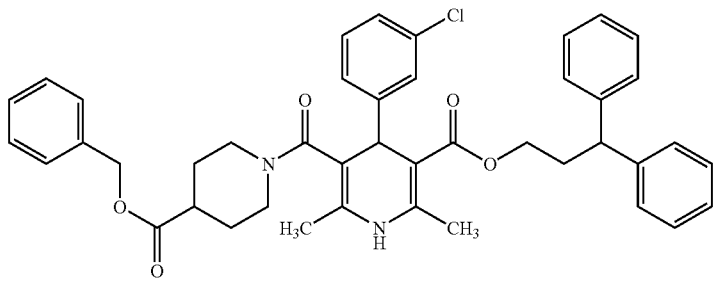
40
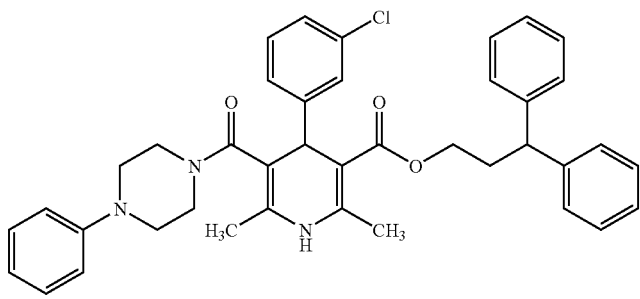
TABLE 6
41
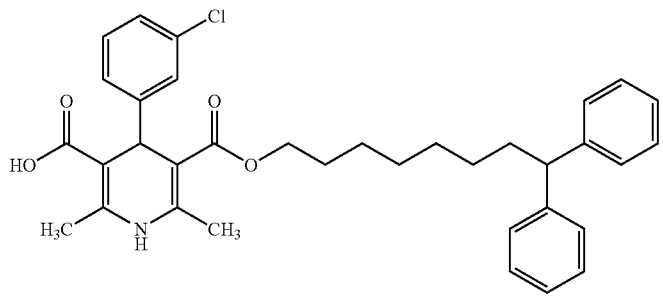
42
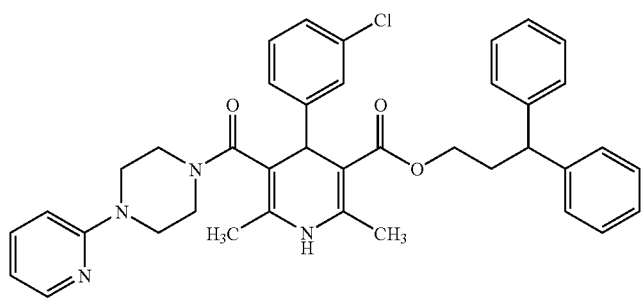

TABLE 6-continued
43 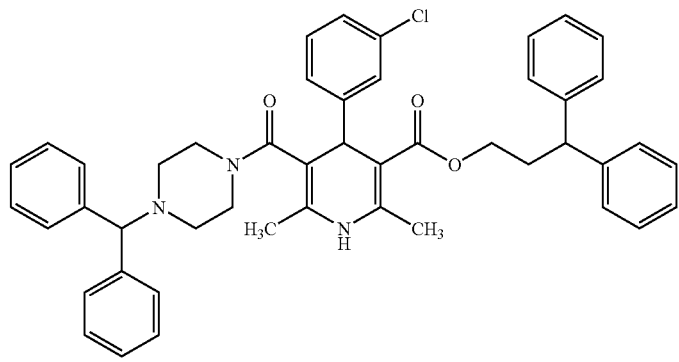
44 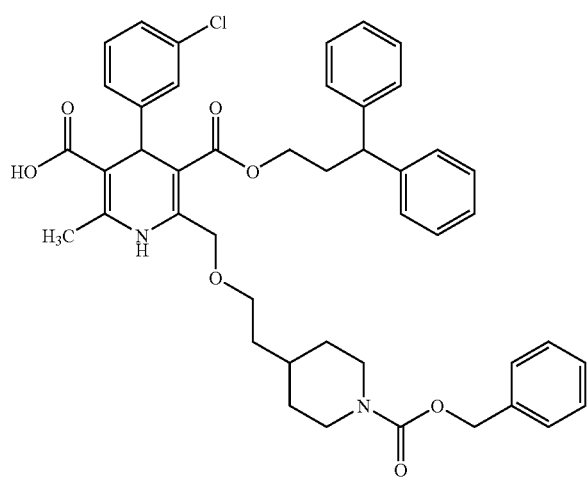
45 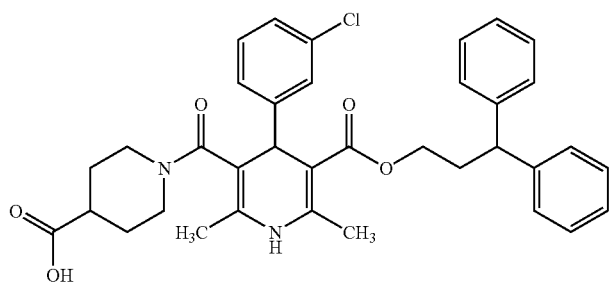
46 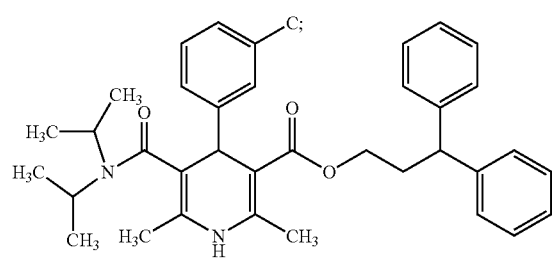

TABLE 6-continued
47 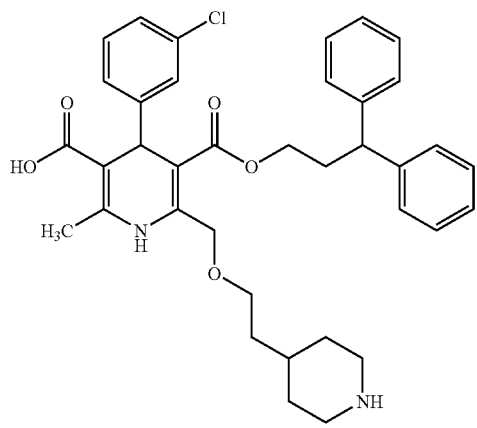
48 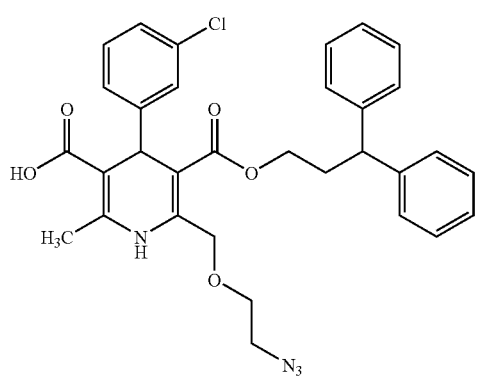
TABLE 7
49 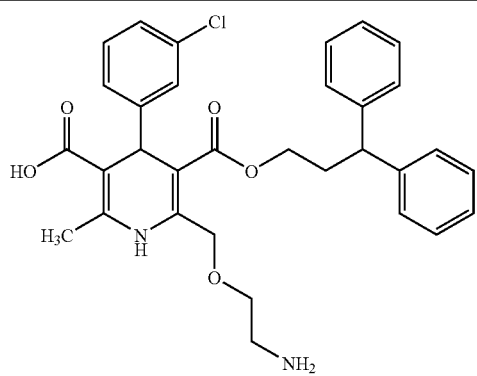
50 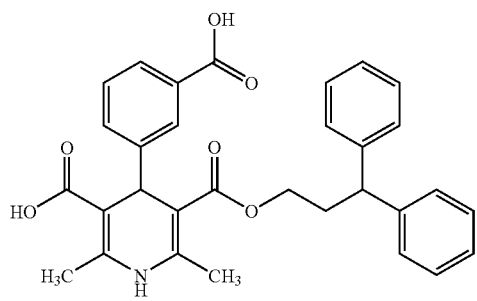

TABLE 7-continued
| 51 | 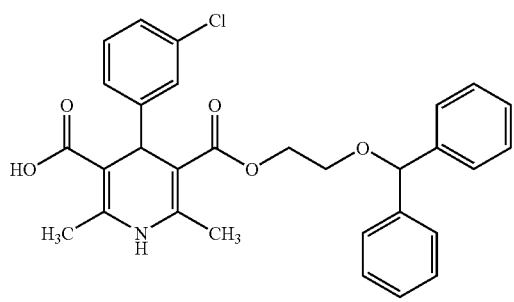 |
| --- | --- |
| 52 | 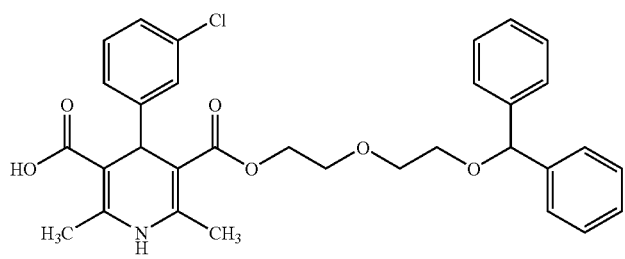 |
| 53 | 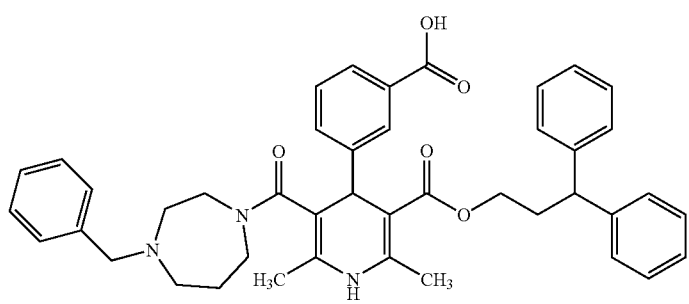 |
| 54 | 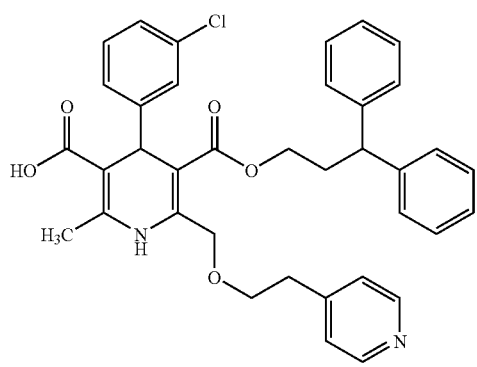 |

TABLE 7-continued
55
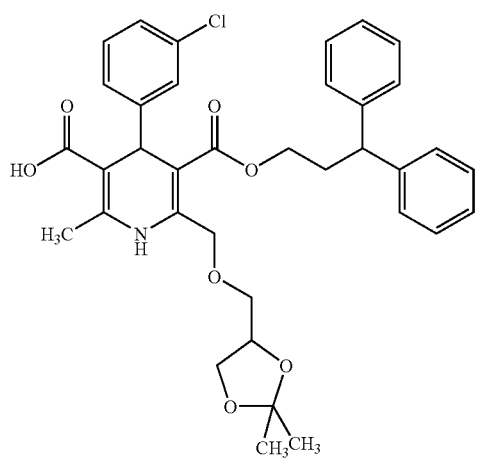
56
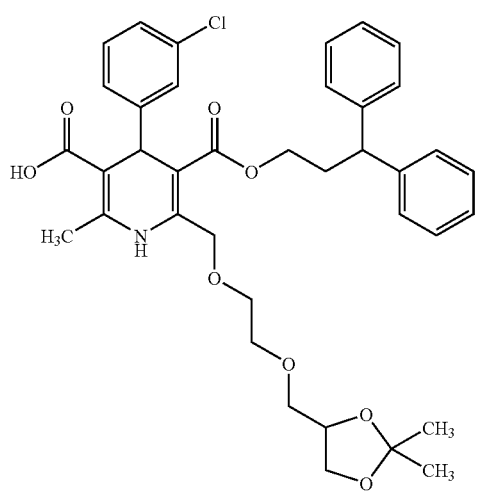
TABLE 8
57
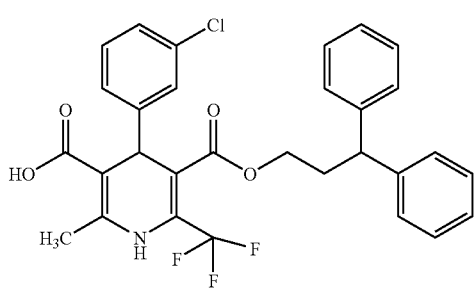

TABLE 8-continued
58
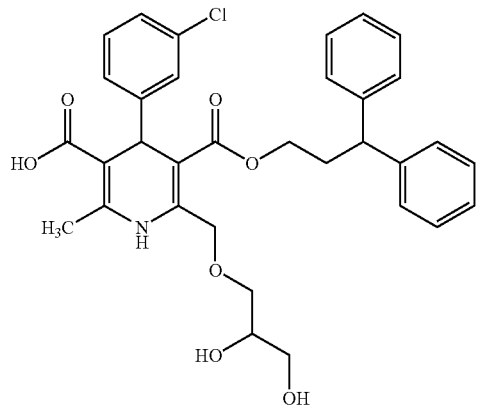
59
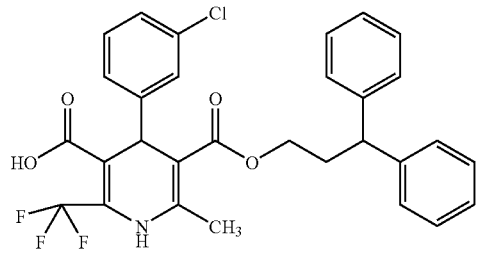
60
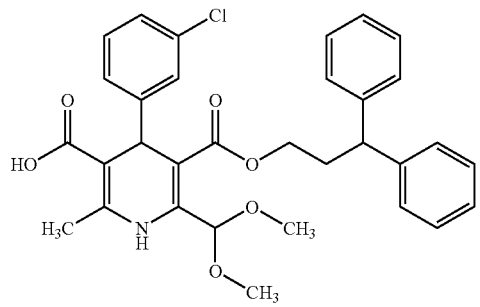
61
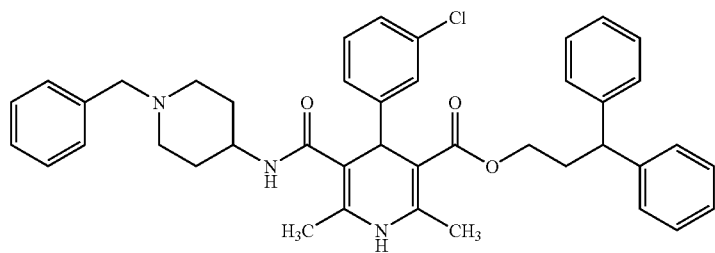

TABLE 8-continued

62 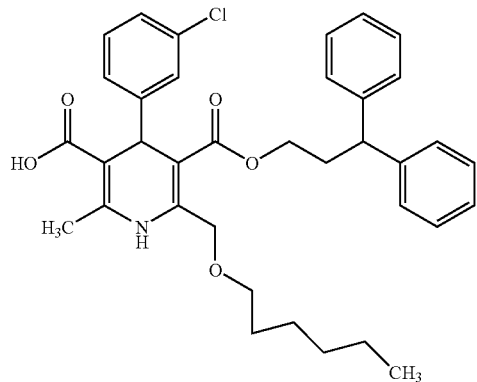

63 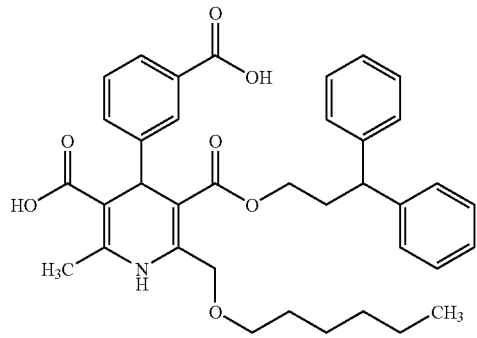

64 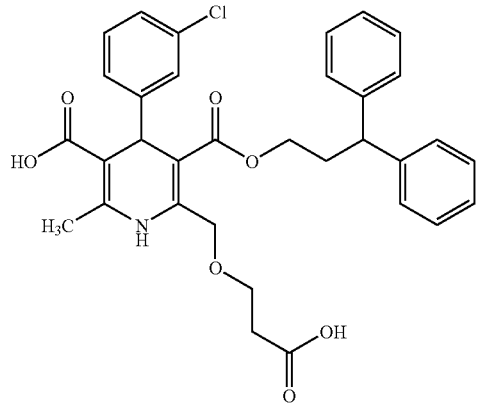

Test Example

Antagonistic Activity on L-type Calcium Channel

The activity of the dihydropyridine derivatives of the present invention to inhibit L-type calcium channel was determined by the following method in which the relaxation reaction on the KCl contraction of samples of thoracic aorta extracted from rats was employed.

1) Method of preparation of samples of thoracic aorta extracted from rats:

The slips of thoracic aorta extracted from a Sprague-Dawry rat was used. The blood vessels were cut to obtain ring-shaped samples having a width of about 3 mm. The endothelial cells of the blood vessel were mechanically removed. The samples were suspended in a strain gage in Tyrode's solution (158.3 mM of NaCl, 4.0 mM of KCl, 1.05 mM of $MgCl_2$, 0.42 mM of $NaH_2PO_4$, 10 mM of $NaHCO_3$, 2 mM of $CaCl_2$ and 5 mM of glucose) in which a gaseous mixture of $O_2$ (95%) and $CO_2$ (5%) was introduced. A static tension of 2 g was applied hereto. The tension of the blood vessel was amplified with transducer and a tension amplifier (EF-601G; Nihon Koden Corporation) and recorded with a multi-pen recorder (Rikadenki Kogyo Co., Ltd.). The experiments were conducted at 37° C.

2) Determination of Relaxation After KCl Contraction:

After the tension had been stabilized, the nutrient solution in the sample tank was replaced with High $K^+$ Tyrode's solution (112.3 mM of NaCl, 50 mM of KCl, 1.05 mM of $MgCl_2$, 0.42 mM of $NaH_2PO_4$, 10 mM of $NaHCO_3$, 2 mM of $CaCl_2$ and 5 mM of glucose) to conduct the contraction reaction. 30 minutes after, the solution in the sample tank was replaced with the normal Tyrode's solution. The solution in the sample tank was again replaced with the High $K^+$ Tyrode's solution and the contraction reaction was observed. After attaining the maximum contraction reaction, the test compound was cumulatively added at intervals of 90 minutes to attain concentrations of $10^{-7}$, $10^{-6}$ and $10^{-5}$M. The rate of the test compound to control the maximum contraction reaction was employed as the index of the inhibition activity on L-type calcium channel.

Test Example

Antagonistic Activity on N-type Calcium Channel
(Fluorescence Dye Method)

Human neuroblastoma cells IMR-32 were obtained from ATCC (American Type Culture Collection). The medium used was a Phenol Red-free Eagle minimum essential medium (GIBCO) containing earle's salts supplement, 2 mM of L-glutamine (GIBCO), 1 mM of sodium pyruvate (pH 6.5) (GIBCO), antibiotic/antimicotic mixture (GIBCO) and 10% fetal calf serum (Cell Culture Technologies). 3 ml of $1\times10^5$/ml IMR-32 cells were spread on a glass dish (Iwaki Glass Co., Ltd.) having a diameter of 35 mm which was treated with poly-D-lysin (SIGMA) and collagen (COLLAGEN VITROGEN 100, Collagen Co.). After the culture for 2 days, 1 mM (final concentration) of dibutyl cAMP and 2.5 µM of bromodeoxyuridine (SIGMA) were added. After the culture for additional 10 to 14 days, the cells were subjected to the activity determination. The medium for IMR-32 cells thus prepared was replaced with 1 ml of Phenol Red-free Eagle minimum essential medium (GIBCO) containing 1 ml of 10 µM fura-2/AM (Dojin Kagaku, Co.) and earle's salts supplement, and the incubation was conducted at 25° C. for 1 hour.

Then the medium was replaced with Phenol Red-free Eagle minimum essential medium (GIBCO) containing earle's salts supplement, from which fura-2/AM had been removed. After the incubation at 37° C. for 1 hour, the medium was replaced with a recording medium (20 mM of HEPES-KOH, 115 mM of NaCl, 5.4 mM of KCl, 0.8 mM of $MgCl_2$, 1.8 mM of $CaCl_2$ and 13.8 mM of D-glucose). Antagonistic activity on N-type calcium channel was determined and analyzed by using a fluorescence microscope (Nikon Corporation) and an image analysis device ARGUS 50 (Hamamatsu Photonics). In particular, a recording medium (20 mM of HEPES-KOH, 115 mM of NaCl, 5.4 mM of KCl, 0.8 mM of $MgCl_2$, 1.8 mM of $CaCl_2$ and 13.8 mM of D-glucose) containing 1 µM of Nifedipine was given to the cells by reflux by a Y-tube method. Then a stimulating agent containing 60 mM of potassium chloride was rapidly given by the Y-tube method. Thereafter stimulating agents containing 60 mM of potassium chloride and 0.1, 1 or 10 µM of test compound were successively rapidly given by the Y-tube method to determine the antagonistic activity on the channel. Finally, a stimulating agent containing 60 mM of potassium chloride and 1 µM of omega conotoxin GVIA (Peptide institute, inc.) was rapidly given by the Y-tube method to realize a condition of 100% inhibition of N-type calcium channel.

Table 9 shows the results of the determination of the activity of inhibiting the N-type calcium channel (pIC50) and L-type calcium channel (IC50).

TABLE 9

| Example | N-type inhibition pIC50 | L-type inhibition IC50 (µM) |
|---|---|---|
| 12 | 5.80 | 2.69 |
| 14 | 5.92 | 4.28 |
| 15 | 6.43 | 20.8 |
| 20 | 5.75 | 2.78 |
| 23 | 5.92 | 1.80 |

The same procedure as that of the above-described tests was repeated except for the following changes: 60 mM of potassium chloride-containing stimulating agent was rapidly given by the Y-tube method while the calcium concentration change in the cells was examined in terms of N-type calcium channel activity. Then Stimulating agents containing 60 mM of potassium chloride and 0.1, 1 or 10 µM of test compound were successively and rapidly given by the Y-tube method. A change in calcium concentration in the cells was determined. N-type calcium channel antagonistic activities calculated from the inhibition rates are shown in Table 10.

TABLE 10

| Example | N-type inhibition pIC50 | L-type inhibition IC50 (µM) |
|---|---|---|
| 12 | 5.4 | 2.69 |
| 14 | 5.7 | 4.27 |
| 20 | 5.5 | 2.88 |
| 23 | 5.8 | 1.82 |
| 33 | 5.8 | 1.70 |
| 54 | 5.7 | 1.58 |
| 57 | 5.8 | 1.78 |
| 60 | 5.8 | 3.89 |

Thus it is apparent that the new dihydropyridine derivatives have excellent N-type calcium channel antagonistic activity.

L-type calcium channel antagonistic activity of the compounds was also examined to find that the activity of them was only weak. They were thus highly selective to N-type calcium channel.

The new dihydropyridine derivatives of the present invention had selective N-type calcium channel antagonistic activity. Thus, the new dihydropyridine derivatives of the present invention are effective in the treatment of acute stage of ischemic cerebrovascular disorders caused by cerebral infarction or intracerebral bleeding (including subarachnoidal hemorrhage); progressive neurodegenerative diseases such as Alzheimer's disease, AIDS related dementia, Parkinson's disease, dementia due to cerebrovascular disorder and ALS; cerebral disorders caused by head injury; pains and cold flush caused by diabetes or thromboangiitis obliterans; various pains such as postoperative pain, migraine and visceral pain; various diseases associated with psychogenic stress such as bronchial asthma, unstable angina and irritable colitis; emotional disorder and withdrawal symptoms after addiction to drugs such as ethanol addiction withdrawal symptoms.

What is claimed is:

1. A dihydropyridine of formula (1) or a pharmaceutically acceptable salt thereof:

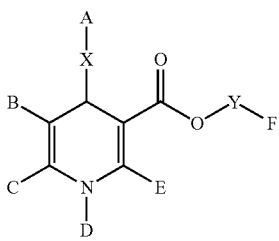

(1)

wherein A represents a group of formula (2), or 1-naphthyl, 2-naphthyl, thiophene-3-yl, thiophene-2-yl, furan-3-yl, furan-2-yl, pyridine-4-yl, pyridine-3-yl, pyridine-2-yl, indole-2-yl or indole-3-yl group:

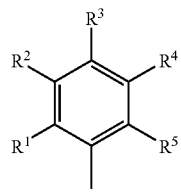

(2)

wherein $R^1$, $R^2$, $R^3$, $R^4$ and $R^5$ may be the same or different from each other and each represent hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl group, an aryl-lower alkoxyl group or an aroyl group;

B represents cyano group, carboxyl group, or a group of formula (3):

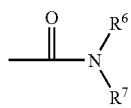

wherein $R^6$ and $R^7$ may be the same or different from each other and each represent hydrogen atom, a lower alkyl group, an amino-lower alkyl group, an amino-lower alkyl group substituted with one or two lower alkyl groups, a carboxy-lower alkyl group, a hydroxy-lower alkyl group, a lower cycloalkyl group, an amino-lower alkenyl group, a carboxy-lower alkenyl group, a hydroxy-lower alkenyl group, an aryl group, a pyridyl group, a furyl group, an aryl-lower alkyl group, a pyridyl-lower alkyl group, a furyl-lower alkyl group, an aryl-lower alkenyl group, or an aryl-lower alkyloxycarbonyl-lower alkyl group;

C and E may be the same or different from each other and each represent hydrogen atom; a lower alkyl group; dimethoxymethyl group; cyano group; a hydroxy-lower alkyl group; a carboxy-lower alkyl group; a halogeno-lower alkyl group; an amino-lower alkyl group, in which the amino group may be substituted with one or two of a lower alkyl group, a lower cycloalkyl group, an aryl group or an aryl-lower alkyl group; an azido-lower alkyl group; an aryl group; a pyridyl group; a furyl group; an aryl-lower alkyl group; a pyridyl-lower alkyl group; a furyl-lower alkyl group; a pyridyl-lower alkoxymethyl group; a furyl-lower alkoxymethyl group; a pyridinylethoxymethyl group; or a carbamoyl-lower alkyl group, in which the carbamoyl group may be substituted with one or two of a lower alkyl group, a lower cycloalkyl group, an aryl group or an aryl-lower alkyl group; a piperidinylethoxymethyl group; wherein said lower alkyl portion of said lower alkyl group, hydroxy-lower alkyl group, carboxy-lower alkyl group, halogeno-lower alkyl group, amino-lower alkyl group, azido-lower alkyl group, aryl-lower alkyl group, and carbamoyl-lower alkyl group may contain a hetero atom, which is selected from the group consisting of oxygen and nitrogen;

D represents a hydrogen atom;

F represents a group of formula (4):

(4)

wherein G and H each represent phenyl group, and I represents hydrogen atom or hydroxyl group;

X represents an interatomic bond, $-CH_2-$, $-CH_2CH_2-$, $-CH=CH-$ or $-C\equiv C-$, and Y represents an alkylene group having 2 or 3 carbon atoms.

2. A dihydropyridine or pharmaceutically acceptable salt thereof according to claim 1, wherein A represents a group of formula (2) and X represents an interatomic bond.

3. A dihydropyridine or pharmaceutically acceptable salt thereof according to claim 2, wherein B represents carboxyl group or a group of formula (3).

4. A dihydropyridine or pharmaceutically acceptable salt thereof according to claim 2, wherein C and B may be the same or different from each other and each represent a lower alkyl group, a hydroxy-lower alkyl group, an aryl-lower alkyl group, a pyridyl-lower alkyl group, or a furyl-lower alkyl group.

5. A dihydropyridine or pharmaceutically acceptable salt thereof according to claim 4, wherein A represents a group of formula (2) wherein $R^1$, $R^3$, $R^4$ and $R^5$ each represent hydrogen atom and $R^2$ represents chlorine atom, bromine atom, iodine atom, nitro group or cyano group, C and B may be the same or different from each other, and they each represent methyl group, ethyl group, a hydroxy-lower alkyl group, an aryl-lower alkyl group, a pyridyl-lower alkyl group, or a furyl-lower alkyl group, and I represents hydrogen atom.

6. A dihydropyridine or pharmaceutically acceptable salt thereof according to claim 5, wherein B represents carboxyl group.

7. A dihydropyridine or pharmaceutically acceptable salt thereof according to claim 2, wherein C represents hydrogen atom, a lower alkyl group, dimethoxymethyl group, cyano group, a hydroxy-lower alkyl group, a halogeno-lower alkyl group, an amino-lower alkyl group (in which the amino group may be substituted with one or two of a lower alkyl group, a lower cycloalkyl group, an aryl group and an aryl-lower alkyl group), an azido-lower alkyl group, an aryl group, a pyridyl group, a furyl group, an aryl-lower alkyl group, a pyridyl-lower alkyl group, a furyl-lower alkyl group, or a carbamoyl-lower alkyl group (In which the carbamoyl group may be substituted with one or two of a lower alkyl group, a lower cycloalkyl group, an aryl group and an aryl-lower alkyl group), and E represents methyl group, ethyl group, a lower alkoxymethyl group, a hydroxy-lower alkoxymethyl group, an aryl-lower alkoxymethyl group, a pyridyl-lower alkoxymethyl group, or a furyl-lower alkoxymethyl group.

8. A dihydropyridine or pharmaceutically acceptable salt thereof according to claim 7 wherein B represents carboxyl group.

9. A dihydropyridine or pharmaceutically acceptable salt thereof according to claim 1 wherein A represents a group of formula (2), C and E may be the same or different from each other, and they each represent a lower alkyl group, an aryl-lower alkyl group, a pyridyl-lower alkyl group, a furyl-lower alkyl group, or a hydroxy-lower alkyl group, and X represents an interatomic bond.

10. A dihydropyridine or pharmaceutically acceptable salt thereof according to claim 9, wherein B represents carboxyl group.

11. A pharmaceutical composition comprising a dihydropyridine or pharmaceutically acceptable salt thereof according to claim 1 and an inert carrier.

12. A pharmaceutical composition comprising a dihydropyridine or pharmaceutically acceptable salt thereof according to claim 2 and an inert carrier.

13. A pharmaceutical composition comprising a dihydropyridine or pharmaceutically acceptable salt thereof according to claim 9 and an inert carrier.

14. A dihydropyridine or pharmaceutically acceptable salt thereof according to claim 1, wherein said pyridyl-lower alkyl group is a pyridylmethyl group, and said pyridyl-lower alkoxymethyl group is a 2-(2-pyridyl)ethoxymethyl group, a 2-(3-pyridyl)ethoxymethyl group, or a 2-(4-pyridyl)ethoxymethyl group.

15. A pharmaceutical composition according to claim 11, wherein said pyridyl-lower alkyl group is a pyridylmethyl group, and said pyridyl-lower alkoxymethyl group is a 2-(2-pyridyl)ethoxymethyl group, a 2-(3-pyridyl)ethoxymethyl group, or a 2-(4-pyridyl)ethoxymethyl group.

16. A pharmaceutical composition according to claim 11, wherein C is a 2-piperidinoethoxymethyl group or a trifluoromethyl group.

17. A dihydropyridine or pharmaceutically acceptable salt thereof according to claim 1, wherein C is a 2-piperidinoethoxymethyl group or a trifluoromethyl group.

* * * * *